(12) United States Patent
Kaleko et al.

(10) Patent No.: US 11,596,674 B2
(45) Date of Patent: Mar. 7, 2023

(54) METHOD AND COMPOSITIONS FOR INHIBITING OR PREVENTING ADVERSE EFFECTS OF ORAL ANTIBIOTICS

(71) Applicant: Synthetic Biologies, Inc., Rockville, MD (US)

(72) Inventors: Michael Kaleko, Rockville, MD (US); Sheila Connelly, Rockville, MD (US); Vincent John Wacher, Rockville, MD (US)

(73) Assignee: Synthetic Biologies, Inc., Rockville, MD (US)

( * ) Notice: Subject to any disclaimer, the term of this patent is extended or adjusted under 35 U.S.C. 154(b) by 273 days.

(21) Appl. No.: 16/998,304

(22) Filed: Aug. 20, 2020

(65) Prior Publication Data

US 2020/0384092 A1    Dec. 10, 2020

Related U.S. Application Data

(63) Continuation of application No. 16/031,266, filed on Jul. 10, 2018, now Pat. No. 10,792,346, which is a continuation of application No. 15/641,806, filed on Jul. 5, 2017, now Pat. No. 10,046,035, which is a continuation of application No. 14/757,522, filed on Dec. 23, 2015, now Pat. No. 9,744,221.

(60) Provisional application No. 62/256,994, filed on Nov. 18, 2015, provisional application No. 62/096,202, filed on Dec. 23, 2014.

(51) Int. Cl.
| | | |
|---|---|---|
| A61K 38/50 | (2006.01) | |
| A61K 38/14 | (2006.01) | |
| A61K 35/74 | (2015.01) | |
| A61K 35/741 | (2015.01) | |
| A61K 9/16 | (2006.01) | |
| A61K 9/50 | (2006.01) | |
| A61K 45/06 | (2006.01) | |
| A61K 31/43 | (2006.01) | |
| A61K 31/424 | (2006.01) | |
| A61K 31/7056 | (2006.01) | |
| A61K 31/4164 | (2006.01) | |

(52) U.S. Cl.
CPC ............ *A61K 38/50* (2013.01); *A61K 9/1652* (2013.01); *A61K 9/5078* (2013.01); *A61K 31/4164* (2013.01); *A61K 31/424* (2013.01); *A61K 31/43* (2013.01); *A61K 31/7056* (2013.01); *A61K 35/74* (2013.01); *A61K 35/741* (2013.01); *A61K 38/14* (2013.01); *A61K 45/06* (2013.01); *A61K 9/5026* (2013.01); *A61K 9/5047* (2013.01); *C12Y 305/02006* (2013.01)

(58) Field of Classification Search
CPC ...... A61K 38/50; A61K 9/1652; A61K 35/74; A61K 38/14; A61K 45/06; A61K 9/5026; A61K 9/5047; C12Y 305/02006
See application file for complete search history.

(56) References Cited

U.S. PATENT DOCUMENTS

| | | |
|---|---|---|
| 2,890,986 A | 6/1959 | Kraut et al. |
| 2,941,995 A | 6/1960 | Doyle et al. |
| 2,982,696 A | 5/1961 | Puetzer et al. |
| 3,070,511 A | 12/1962 | Weitnauer |
| 3,150,059 A | 9/1964 | Kleinschmidt et al. |
| 3,239,394 A | 3/1966 | Walton |
| 3,488,729 A | 1/1970 | Chauvette et al. |
| 3,499,909 A | 3/1970 | Weissenburger et al. |
| 5,607,671 A | 3/1997 | Heino |
| 7,319,030 B2 | 1/2008 | Koski et al. |
| 7,989,192 B2 | 8/2011 | Kaariainen et al. |
| 2004/0248279 A1 | 12/2004 | Sawada et al. |
| 2005/0158843 A1 | 7/2005 | Koski et al. |
| 2005/0249716 A1 | 11/2005 | Bourgeois et al. |
| 2009/0181004 A1 | 7/2009 | Kaariainen et al. |
| 2009/0311234 A1 | 12/2009 | Koski et al. |
| 2010/0152221 A1 | 6/2010 | Liang et al. |
| 2013/0216622 A1 | 8/2013 | Koski et al. |

FOREIGN PATENT DOCUMENTS

| | | |
|---|---|---|
| EP | 0384559 A1 | 8/1990 |
| EP | 0420600 A2 | 4/1991 |
| EP | 0420600 A3 | 11/1992 |
| EP | 1564286 A1 | 8/2005 |
| FI | 59265 B | 3/1981 |
| FI | 880017 A | 7/1988 |
| GB | 1241844 A | 8/1971 |
| GB | 1463513 A | 2/1977 |
| GB | 2199582 A | 7/1988 |
| WO | 1988/07865 A1 | 10/1988 |
| WO | 1993/13795 A1 | 7/1993 |
| WO | 1997/03185 A1 | 1/1997 |
| WO | 2003/040352 A1 | 5/2003 |
| WO | 2004/016248 A2 | 2/2004 |
| WO | 2005/078075 A2 | 8/2005 |
| WO | 2006/122835 A1 | 11/2006 |
| WO | 2007/147945 A1 | 12/2007 |
| WO | WO 2008/021394 A2 | 2/2008 |
| WO | 2008/065247 A1 | 6/2008 |
| WO | 2011/148041 A1 | 12/2011 |
| WO | 2016/057744 A1 | 4/2016 |

OTHER PUBLICATIONS

Altschul et al., "Gapped Blast and Psi-Blast: A New Generation of Protein Database Search Programs," Nucleic Acids Research, 1997, vol. 25, No. 17, pp. 3389-3402.

(Continued)

*Primary Examiner* — Kade Ariani
(74) *Attorney, Agent, or Firm* — Morgan, Lewis & Bockius LLP

(57) ABSTRACT

This invention provides, in part, various compositions and methods for protecting the gastrointestinal microbiome from antibiotic disruption.

19 Claims, 31 Drawing Sheets

Specification includes a Sequence Listing.

(56) References Cited

OTHER PUBLICATIONS

Ambler et al., "A Standard Numbering Scheme for the Class A Beta-Lactamases," Biochem. J., 1991, 276, pp. 269-270.
Ambler, "the structure of β-lactamases," Phil. Trans. R. Soc. Lond. B 289: 321-331 (1980).
Bonnet, "Growing Group of Extended-Spectrum β-Lactamases: the CTX-M Enzymes," Antimicrob. Agents Chemother. 48(1):1-14 (2004).
Bonomo et al., "β-Lactamase mutations far from the active site influence inhibitor binding," Biochim. Biophys. Acta 1247:121-125 (1995).
Brogard et al., "Biliary Elimination of Ticarcillin Plus Clavulanic Acid (Ciaventin®), Experimental and Clinical Study," International Journal of Clinical Pharmacology, Therapy and Toxicology, 1989, vol. 27, No. 3, pp. 135-144.
Broun et al., "Catalytic plasticity of fatty acid modification enzymes underlying chemical diversity of plant lipids," Science 1998, vol. 282: 1315-1317.
Bush et al., "A Functional Classification Scheme for β-Lactamases and Its Correlation with Molecular Structure," Antimicrobial Agents and Chemotherapy, Jun. 1995, vol. 39, No. 6, pp. 1211-1233.
Bush, "Metallo-β-Lactamases: A Class Apart," Clinical Infectious Diseases, 1998; 27(Suppl 1):S48-53.
Canica et al., "Phenotypic Study of Resistance of β-Lactamase-Inhibito-Resistant TEM Enzymes Which Differ by Naturally Occurring Variations and by Site-Directed Substitution at Asp276," Antimicrob. Agents Chemother. 42 (6):1323-1328 (1998).
Carfi et al., "1.85 Å Resolution Structure of the Zinc II β-Lactamase from Bacillus cereus," Acta Cryst. (1998) D54: 313-323.
Carfi et al., "The 3-D structure of a zinc metallo-β-lactamase from Bacillus cereus reveals a new type of protein fold," The EMBO Journal, 1995, vol. 14 No. 20: 4914-4921.
Carfi et al., "X-ray Structure of the Zn11 β-Lactamase from Bacteroides fragilis in an Orthorhombic Crystal Form," Acta. Cryst. (1998) D54: 47-57.
Chambliss, "The forgotten dosage form: enteric coated tablets," (1983) Pharm Technol 7, 124-140.
Chen et al.,"β-Lactamase Genes of the Penicillin-Susceptible Bacillus anthracis Sterne Strain," J. Bacteriol. 185 (3):823-830 (2003).
Chica et al., "Semi-rational approaches to engineering enzyme activity: combining the benefits of directed evolution and rational design," Curr. Opin. Biotechnol., 2005, vol. 16: 378-384.
Cole, "Hydrolysis of Penicillins and Related Compounds by the Cell-Bound Penicillin Acylase of Escherichia coli," (1969) Biochem. J. 115, 733-739.
Colombo et al., "The ybxl Gene of Bacillus Subtilis 168 Encodes a Class D β-Lactamase of Low Activity," Antimicrobial Agents and Chemotherapy, Feb. 2004, vol. 48, No. 2, pp. 484-490.
Concha et al., "Crystal Structure of the IMP-1 Metallo β-Lactamase from Pseudomonas aeruginosa and Its Complex with a Mercaptocarboxylate Inhibitor: Binding Determinants of a Potent, Broad-Spectrum Inhibitor," Biochemistry (2000) 39(15): 4288-4298.
Crawford, et al., "Over-expression, purification, and characterization of metallo-β-lactamase ImiS from Aeromonas veronii bv. sobria," Protein Expression and Purification 36 (2004) 272-279.
Davies and Abraham, "Separation, Purification and Properties of β-Lactamase 1 and β-Lactamase II from Bacillus cereus 569/H/9," (1974) Biochem. J. 143:115-127.
Delmas et al., "Structural Insights into Substrate Recognition and Product Expulsion in CTX-M Enzymes," J. Mol. Biol. 400:108-120 (2010).
Devos et al., "Practical limits of function prediction," Proteins: Structure, Function, and Genetics. 2000, vol. 41: 98-107.
Donskey, "Antibiotic Regimens and Intestinal Colonization with Antibiotic-Resistant Gram-Negative Bacilli," Clinical Infectious Diseases, 2006, 43 Suppl 2, pp. S62-69.

Drawz et al., "The Role of a Second-Shell Residue in Modifying Substrate and Inhibitor Interactions in the SHV β-Lactamase: A Study of Ambler Position Asn276," Biochem. 48(21):4557-4566 (2009).
Drawz, et al., "Three Decades of β-Lactamase Inhibitors," Clin Microbiol Rev., 2010, vol. 23, No. 1, pp. 160-201.
Fey et al., Cetriaxone-Resistant Salmonella Infection Acquired by a Child from Cattle, New England J. Med., 2000, 342,1242-1249.
Fonze et al., "Crystal Structures of the Bacillus Licheniformis BS3 Class A β-Lactamase and of the Acyl-Enzyme Adduct Formed with Cefoxitin," Biochemistry, 2002, 41, 1877-1885.
Galleni et al., "Standard Numbering Scheme for Class B β-Lactamases," Antimicrobial Agents and Chemotherapy, Mar. 2001, vol. 45, No. 3, pp. 660-663.
Garau et al., "Update of the Standard Numbering Scheme for Class B β-Lactamases," Guest Commentary, Antimicrobial Agents and Chemotherapy, Jul. 2004, pp. 2347-2349, vol. 48, No. 7.
Garau et al., "A Metallo-β-lactamase Enzyme in Action: Crystal Structures of the Monozinc Carbapenemase CphA and its Complex with Biapenem," J. Mol. Biol. (2005) 345, 785-795.
Gazouli et al., "Effect of substitution of Asn for Arg-276 in the cefotaxime-hydrolyzing class A β-lactamase CTX-M-4," FEMS Microbiol. Lett. 168:289-293 (1998).
Gebhard et al., "Mapping the Distribution of Conformational Information Throughout a Protein Sequence," J. Mol. Biol., 2006, 358, pp. 280-288.
Giakkoupi et al., "Aspartic acid for asparagine substitution at position 276 reduces susceptibility to mechanism-based inhibitors in SHV-1 and SHV-5 β-lactamases," J. Antimicrobial. Chemother. 43:23-29 (1999).
Harmoinen et al., "Enzymic Degradation of a β-Lactam Antibiotic, Ampicillin, in the Gut: A Novel Treatment Modality," Journal of Antimicrobial Chemotherapy, 2003,51, pp. 361-365.
Harmoinen et al., "Orally Administered Targeted Recombinant Beta-Lactamase Prevents Ampicillin-Induced Selective Pressure on the Gut Microbiota: A Novel Approach to Reducing Antimicrobial Resistance," Antimicrobial Agents and Chemotherapy, Jan. 2004, vol. 48, No. 1, pp. 75-79.
Hata et al., "Substrate Deacylation Mechanisms of Serine-β-lactamases," Biol. Pharm. Bull. 29:2151-2159 (2006).
Herzberg, "Refined Crystal Structure of β-Lactamase from Staphylococcus aureus PC1 at 2.0 Å Resolution," J. Mol. Biol. 217:701-719 (1991).
Higgins et al., "In Vitro Activities of the β-Lactamase Inhibitors Clavulanic Acid, Sulbactam, and Tazobactam Alone or in Combination with β-Lactams against Epidemiologically Characterized Multidrug-Resistant Acinetobacter baumannii Strains," Antimicrobial Agents and Chemotherapy, May 2004, vol. 48, No. 5, pp. 1586-1592.
Hirschi A et al. (Abstract) "Campylobacter pylori, Gastritis and Ulcus pepticum," Wien. Klin. Wsch. 14:493-497 (1987).
Horton et al., "Engineering hybrid genes without the use of restriction enzymes: gene splicing by overlap extension," 1989, Gene 77:61-68 (1989).
Huber et al. "Chapter 2. Preparative Methods for 7-Aminocephalosporanic Acid and 6-Aminopenicillanic Acid," (1972) In: Flynn E, ed. Cephalosporins and Penicillins. New York: Academic Press, 27-73.
Hyman, "Anaphylactic Shock After Therapy With Penicillinase," (1959) JAMA 169, 593-594.
Illing et al., "Use of integrational plasmid excision to identify cellular localization of gene expression during sporulation in Bacillus subtilis," J. Bacteriol. 172(12):6937-6941 (1990).
Iserhard et al., "Epidemiology and Treatment of Gastric Campylobacter pylori Infection: more Questions than Answers," (1990) Hepato-Gastroenterol 37, 38-44.
International Search Report PCT/US2015/000228, dated Apr. 19, 2016, 6 pages.
Izui et al., "Large Exopenicillinase, Initial Extracellular Form Detected in Cultures of Bacillus licheniformis," Biochemistry, 1980, 19, pp. 1882-1886.

(56) References Cited

OTHER PUBLICATIONS

Jones et al., Cefoperazone: A Review of its Antimicrobial Spectrum, β-Lactamase Stability, Enzyme Inhibition, and Other in Vitro Characteristics, 1983, Rev. Infectious Disease 5 S108-S126.
Kaleko, et al., "SYN-004, a Class A β-Lactamase Therapy for the Prevention of Antibiotic-Induced Disruption of Intestinal Microflora", Open Forum Infect Dis, Oct. 9, 2014, I (suppl 1): SI15-SI16.
Kato et al., "Nucleotide Sequence of the β-Lactamase Gene of Alkalophilic *Bacillus* sp. Strain 170," J. Gen. Microbiol. 131:3317-3324 (1985).
Westphal et al., "Assessment of Biliary Excretion of Piperacilin-Tazobactam in Humans," Antimicrobial Agents and Chemotherapy, Aug. 1997, vol. 41, No. 8, pp. 1636-1640.
Whisstock et al., "Prediction of protein function from protein sequence," Q. Rev. Biophysics., 2003, vol. 36 (3): 307-340.
Wildfeuer et al., "Pharmacokinetics of Sulbactam and Ampicillin Intravenously Applied in Combination to Healthy Volunteers and Patients", Arzneimittel-Forschung, 1988, vol. 38, No. 11, pp. 1640-1643.
Wishart et al., "A single mutation converts a novel phosphotyrosine binding domain into a dual-specificity phosphatase," J. Biol. Chem., 1995, vol. 270(45): 26782-26785.
Witkowski et al., "Conversion of β-ketoacyl synthase to a Malonyl Decarboxylase by replacement of the active cysteine with glutamine," Biochemistry, 1999, vol. 38: 11643-11650.
Bourgeois et al., Journal of Drug Targeting, 2005, vol. 13, No. 5. pp. 277-284.
Katz, "Probiotics for the Prevention of Antibiotic-associated Diarrhea and Clostridium difficile Diarrhea," J. Clin. Gastroenterol., Mar. 2006, vol. 40, No. 3, pp. 249-255.
Kim and Buyn, "Purification and properties of ampicillin acylase from Pseudomonas melanogenum," (1990) Biochim Biophys Acta 1040, 12-18.
Kim et al., "Construction of spore mutants of Bacillus subtilis for the development as a host for foreign protein production," Biotechnology Letters 23:999-1004 (2001).
Kisselev L., "Polypeptide release factors in prokaryotes and eukaryotes: same function, different structure," Structure, 2002, vol. 10: 8-9.
Knox and Moews, "β-Lactamase of Bacillus licheniformis 749/C: Refinement at 2 Å Resolution and Analysis of Hydration," J. Mol. Bioi., 1991, 220, pp. 435-455.
Knox, "Extended-spectrum and inhibitor-resistant TEM-Type β-lactamases: Mutations, Specificity, and Three-Dimensional Structure," Antimicrob. Agents Chemother., 1995, 39, 2593-2601.
Korhonen et al., "Milk Immunoglobulins and Complement Factors," British Journal of Nutrition, 2000, 84 Suppl 1, pp. S75-80.
Kropp et al., "Metabolism of Thienamycin and Related Carbapenem Antibiotics by the Renal Dipeptidase, Dehydropeptidase-I," (1982) Antimicrob Agents Chemother 22, 62-70.
Kumakura et al., "Metabolic Fate of Clavulanic Acid and BRL 28500 in the Rat and Dog," Chemotherapy (Tokyo), 1986, 34 Suppl 4, pp. 187-201.
Lambert et al., "Susceptibility of Campylobacter pyloridis to 20 antimicrobial agents," (1986) Antimicrob Agents Chemother 30, (210): 510-511.
Li et al., "Bottlenecks in the expression and secretion of heterologous proteins in Bacillus subtilis," Res. Microbiol. 155:605-610 (2004).
Lim et al., "Cloning, Nucleotide Sequence, and Expression of the Bacillus cereus 5/B/6 β-Lactamase II Structural Gene," J. Bacteriol. 170:2873-2878 (1988).
Madan, "Methods of preparing microcapsules: interfacial polymerization," (1978) Pharm Technol 2, 68-75.
Madgwick and Waley, "β-Lactamase I from Bacillus cereus," Biochem. J. 248(3):657-662 (1987).
Madonna et al., "Nucleotide sequence of the β-lactamase I gene of Bacillus cereus strains 569/H and 5/B," Nucl. Acids Res. 15(4):1877 (1987).
Mandell and Sande, "Chapter 46. Antimicrobial Agents," (1990) In: Goodman and Gilman's, The Pharmacological Basis of Therapeutics, 8th Edition. New York: Pergamon Press, 1065-1097.

Marciano et al., "Analysis of the plasticity of location of the Arg244 positive charge within the active site of the TEM-1 β-lactamase," Prot. Sci. 18:2080-2089 (2009).
Marmur, "A Procedure for the Isolation of Deoxyribonucleic Acid from Micro-organisms," J. Mol. Biol. (1961) 3: 208-218.
Matagne et al., "Catalytic properties of class A β-lactamases: efficiency and diversity," Biochem. J. 330:581-598 (1998).
Matagne et al., "Ragged N-termini and other Variants of Class A β-Lactamases Analysed by Chromatofocusing," Biochem. J., 1991, 273, pp. 503-510.
Mentula et al., "Inhibition of ampicillin-induced emergence of resistance in intestinal coliforms by targeted recombinant β-lactamase," International Journal of Antimicrobial Agents, (2004)24:555-561.
Mezes, et al., "Construction of penP delta 1, Bacillus licheniformis 749/C β-Lactamase Lacking Site for Lipoprotein Modification," The Journal of Biological Chemistry, 1993, vol. 258, No. 18, pp. 11211-11218.
O'Callaghan et al., "Novel Method for Detection of β-Lactamases by Using a Chromogenic Cephalosporin Substrate," Antimicrobial Agents and Chemotherapy, Apr. 1972, vol. 1, No. 4, pp. 283-288.
Pedraza-Reyes et al., "Temporal Regulation and Forespore-Specific Expression of the Spore Photoproduct Lyase Gene by Sigma-G RNA Polymerase during Bacillus subtilis Sporulation," J. Bacteriol. 176(13): 3983-3991. 1994.
Perez-Llarena et al., "Structure-function studies of arginine at position 276 in CTX-M β-lactamases," J. Antimicrob. Chemother. 61(4):792-797 (2008).
Pitout, (Abstract) "Ipsat P1A, a class A beta-lactamase therapy for the prevention of penicillin-induced disruption to the intestinal microflora," Current Opinion in investigational drugs (London, England: 2000) 10.8 (2009): 838-844.
Pluckthun and Knowles, "The consequence of of stepwise deletions from the signal-processing site of β-lactamase," J. Biol.Chem., 1987, vol. 262 (9): 3951-3957.
Rauws and Tytgat, "Cure of duodenal ulcer associated with eradication of Helicobacter pylori," (1990) Lancet 335, 1233-1235.
Rauws et al., "Campylobacter pyloridis-Associated Chronic Active Antral Gastritis," (1988) Gastroenterol 94, 33-40.
Rice et al., "β-Lactam Antibiotics and Gastrointestinal Colonization with Vancomycin-Resistant Enterococci," J. Infect. Dis., 2004, 189, pp. 1113-1118.
Sambrook and Russell. Molecular Cloning: A Laboratory Manual. "In vitro Amplification of DNA by the Polymerase Chain Reaction," vol. 2, Ch. 8, pp. 8.1-8.126. 2001.
Sande et al., "Chapter 44. Antimicrobial Agents," (1990) In: Goodman and Gilman's, The Pharmacological Basis of Therapeutics, 8th Edition. New York: Pergamon Press, 1018-1046.
Santillana et al., "Crystal structure of the carbapenemase OXA-24 reveals insights into the mechanism of carbapenem hydrolysis," Proc. Natl. Acad. Sci. USA, 104:5354-5359 (2007).
Santos et al., "Folding of an Abridged β-Lactamase," Biochemistry, 2004, 43, pp. 1715-1723.
Saunders et al., "Use of Chromosomal Integration in the Establishment and Expression of blaZ, a *Staphylococcus aureus* β-lactamase Gene, in Bacillus subtilis," J. Bacteriol. 157(3): 718-726. 1984.
Saves et al., "The Asparagine to Aspartic Acid Substitution at Position 276 of TEM-35 and TEM-36 Is Involved in the β-Lactamase Resistance to Clavulanic Acid," J. Biol. Chem. 270:18240-18245 (1995).
Sawa et al., (Abstract) "The Effect of Cefixime on Bacterial Flora in the Intestinal Tracts of Healthy Male Volunteers," (1985) Chemotherapy (Tokyo) 33, Suppl. 6, 169-180.
Sen et al., "Developments in directed evolution for improving enzyme functions," Appl. Biochem. Biotechnol., Aug. 18, 2007, vol. 143: 212-223.
Shimooka et al, (Abstract) "Absorption, Distribution, and Excretion of Sulbactam and Ampilcillin after Intravenous Administration in Rats and Dogs," Chemotherapy (Tokyo), 1988, 36 Suppl 8, pp. 66-80.
Simm et al., "Characterization of Monomeric L1 Metallo-β-lactamase and the Role of the N-terminal Extension in Negative Cooperativity and Antibiotic Hydrolysis," The Journal of Biological Chemistry (Jul. 2002) vol. 277 No. 27: 24744-24752.

(56) References Cited

OTHER PUBLICATIONS

Sjolund et al., "Long-Term Persistence of Resistant *Enterococcus* Species after Antibiotics To Eradicate Helicobacter pylori," Ann. Intern. Med. 139:483-487 (2003).
Stiefel et al., "Oral Administration of β-Lactamase Preserves Colonization Resistance of Piperacillin-Treated Mice," J. Infect. Dis., 2003, 188, pp. 1605-1609.
Stiefel et al., "Orally Administered Recombinant Metallo-β-Lactamase Preserves Colonization Resistance of Piperacillin-Tazobactam-Treated Mice," Antimicrobial Agents and Chemotherapy, Dec. 2005, vol. 49, No. 12, pp. 5190-5191.
Stiefel, et al. "Gastrointestinal Colonization with a Cephalosporinase-Producing *Bacteroides* Species Preserves Colonization Resistance against Vancomycin-Resistant Enterococcus and Clostridium difficile in Cephalosporin-Treated Mice." Antimicrobial Agents and Chemotherapy, 2014, vol. 58, No. 8, pp. 4535-4542.
Sullivan et al., "Effect of Antimicrobial Agents on the Ecological Balance of Human Microflora," Lancet Infect. Dis., 2001, vol. 1, pp. 101-114.
Tarkkanen et al., "P1A Recombinant β-Lactamase Prevents Emergence of Antimicrobial Resistance in Gut Microflora of Healthy Subjects during Intravenous Administration of Ampicillin," Antimicrob. Agents Chemother. 53:2455-2462 (2009).
Therapeutic Drugs (1991), Dollery C, ed. Edinburgh: Churchill Livingstone, "Ceftriaxone (sodium)," c 127-c133.
Tranier et al., "The High Resolution Crystal Structure for Class A β-Lactamase PER-1 Reveals the Bases for Its Increase in Breadth of Activity," J. Biol. Chem. 275:28075-28082 (2000).
Walsh et al., "Metallo-β-Lactamases: the Quiet before the Storm?" Clinical Microbiology Reviews (Apr. 2005) vol. 18 No. 2: 306-325.
Walther-Rasmussen et al., "Terminal truncations in Amp C β-lactamase from a clinical isolate of Pseudomonas aeruginosa," Eur. J. Biochem. (1999) 263: 478-485.

B.

B.

A.

METHOD AND COMPOSITIONS FOR INHIBITING OR PREVENTING ADVERSE EFFECTS OF ORAL ANTIBIOTICS

RELATED APPLICATIONS

The present application is a continuation of U.S. patent application Ser. No. 16/031,266 (now U.S. Pat. No. 10,792,346), filed Jul. 10, 2018, which is a continuation of U.S. patent application Ser. No. 15/641,806 (now U.S. Pat. No. 10,046,035), filed Jul. 5, 2017, which is a continuation of U.S. patent application Ser. No. 14/757,522 (now U.S. Pat. No. 9,744,221), filed Dec. 23, 2015, which claims priority to US Provisional Application Nos. 62/096,202, filed Dec. 23, 2014, and 62/256,994, filed Nov. 18, 2015, the entire contents of which are hereby incorporated by reference.

FIELD OF THE INVENTION

This invention relates to, in part, various compositions and methods for protecting the gastrointestinal microbiome from antibiotic disruption.

BACKGROUND

The human microbiome is proving to be a vital component in both human health and disease. This is particularly true of the gastrointestinal (GI) tract, which houses over one thousand distinct bacterial species and an estimated excess of $1 \times 10^{14}$ microorganisms, and appears to be central in defining human host health status. For example, the microbiome of the GI tract underlies central processes of nutrient capture and metabolism; however, disruption of this microbiome is also believed to be causative of a number of disorders.

Indeed, antibiotics, often a frontline therapy to prevent deleterious effects of microbes on human health, can induce disruption in the microbiome, including in the GI tract, and lead to further disease. For instance, it is often necessary to administer oral antibiotics for the treatment of infections. However, residual oral antibiotics beyond what is needed for eradication of an infection can alter the ecological balance of normal intestinal microbiota in the gut and lead to further disease.

Therefore, there is a need for agents that prevent microbiome disruption by oral antibiotics while not reducing or eradicating the beneficial anti-infective effects of these antibiotics in a subject.

SUMMARY OF THE INVENTION

Accordingly, the present invention provides compositions and methods for protecting the gastrointestinal microbiome of a subject. In one aspect, methods for protecting the microbiome of the GI tract are provided in which an effective amount of a pharmaceutical composition comprising a beta-lactamase is administered to a subject who is undergoing treatment of has recently undergone treatment with an oral antibiotic, wherein the beta-lactamase is capable of deactivating the oral antibiotic. In an embodiment, the beta-lactamase does not substantially interfere with the plasma levels of a systemically absorbed orally administered antibiotic. In another embodiment, the beta-lactamase deactivates excess oral antibiotic residue excreted into the GI tract. In some embodiments, the beta-lactamase deactivates residual active antibiotic that is not absorbed from the GI tract after an oral dose or is returned in active form to the intestinal tract from the systemic circulation. In certain embodiments, an initial and/or adjunctive therapy may be administered to the subject. The initial and/or adjunctive therapy may be one or more of metronidazole, vancomycin, fidaxomicin, rifaximin, charcoal-based binder/adsorbent, fecal bacteriotherapy, probiotic therapy, and antibody therapy. In certain embodiments, the subject may have previously suffered from a microbiome-mediated disorder or may present with symptoms of recurrence of a microbiome-mediated disorder.

In various embodiments, the methods of the invention treat or prevent a microbiome-mediated disorder, such as an antibiotic-induced adverse effect, *Clostridium difficile* (*C. difficile*) infection, *C. difficile*-associated disease, ulcerative colitis, Crohn's disease, and irritable bowel syndrome. In an embodiment, the methods of the invention maintain the normal intestinal microbiota of a subject. For instance, in some embodiments, the methods of the invention maintain a healthy balance (e.g. a healthy ratio and/or healthy distribution) of intestinal microbiota of a subject. In another embodiment, the methods of the invention treat or prevent the overgrowth of one or more pathogenic microorganisms in the GI tract. In a further embodiment, the methods of the inventions find use in treating or preventing a nosocomial infection and/or a secondary emergent infection.

In various embodiments, the beta-lactamase is formulated for GI tract delivery. For example, the beta-lactamase may be enteric coated. In an embodiment, the beta-lactamase is formulated for release in a location in the GI tract in which it deactivates residual or excess oral antibiotic (e.g. residual active antibiotic that is not absorbed from the GI tract after an oral dose or is returned in active form to the intestinal tract from the systemic circulation). In another embodiment, the beta-lactamase is formulated for release in a location in which it prevents a microbicidal activity of the residual or excess oral antibiotic. In a further embodiment, the beta-lactamase is formulated for release in a location in the GI tract in which it does not substantially interfere with the systemic activity of the orally administered antibiotic. In another embodiment, the beta-lactamase is formulated for release in a location in the GI tract that is distal to the release and absorption of the orally administered antibiotic. In various embodiments, the beta-lactamase is formulated for substantially uniform dissolution in the area of release in the GI tract. In still further embodiments, the beta-lactamase is formulated for microorganism-based release in the GI tract.

In various embodiments, methods of the present invention provide combination therapy including beta-lactamase and one or more additional therapeutic agents. In an embodiment, a subject is administered with a beta-lactamase inhibitor that releases in the GI tract proximal to the beta-lactamase.

SYN-004 is displayed as the white box. The boxplot displays the median (line), the quartiles (box) and the range (vertical lines).

Figure 5:
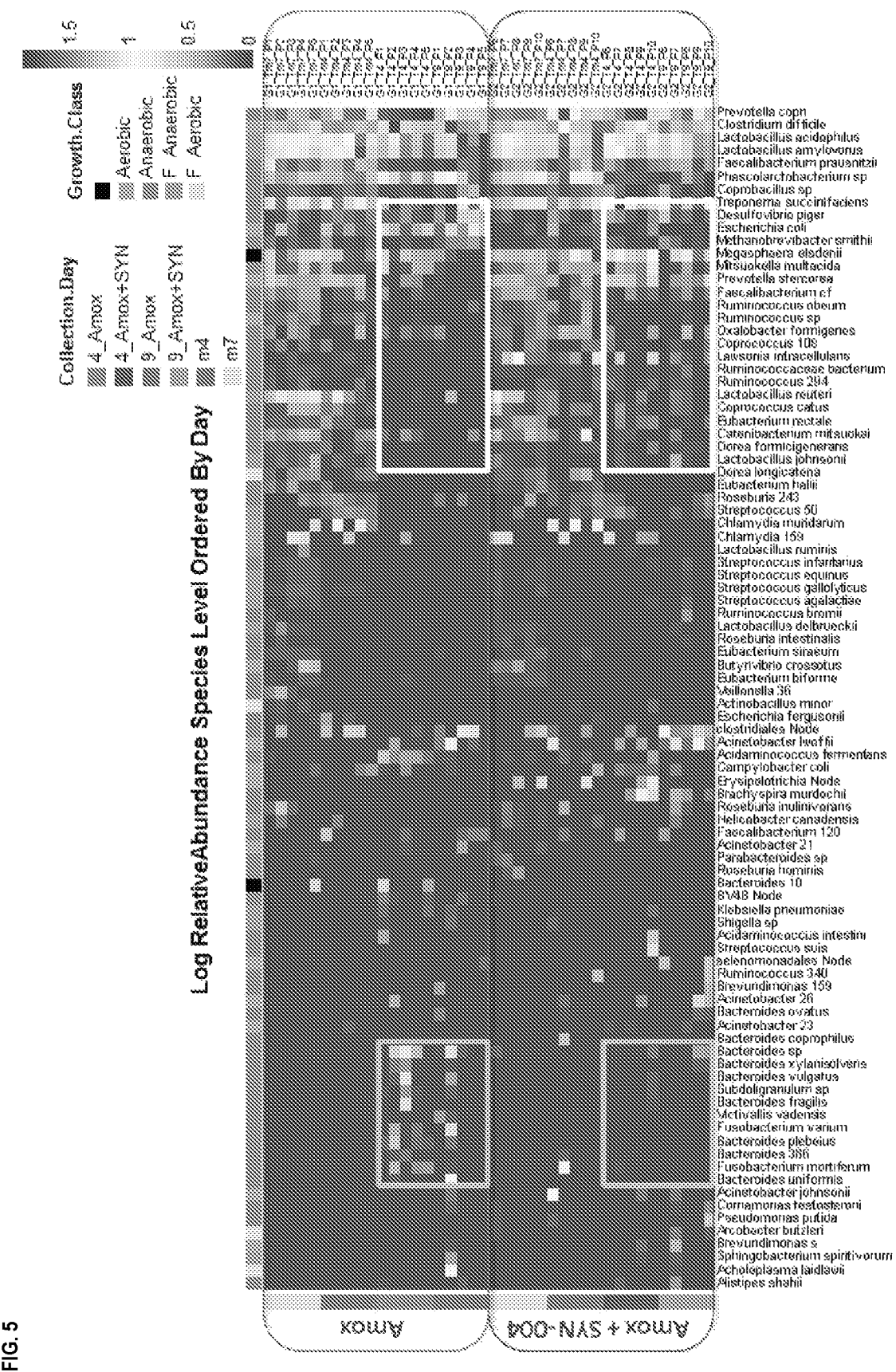

FIG. 5 shows strain abundance heat map from the sequencing analysis of Example 1.

Figure 6:
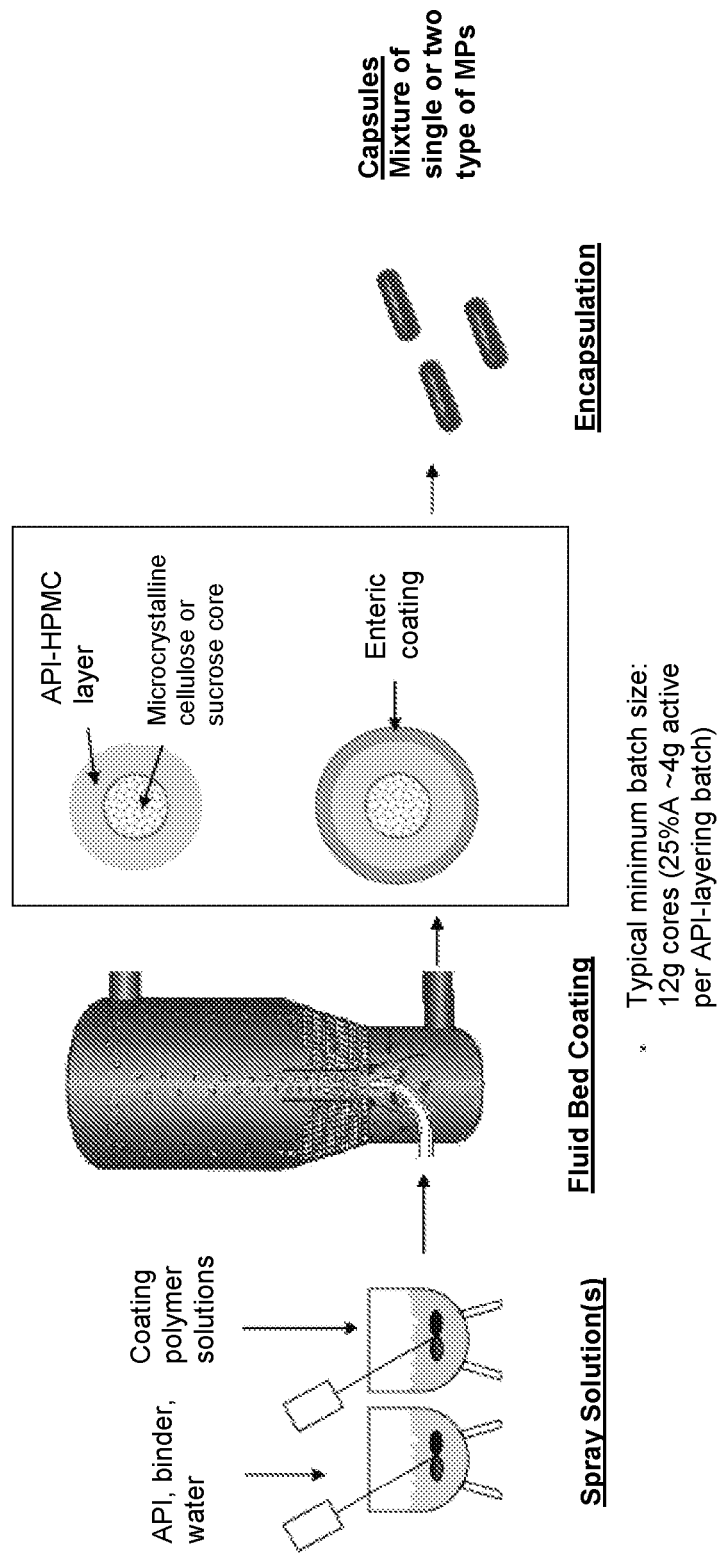

FIG. 6 shows the processing scheme for spray layered multiparticulates as described in Example 2.

Figure 7A:
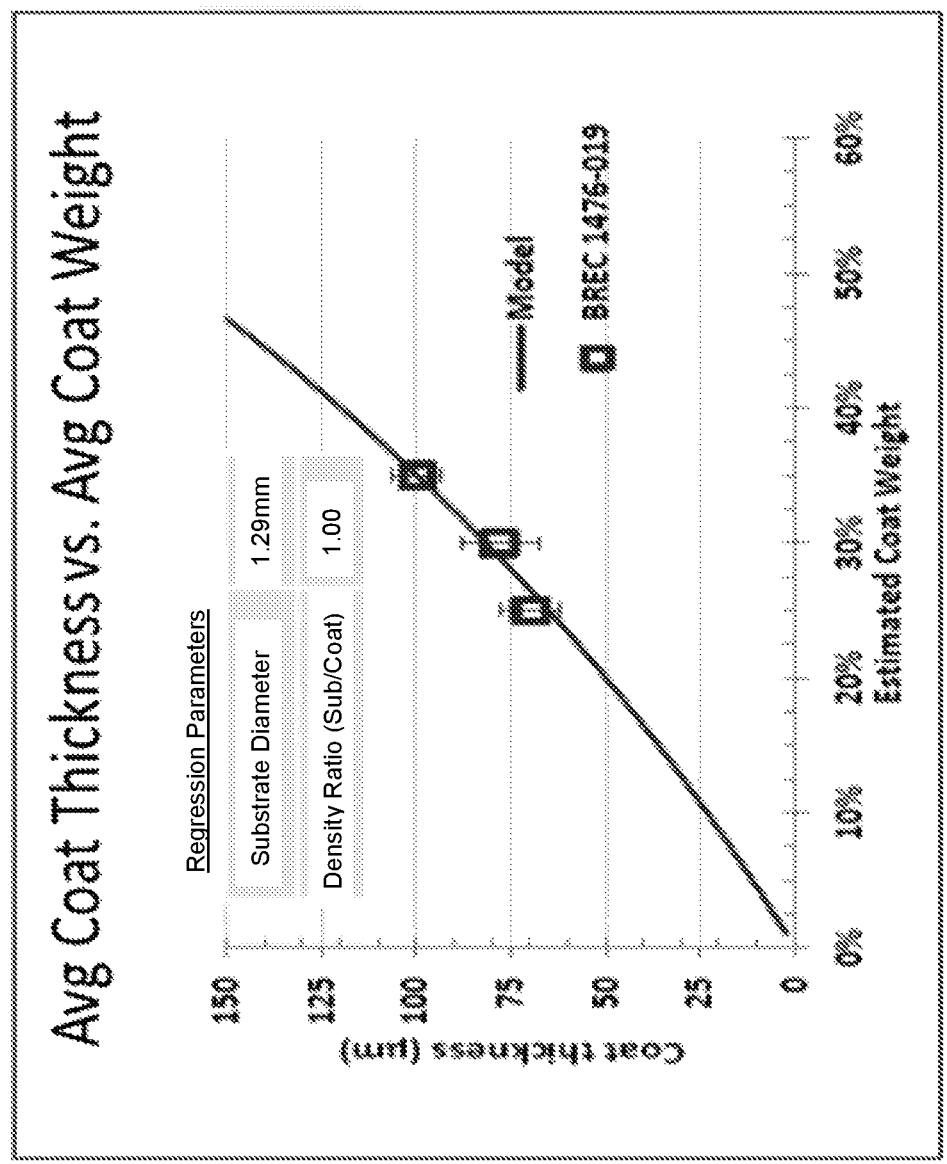
Figure 7:
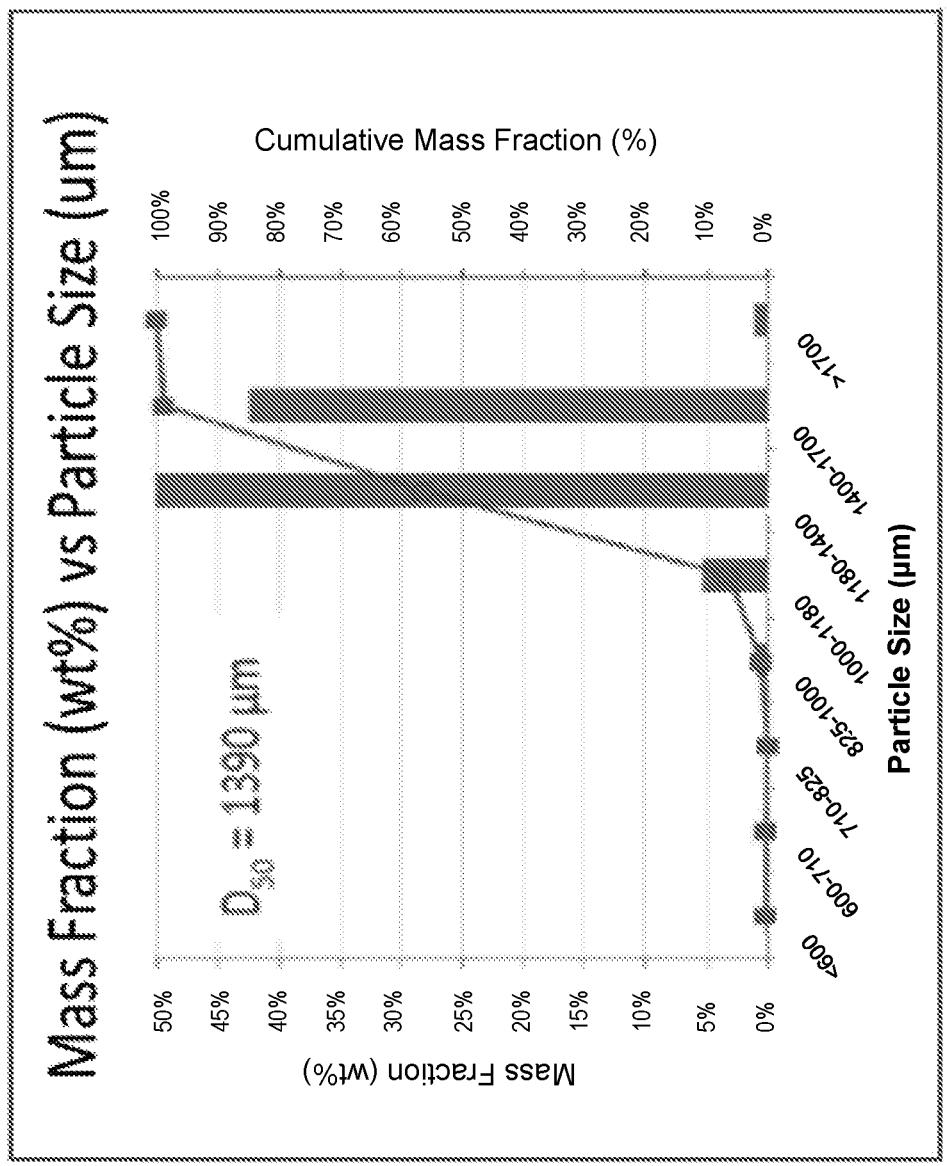

FIG. 7 depicts characterization of the enteric-coated SYN-004 particles that release at pH 6.2. Particles coated with Eudragit L100, Eudragit S100, and triethyl citrate at a ratio of 72.7/18.2/9.1 were characterized based on the average coat thickness vs estimated coat weights (panel A) and the mass fraction vs the particle size (panel B).

Figure 8:
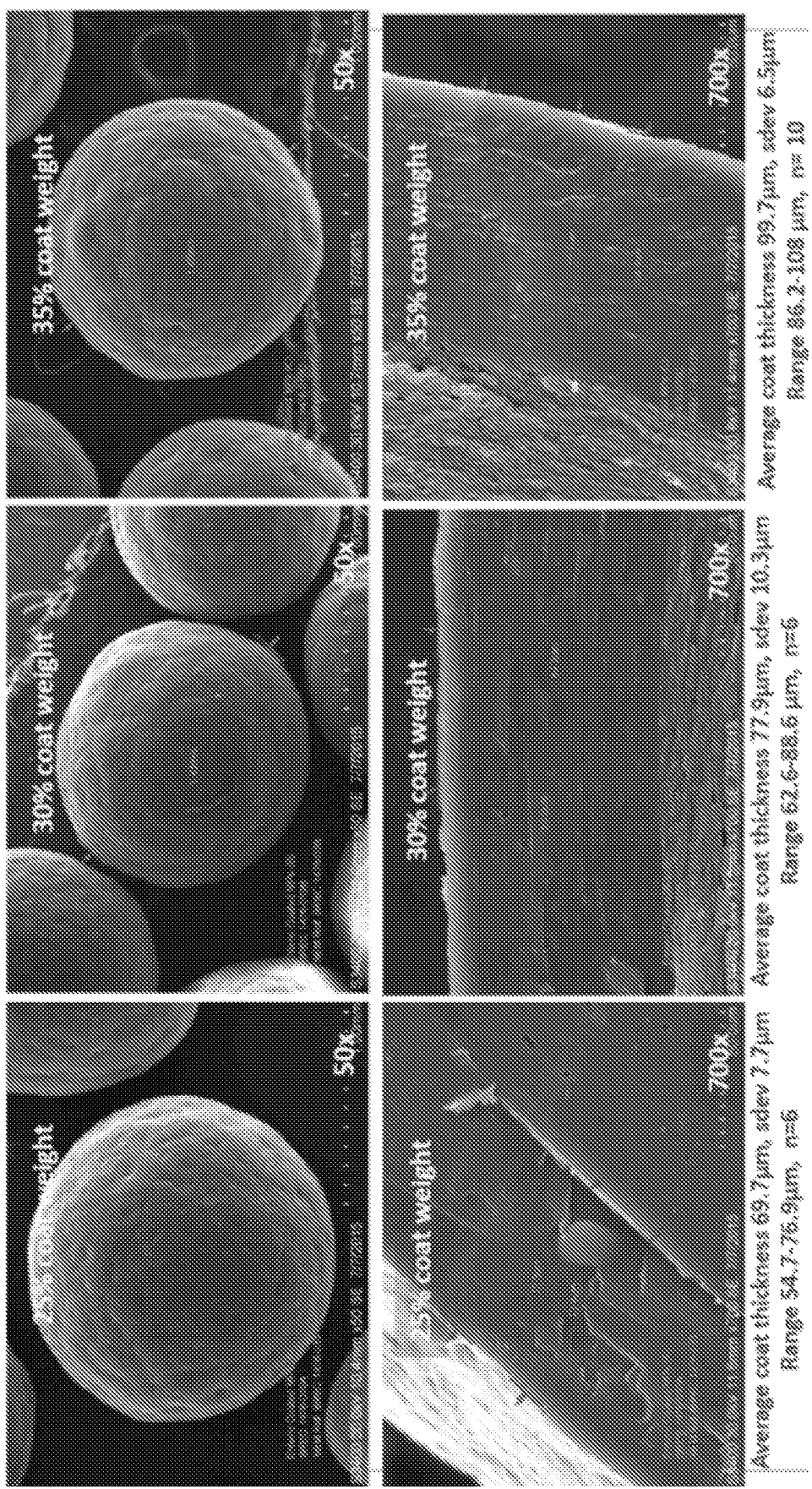

FIG. 8 shows scanning electron microscope images of the enteric-coated SYN-004 particles that release at pH 6.2. Particles coated with Eudragit L100, Eudragit S100, and triethyl citrate at a ratio of 72.7/18.2/9.1 and at different coat weights, i.e., 25%, 30%, and 35%, were subjected to scanning electron microscopy. The top panels display the 50× magnification for particle size characterization, and the lower panels display the 700× magnification of particle cross sections (n=6) for each coating % to allow determination of the coating thicknesses.

Figure 9:
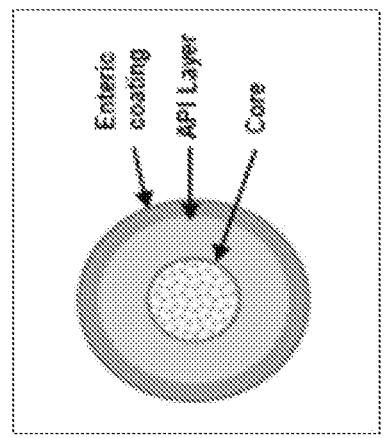
Figure 9:
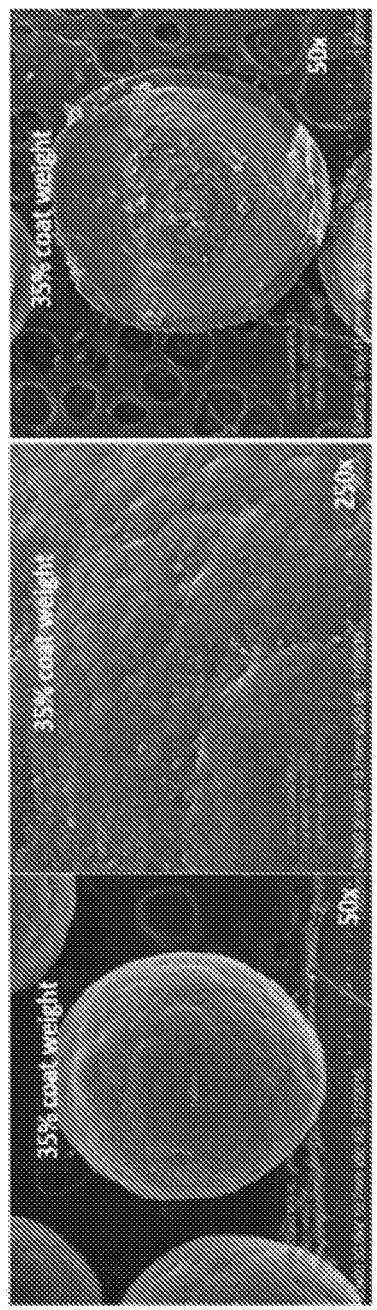

FIG. 9 shows scanning electron microscope images of the enteric-coated SYN-004 particles that release at pH 6.2. Particles coated with Eudragit L100, Eudragit S100, and triethyl citrate at a ratio of 72.7/18.2/9.1 at a 35% coat weight were subjected to scanning electron microscopy. The panels, from left to right, display the 50× magnification for particle size characterization, 250× magnification for surface uniformity analyses, 50× magnification of a particle cross section, and a schematic diagram of a particle displaying the three layers.

Figure 10:
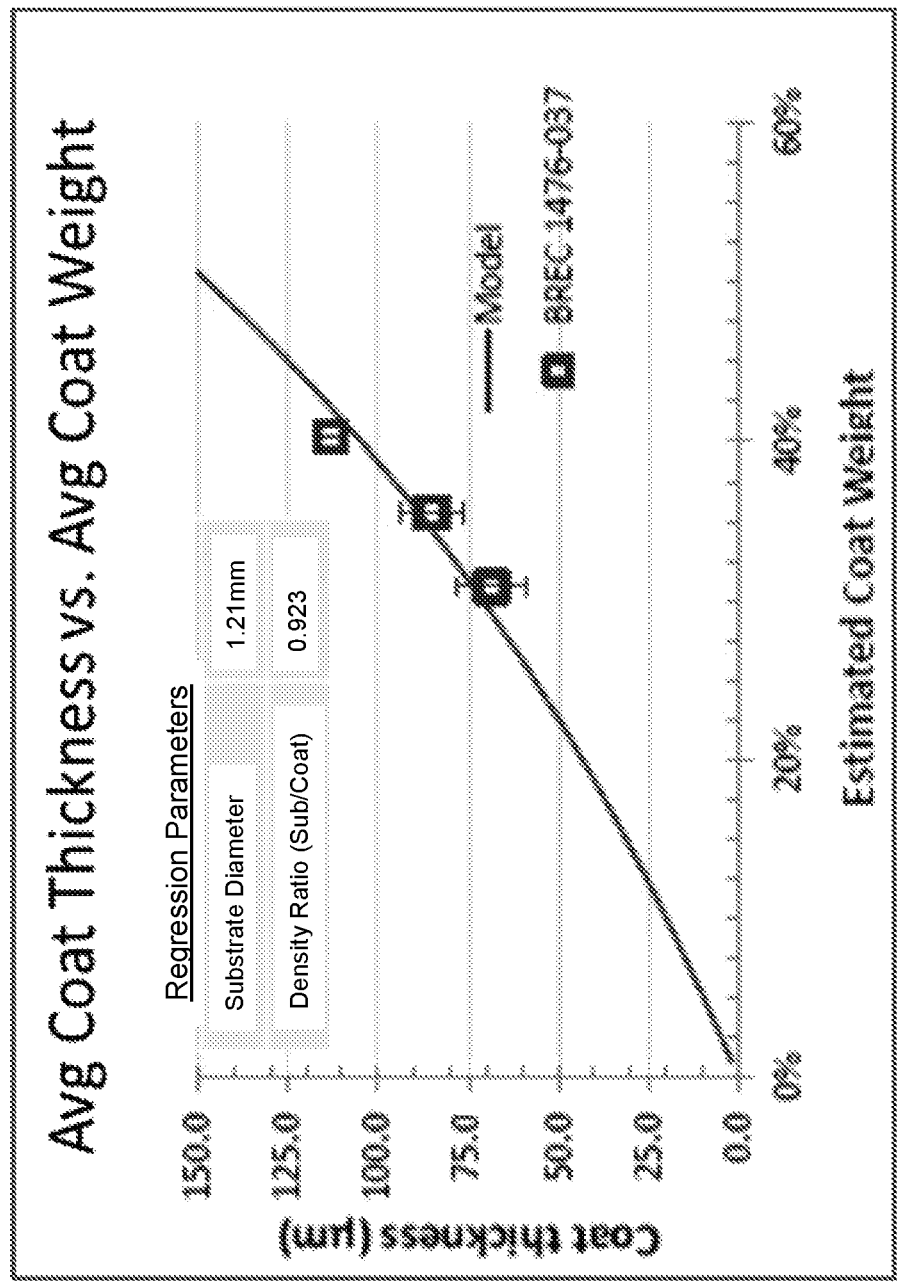
Figure 10:
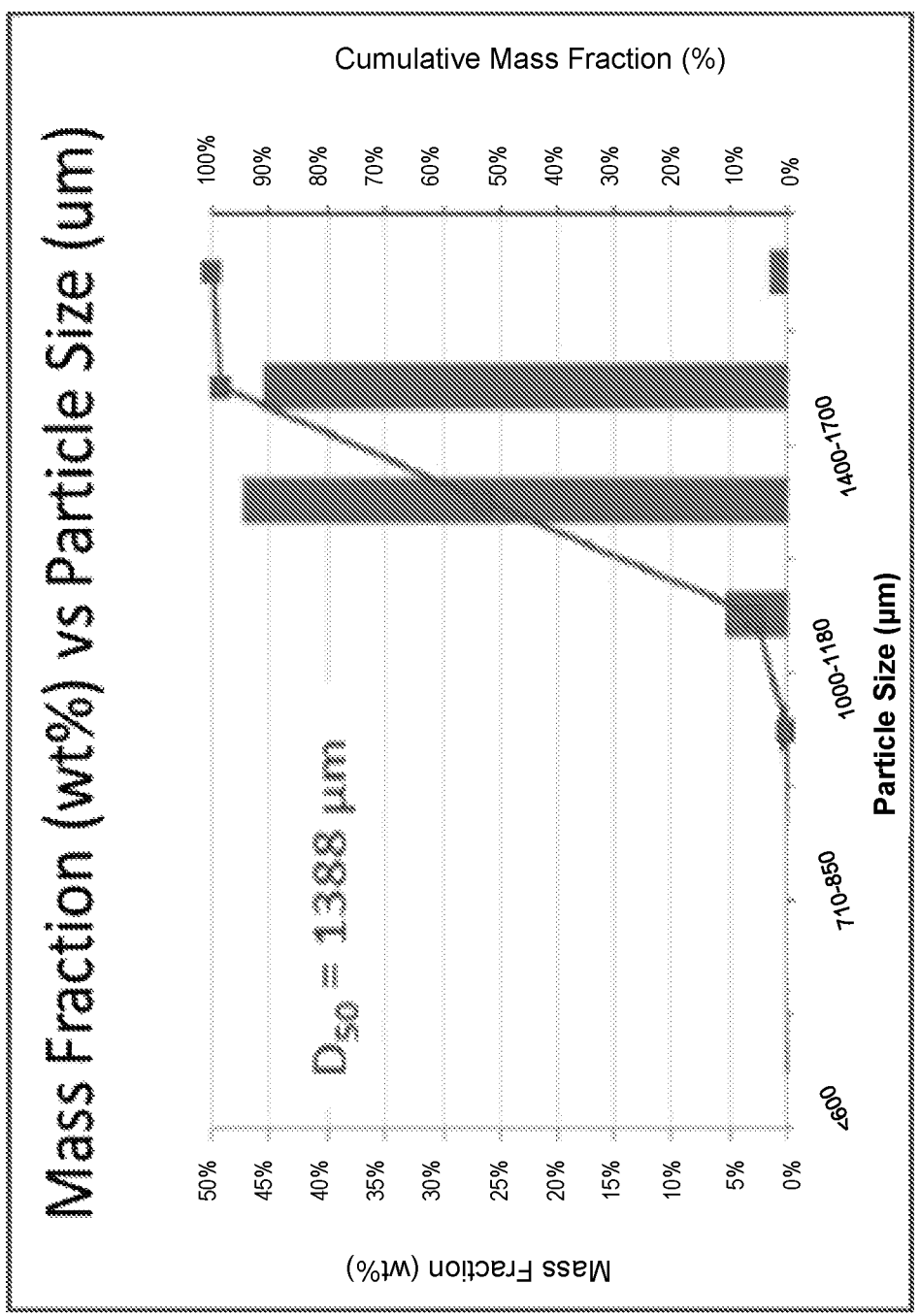

FIG. 10 depicts characterization of the enteric-coated SYN-004 particles that release at pH 6.7. Particles coated with Eudragit L100, Eudragit S100, and triethyl citrate at a ratio of 30/60.9/9.1 were characterized based on the average coat thickness vs estimated coat weights (panel A) and the mass fraction vs the particle size (panel B).

Figure 11:
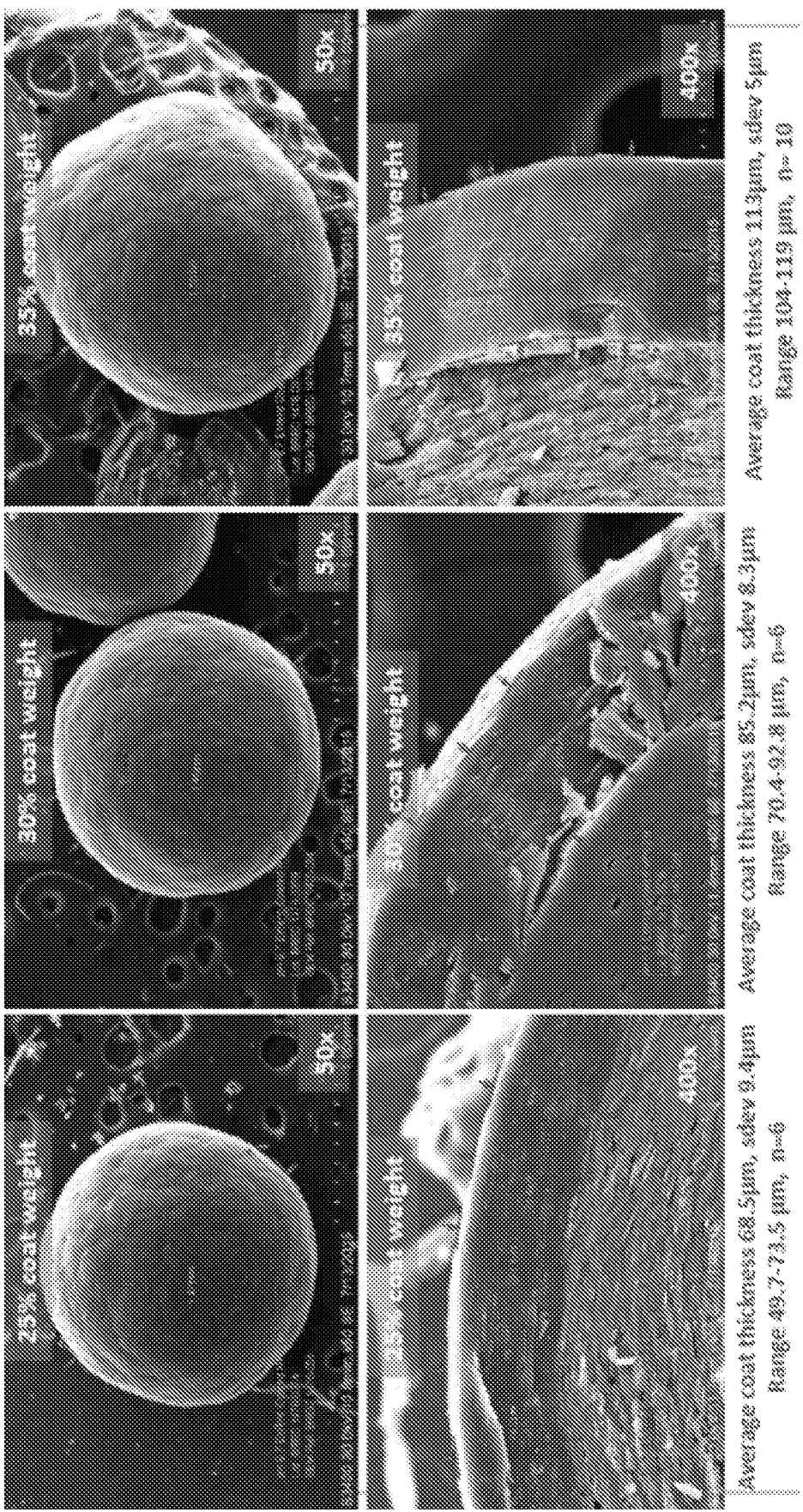

FIG. 11 shows scanning electron microscope images of enteric-coated SYN-004 particles that release at pH 6.7. Particles coated with Eudragit L100, Eudragit S100, and triethyl citrate at a ratio of 30/60.9/9.1 and at different coat weights, i.e., 25%, 30%, and 35%, were subjected to scanning electron microscopy. The top panels display the 50× magnification for particle size characterization, and the lower panels display the 400× magnification of particle cross sections (n=6) for each coating % to allow determination of the coating thicknesses.

Figure 12:
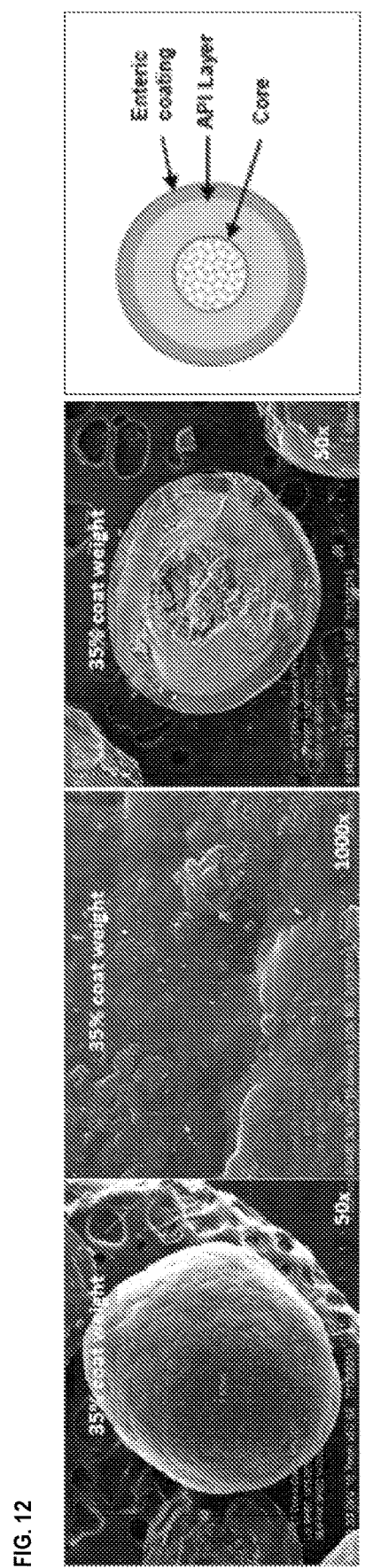

FIG. 12 shows scanning electron microscope images enteric-coated SYN-004 particles that release at pH 6.7. Particles coated with Eudragit L100, Eudragit S100, and triethyl citrate at a ratio of 30/60.9/9.1 at a 35% coat weight were subjected to scanning electron microscopy. The panels, from left to right, display the 50× magnification for particle size characterization, 1000× magnification for surface uniformity analyses, 50× magnification of a particle cross section, and a schematic diagram of a particle displaying the three layers.

Figure 13:
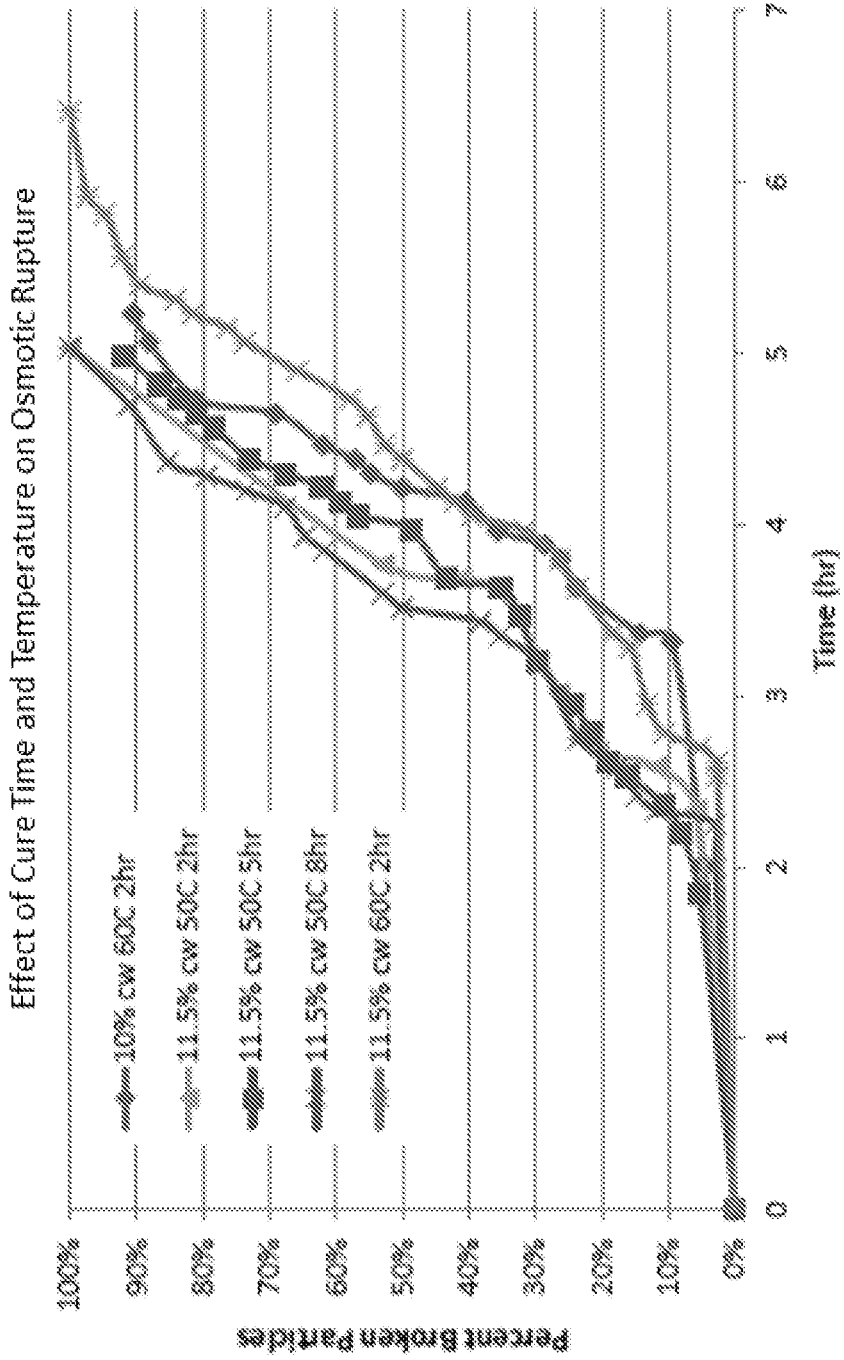

FIG. 13 depicts the osmotic rupture of coated particles. Particles with 10% or 11.5% osmotic coat weights with cure temperatures of 50° C. or 60° C., and cure times of 2, 5, and 8 hours were compared. The indicated pellets were added to a 50 mM $KH_2PO_4$ pH 6.2 buffer at room temperature without stirring and images of the pellets were taken every 5 minutes over 7 hours to evaluate particle disruption. Particle disruption included visible coating changes and significant deformation of the particles. The samples included: 10% coating, cure at 60° C. for 2 hour (diamonds); 11.5% coating, cure at 50° C. for 2 hour (triangles); 11.5% coating, cure at 50° C. for 5 hour (squares); 11.5% coating, cure at 50° C. for 8 hours (Xs); and 11.5% coating, cure at 60° C. for 2 hours (asterisks).

Figure 14:
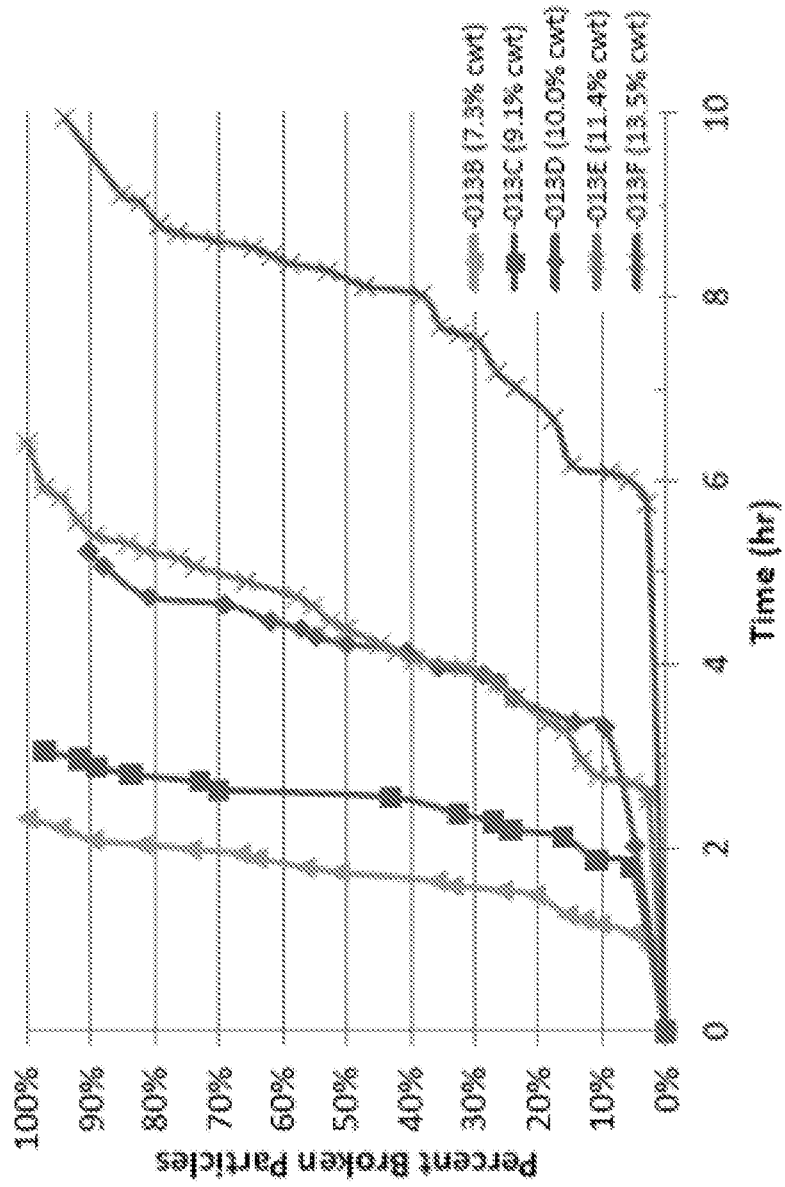

FIG. 14 depicts the osmotic rupture of coated particles. Particles with 7.3%, 9.1%, 10%, 11.4%, or 13.5% osmotic coat weights were compared. The indicated pellets were added to a 50 mM $KH_2PO_4$ pH 6.2 buffer at room temperature without stirring and images of the pellets were taken every 5 minutes over 10 hours to evaluate particle disruption. Particle disruption included visible coating changes and significant deformation of the particles. The samples included: 7.3% coating (triangles); 9.1% coating (squares); 10% coating (diamonds); 11.4% coating (asterisks); and 13.5% coating (Xs).

Figure 15:
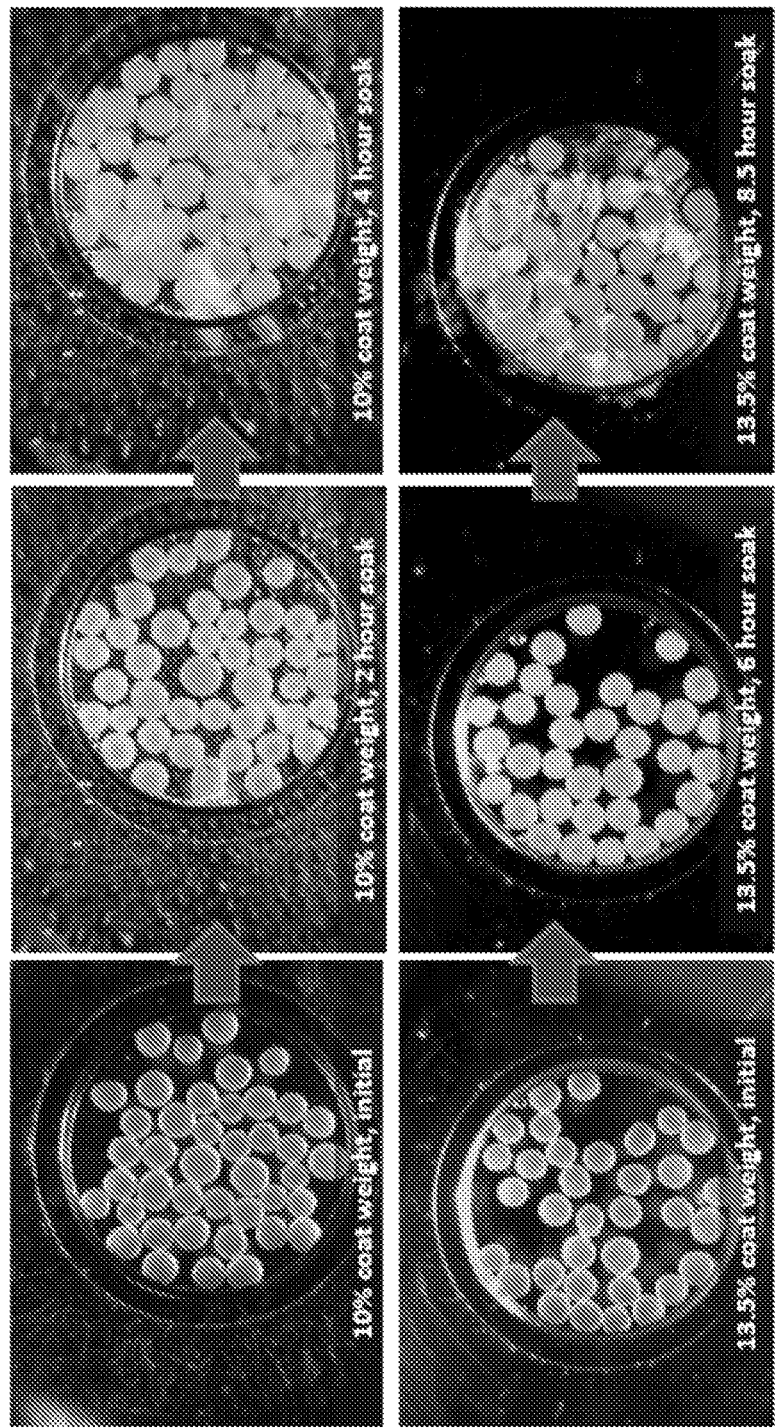

FIG. 15 shows the osmotic rupture of coated particles. Photos of particles with 10% or 13.5% osmotic coat weights are displayed. The indicated pellets were added to a 50 mM $KH_2PO_4$ pH 6.2 buffer at room temperature without stirring. The top panels display the 10% coat weight particles at 0, 2, and 4 hours of soaking. The bottom panels display the 13.5% coat weight particles at 0, 6, and 8.5 hours of soaking.

Figure 16:
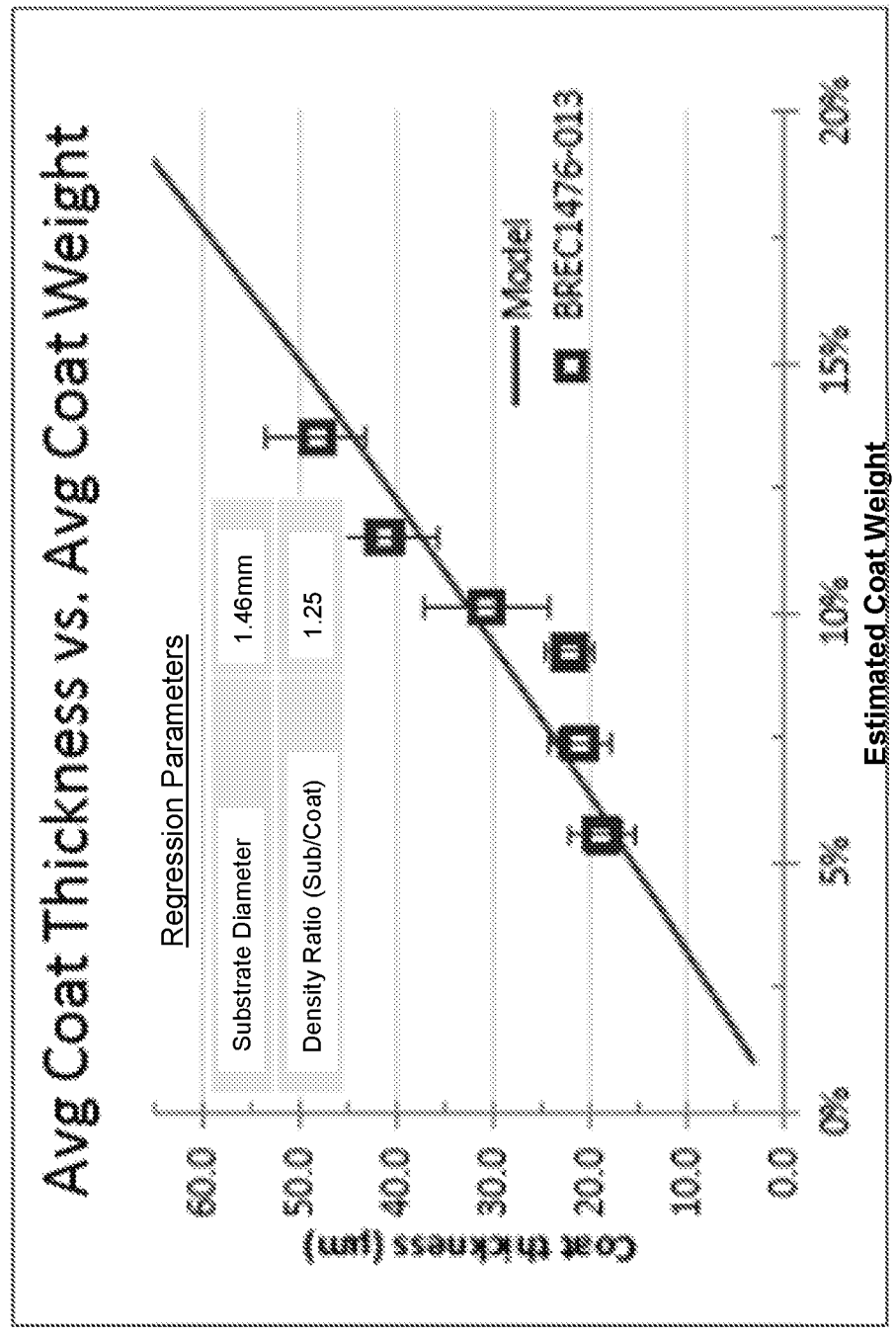
Figure 16:
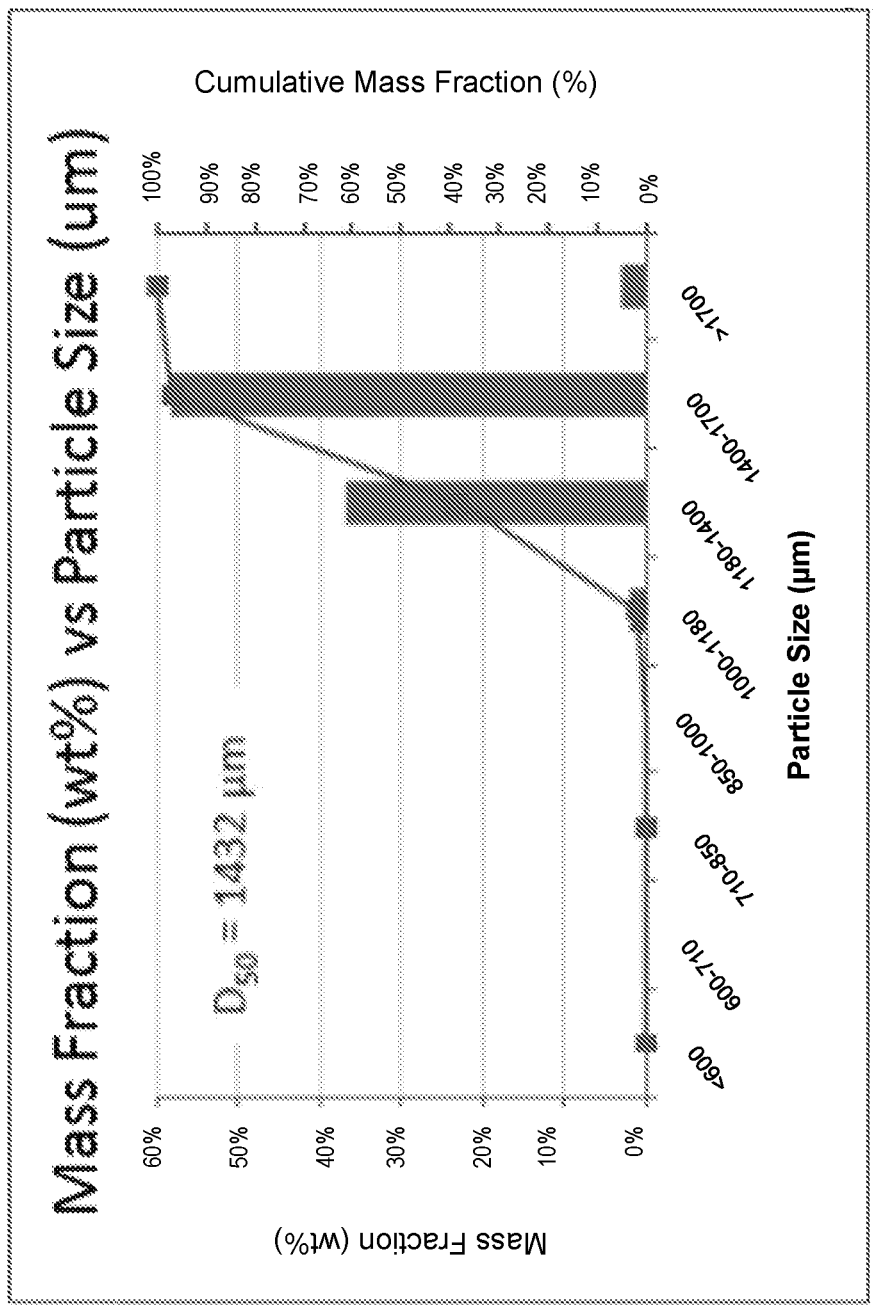

FIG. 16 depicts characterization of the osmotic rupture SYN-004 particles. The particles were characterized based on the average coat thickness vs estimated coat weights (panel A) and the mass fraction vs the particle size (panel B).

Figure 17:
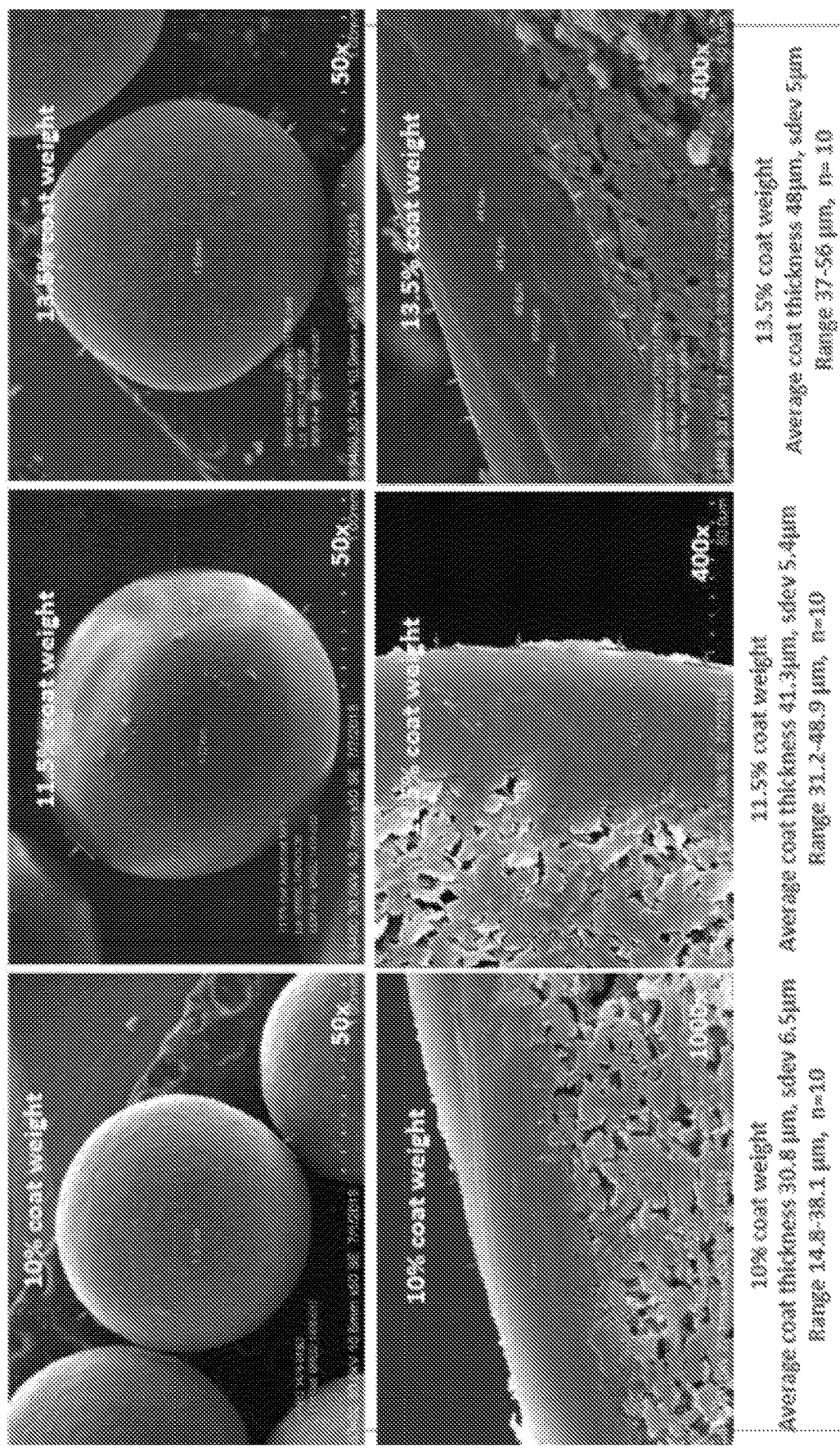

FIG. 17 shows scanning electron microscope images of the osmotic rupture SYN-004 particles. The osmotic rupture particles of different coat weights, 10%, 11.5%, and 13.5% were subjected to scanning electron microscopy. The top panels display the 50× magnification for particle size characterization, and the lower panels display the 1000× or 400× magnification of particle cross sections (n=10) for each coating % to allow determination of the coating thicknesses.

Figure 18:
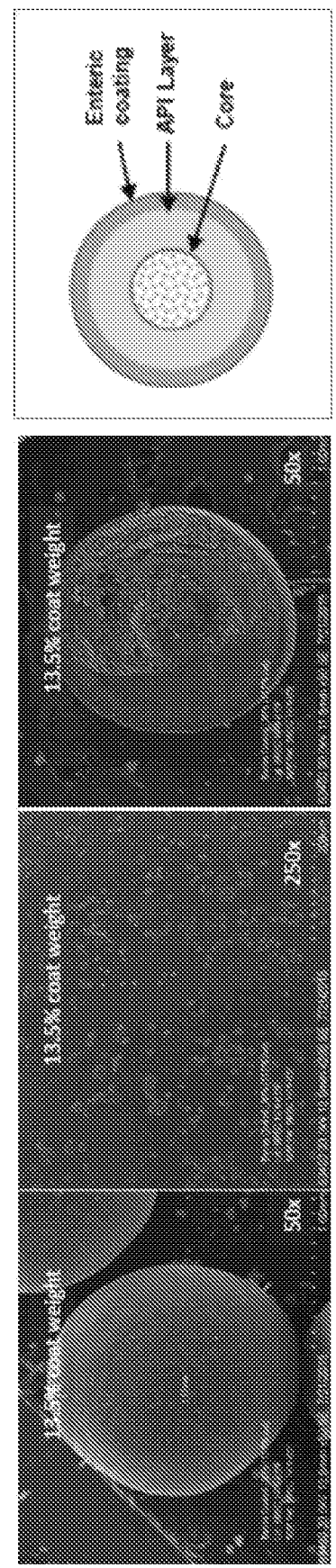

FIG. 18 shows scanning electron microscope images of the osmotic rupture SYN-004 particles. The 13.5% coating weight osmotic rupture particles were subjected to scanning electron microscopy. The panels, from left to right, display the 50× magnification for particle size characterization, 250× magnification for surface uniformity analyses, 50× magnification of a particle cross section, and a schematic diagram of a particle displaying the three layers.

Figure 19:
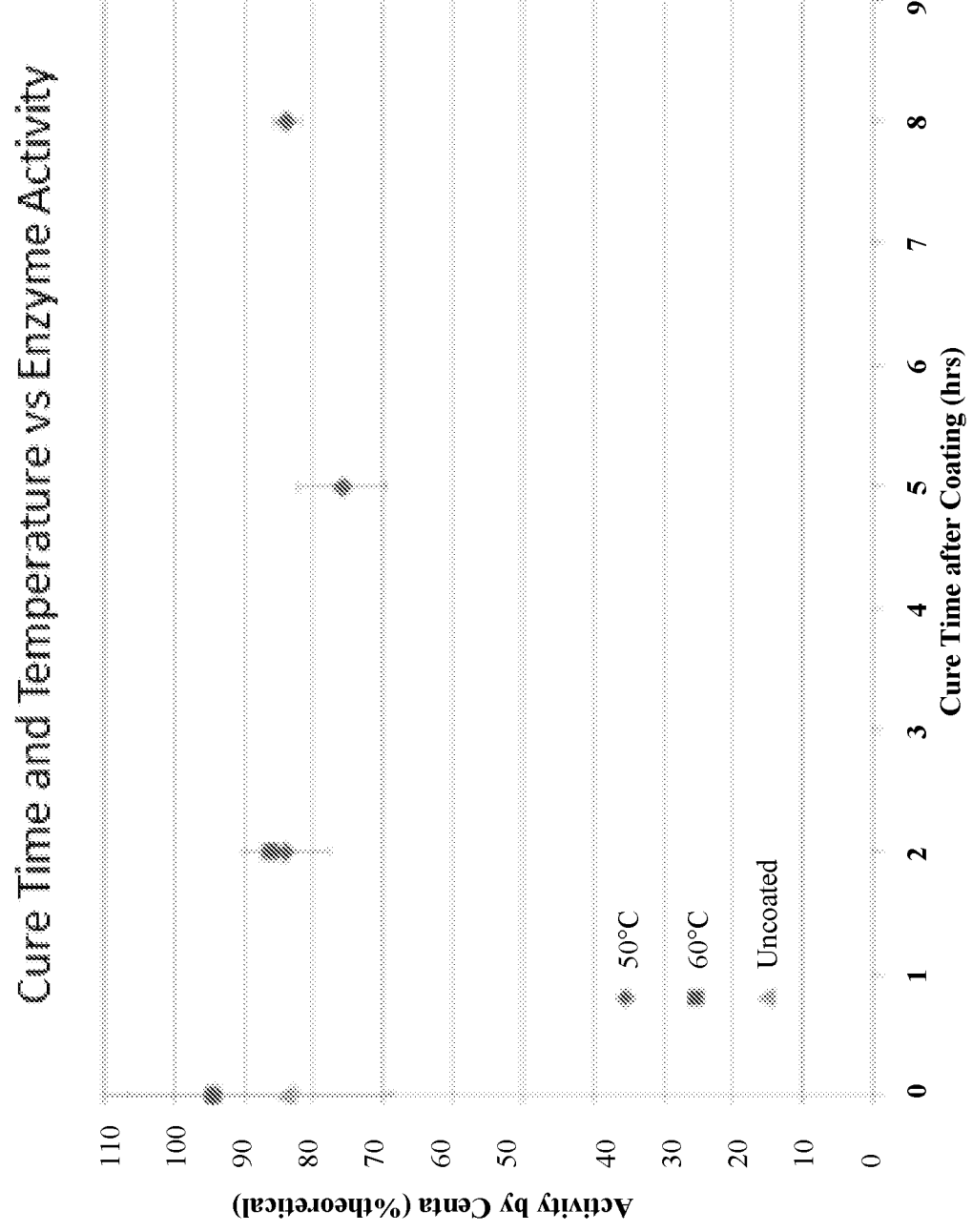

FIG. 19 shows evaluations of cure time and temperature on enzyme activity for osmotic rupture SYN-004 particles. The SYN-004 coated sucrose pellets were coated with a sweller layer and then coated with the osmotic rupture layer. The osmotic layer required a curing step. Cure temperatures of 50° C. or 60° C., and cure times of 0, 2, 5, and 8 hours were evaluated. Pellets were added to a pH 6.8 potassium phosphate buffer and stirred overnight to ensure removal of the entire coating. Aliquots of the buffer were analyzed for SYN-004 biological activity using the CENTA chromogenic microtiter plate assay. Activity is displayed as % of theoretical activity based on the amount of SYN-004 protein present in each formulation. Uncoated (SYN-004 pellet starting material) is displayed as the triangle. 50° C. curing temperature is displayed as the diamond, and 60° C. is displayed as the square.

Figure 20:
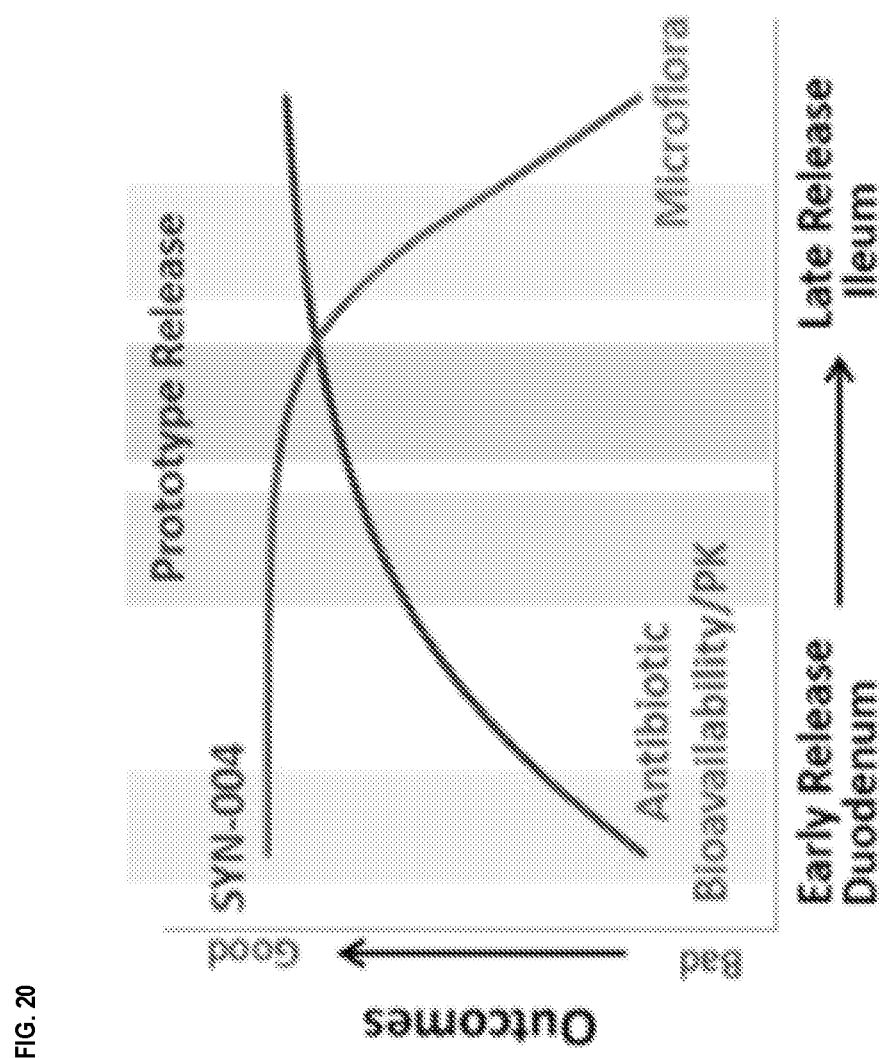

FIG. 20 provides a schematic representation of the criteria for choosing a modified-release formulation of SYN-004 for oral delivery with oral antibiotics. The desired outcome is to not interfere with antibiotic absorption from the intestinal track to maximize antibiotic bioavailability, and to degrade antibiotic that is in the intestinal tract prior to causing damage to the microflora.

Figure 21:
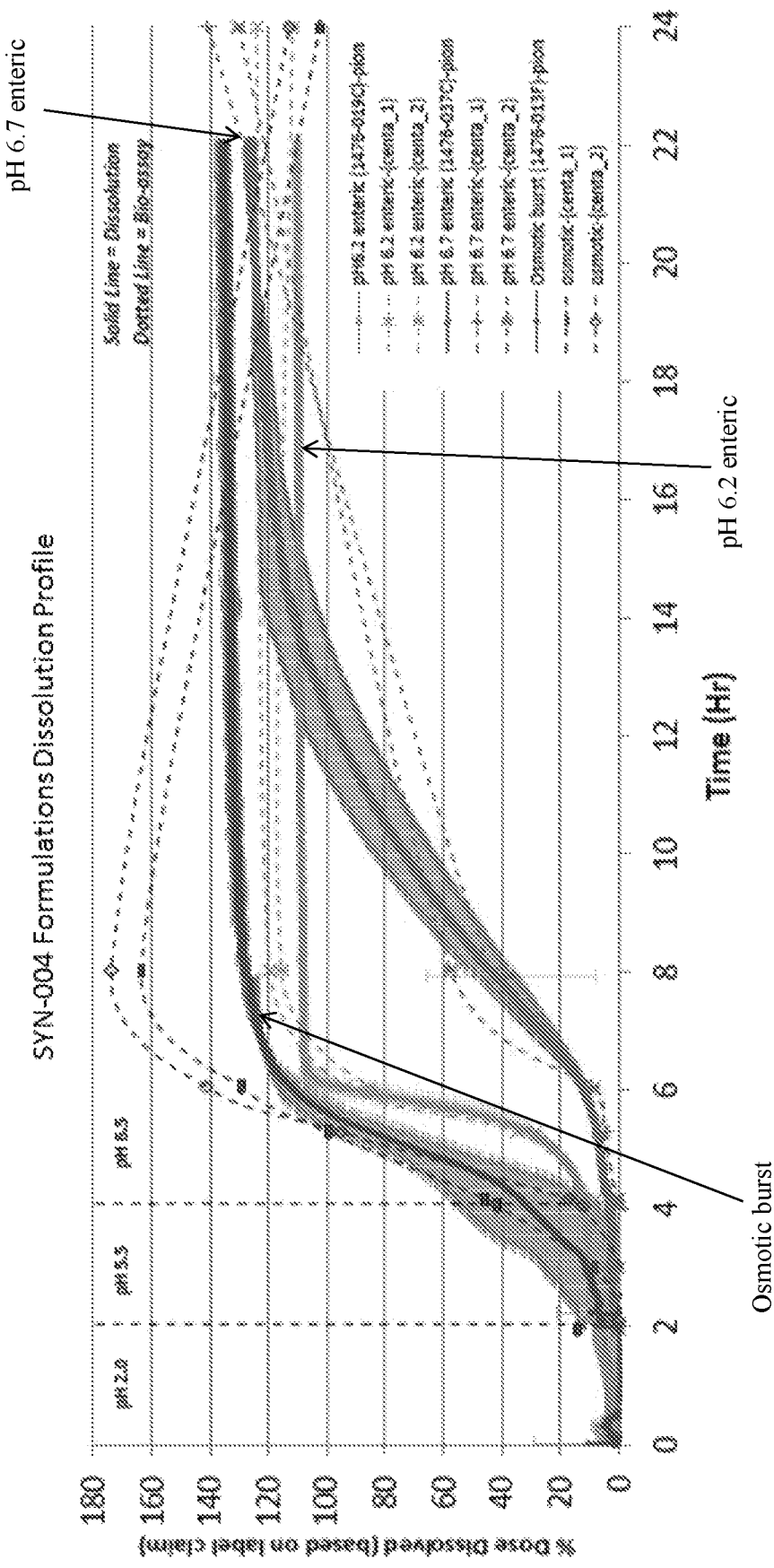

FIG. 21 depicts the SYN-004 pellet dissolution profile. The three SYN-004 formulations (7.5 mg active) were incubated in 0.01N HCl (pH 2.0) for 2 hours, pH 5.5 for 2 hours, and pH 6.5 up to 24 hours. Samples were tested for protein concentration by measuring absorbance at 280 nm (solid lines) and SYN-004 biological activity using the CENT chromogenic assay (dotted lines). The formulations were enteric pH 6.2, enteric pH 6.7, and osmotic as described in Example 2

Figure 22:
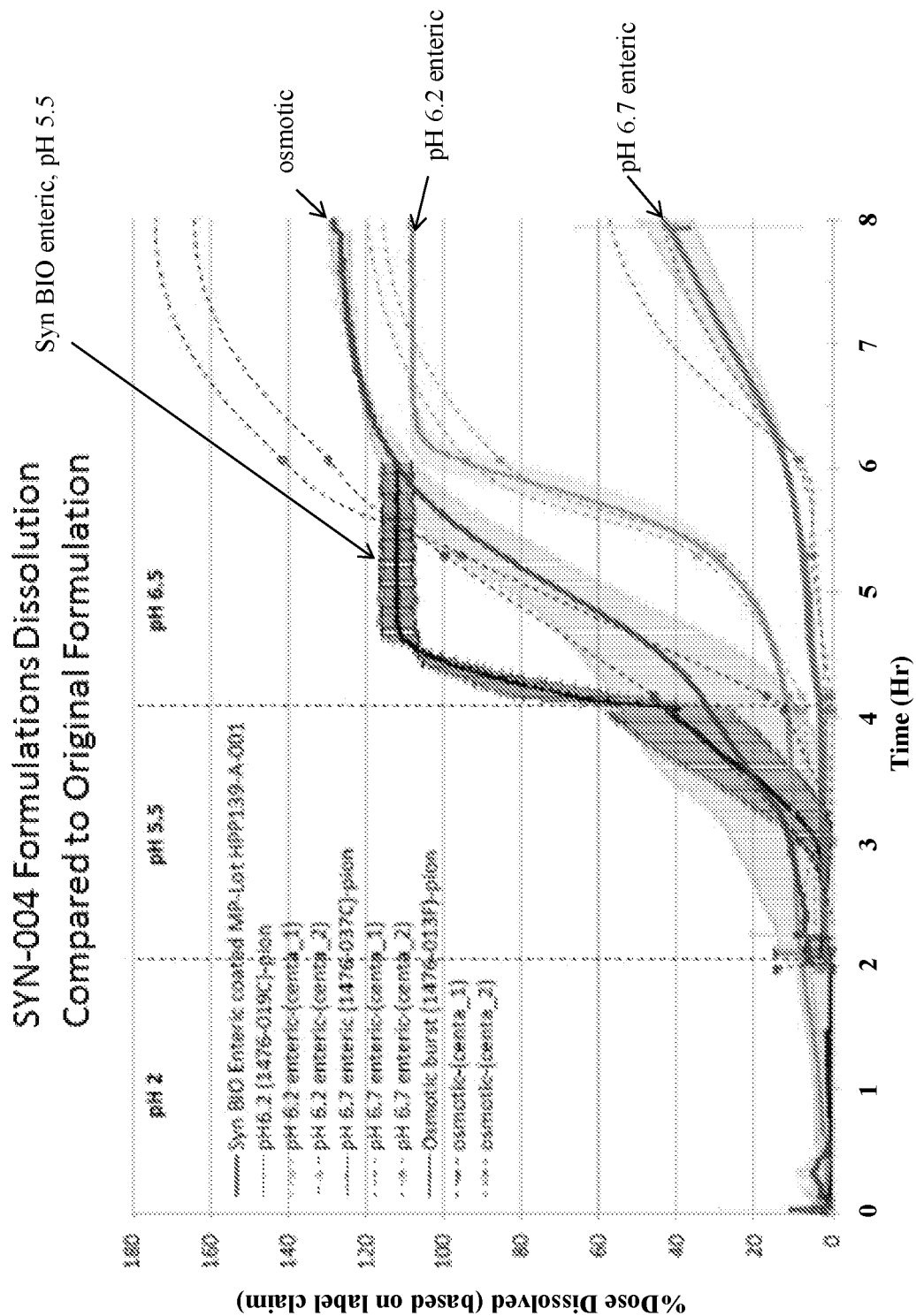

FIG. 22 depicts the SYN-004 pellet dissolution profile compared to original SYN-004 formulation. The original (enteric, pH 5.5) and the three SYN-004 formulations (7.5 mg active) were incubated in 0.01N HCl (pH 2.0) for 2 hours, pH 5.5 for 2 hours, and pH 6.5 up to 24 hours. Samples were tested for protein concentration by measuring absorbance at 280 nm (solid lines) and SYN-004 biological activity using the CENT chromogenic assay (dotted lines). The formulations were SYN-004 original (SynBio enteric, pH 5.5), enteric pH 6.2, enteric pH 6.7, and osmoticas described in Example 2.

Figure 23:
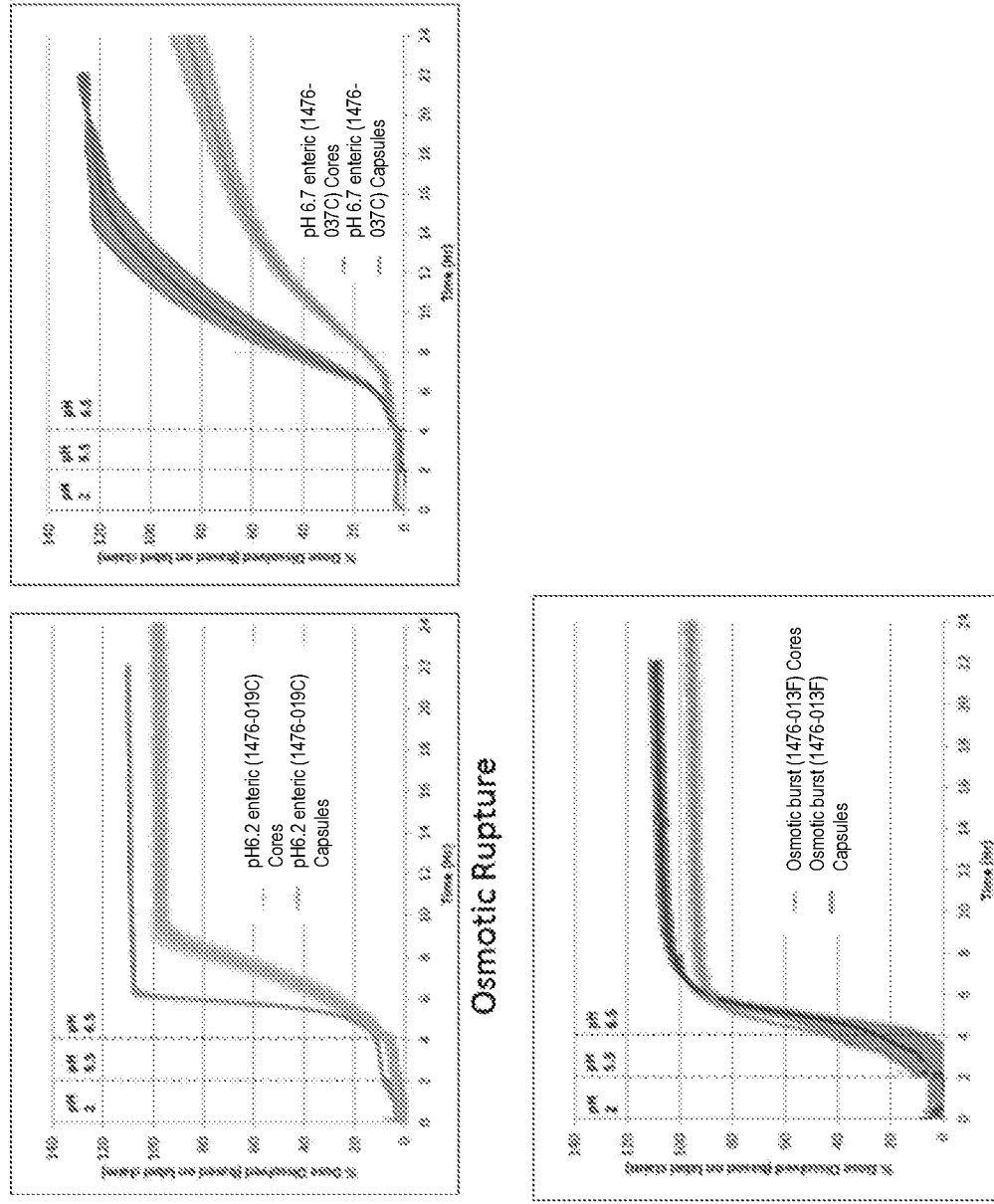

FIG. 23 depicts the capsule vs pellet dissolution profiles for the three SYN-004 formulations. Capsules or pellets (cores) of the three SYN-004 formulations were incubated in 0.01N HCl (pH 2.0) for 2 hours, pH 5.5 for 2 hours, and pH 6.5 for up to 24 hours. Samples were tested for protein concentration by measuring absorbance at 280 nm. The formulations were Enteric pH 6.2, left panel, Enteric pH 6.7, middle panel, and Osmotic, right panel.

Figure 24:
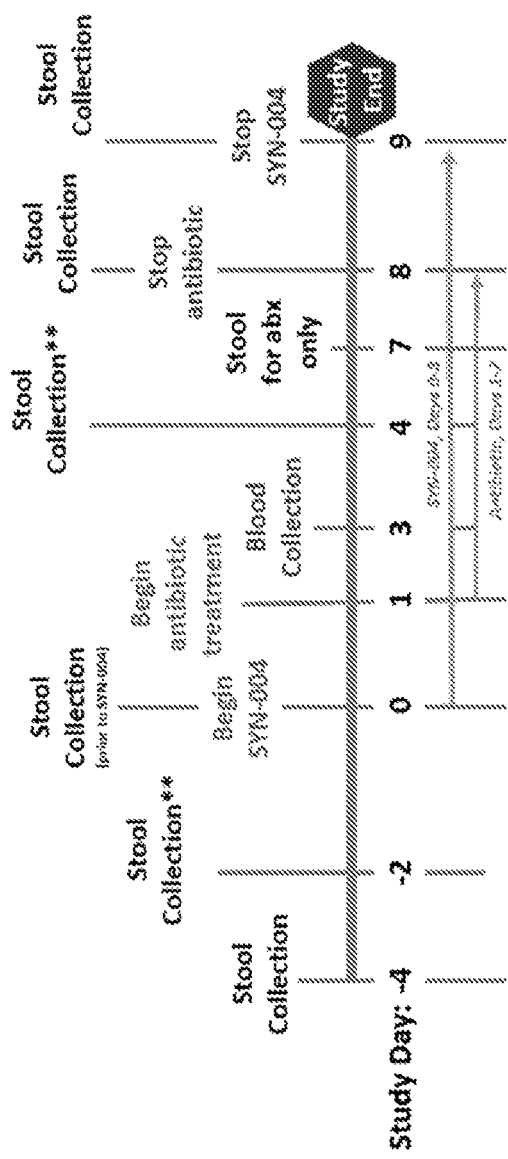

FIG. 24 shows a timeline of piglet dosing. Animals received SYN-004 for 9 days starting on Day 0. Animals received oral amoxicillin for 7 days starting on Day 1. Stool was collected at 5 times, Day −7, Day −4, Day 4, Day 8, and Day 9. Blood was collected at 3 times during Day 2.

Figure 25:
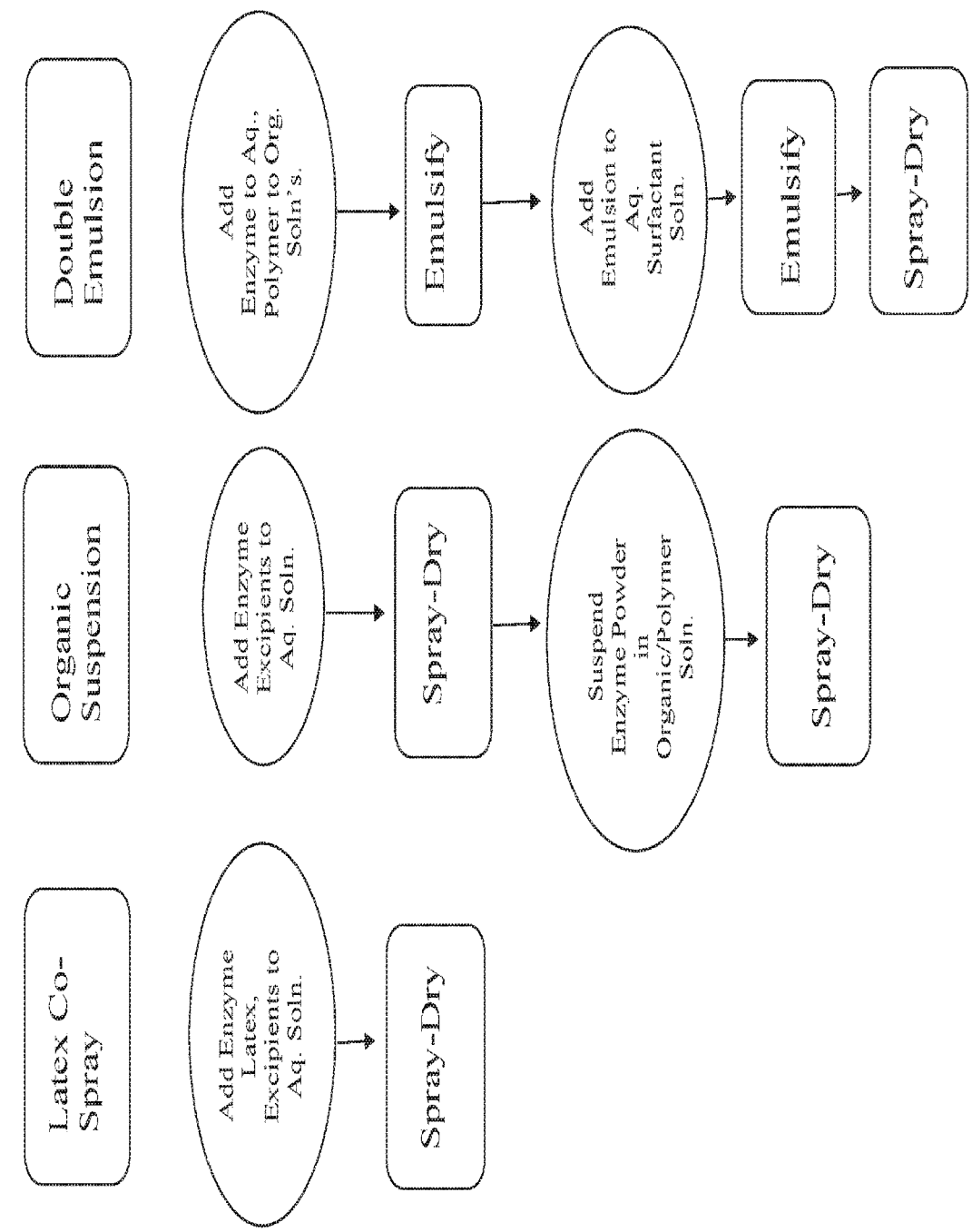

FIG. 25 shows various formulation approaches of the invention.

Figure 26:
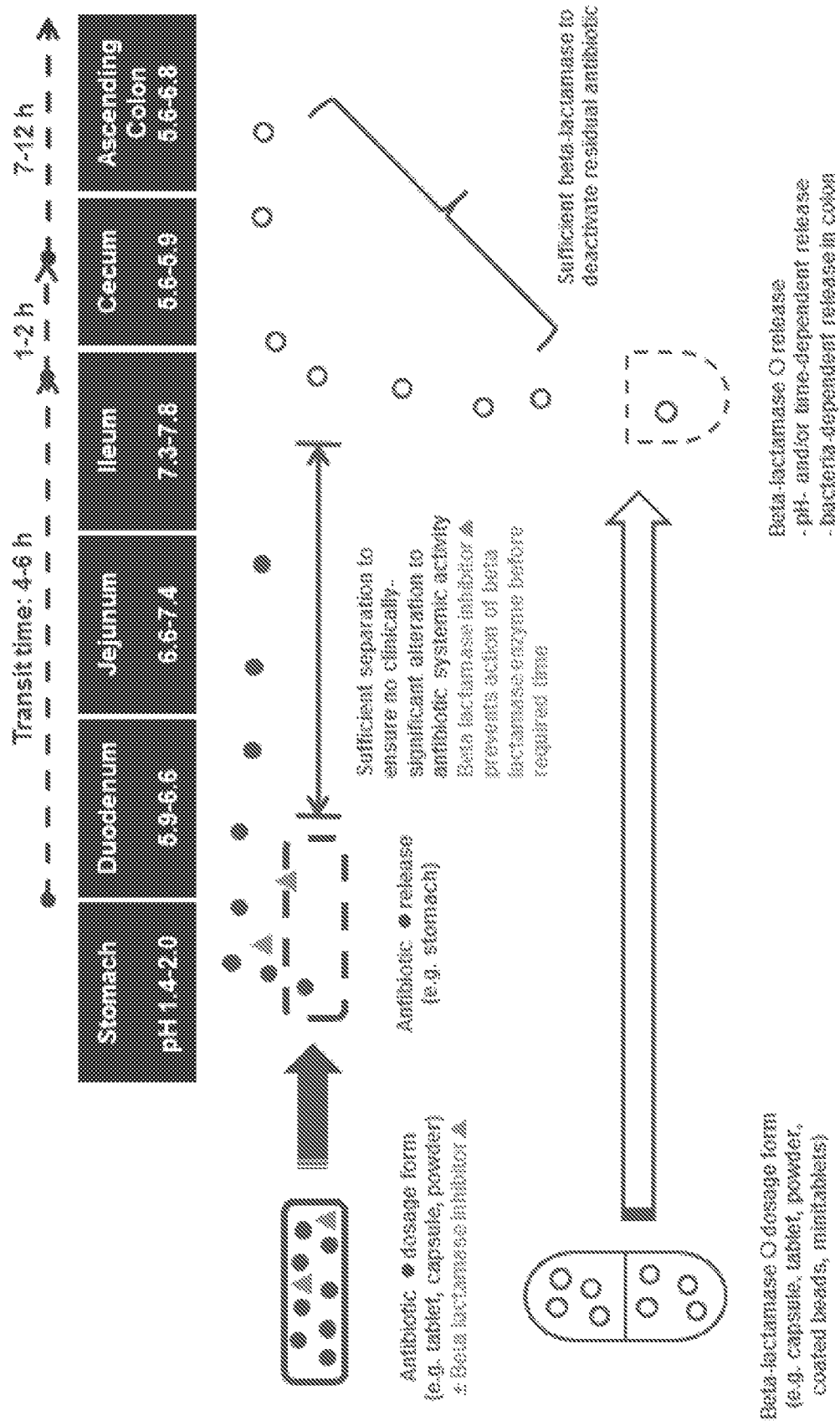

FIG. 26 shows various formulation approaches for segregating antibiotic and/or beta lactamase inhibitor and beta lactamase release.

Figure 27:
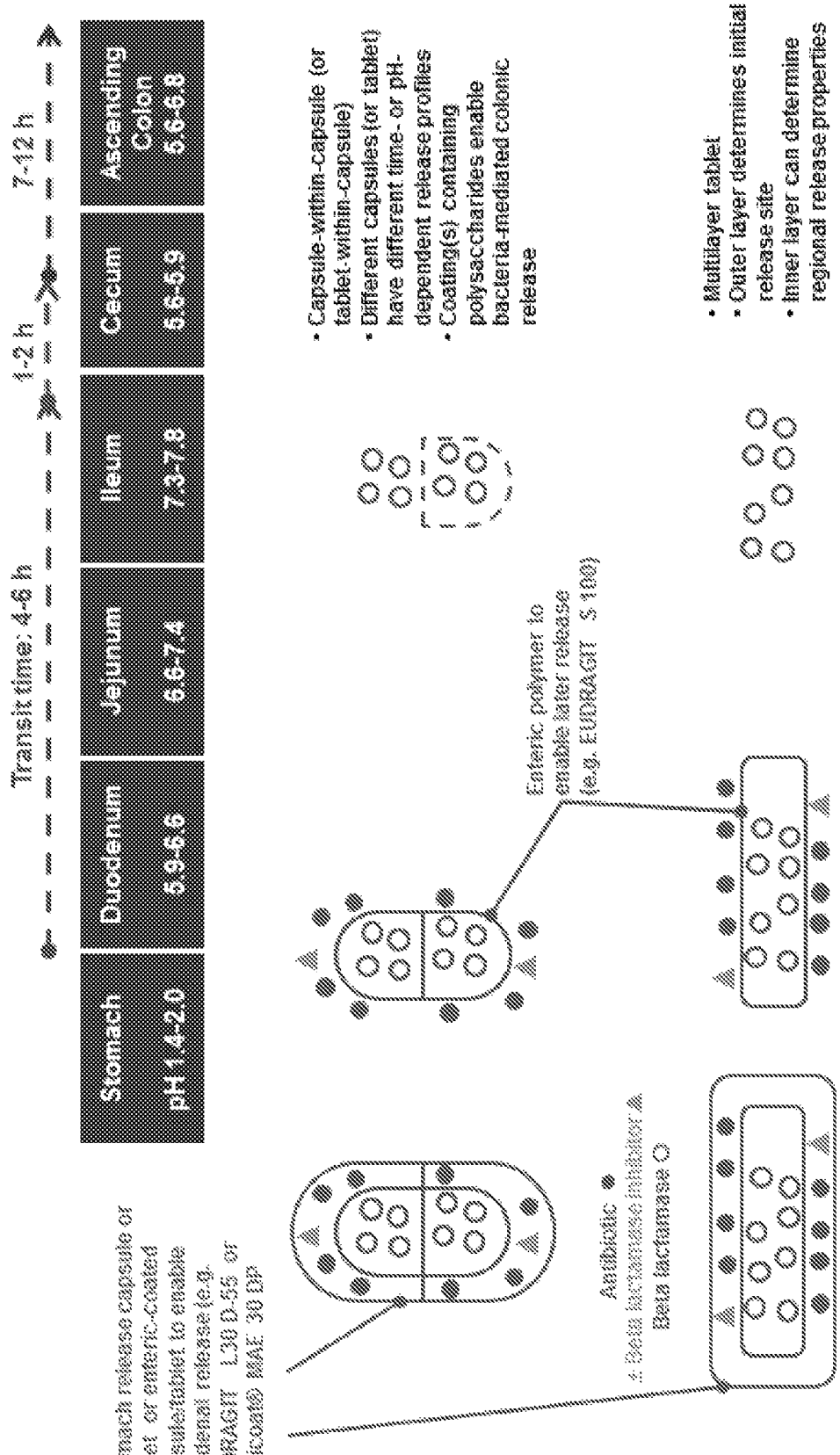

FIG. 27 shows various combination dosage forms.

Figure 28:
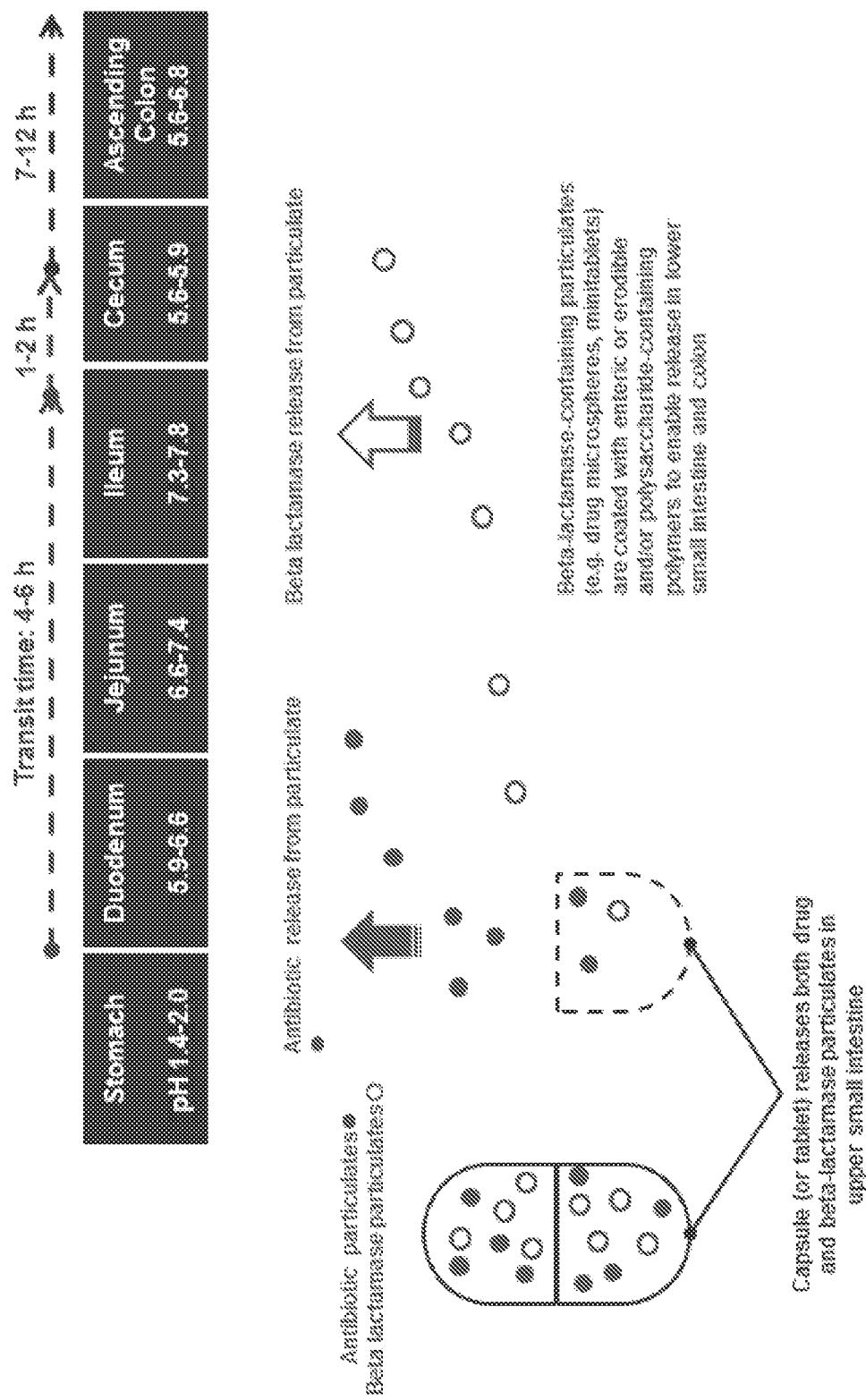

FIG. 28 shows various microparticulate dosage forms.

DETAILED DESCRIPTION

The present invention is based, in part, on the discovery that beta-lactamases can protect the gastrointestinal microbiome of a subject who is undergoing treatment or has undergone treatment with an oral antibiotic. Administration of oral antibiotics often disrupts the ecological balance of normal intestinal microbiota due to residual unabsorbed antibiotics being excreted into the intestines (e.g., the distal small intestine and/or the large intestine). Beta-lactamases inactivate the unabsorbed antibiotics in the GI tract thereby restoring and/or maintaining the normal intestinal microbiota and preventing any overgrowth of potentially pathogenic microorganisms.

In some aspects, the present invention is based, in part, on the discovery that one or more beta-lactamases can be formulated to release in one or more locations within the GI tract at which the beta-lactamase inactivates (e.g. hydrolyzes) an orally delivered beta-lactam antibiotic and, in doing so, protects the microbiome, but the beta-lactamase does not interfere with intestinal absorption of the oral antibiotic and, accordingly, does not interfere with systemic blood or plasma levels of the oral antibiotic. The invention further identifies the location of such beta-lactamase release or activation with preferred locations being in the ileum or cecum. By way of illustration, in some embodiments, the following two approaches may be employed separately or in combination: utilization of formulations designed to release beta-lactamase at the desired location in the GI tract and combining the antibiotic with an oral beta-lactamase inhibitor. In the latter, in some embodiments, the beta-lactamase inhibitor tracks with the beta-lactam antibiotic such that both are available for absorption in the proximal small intestine. The beta-lactamase inhibitor serves to protect the beta-lactam antibiotic from the beta-lactamase in the proximal small intestine. The antibiotic and the inhibitor are then both absorbed into the bloodstream and thereby removed from the proximal small intestine. As the concentration of inhibitor decreases in the small intestine, the beta-lactamase becomes active. Any residual or excess antibiotic that remains in the intestine or reenters with the bile will is inactivated prior to encountering the colonic microbiome.

Beta-Lactamases and Pharmaceutical Compositions

The present invention is directed, in part, to pharmaceutical compositions, formulations, and uses of one or more beta-lactamases. As used herein, a beta-lactamase refers to an enzyme, which deactivates beta-lactams. For example, the beta-lactamase may deactivate a beta-lactam by hydrolysis (e.g. hydrolysis of residual or excess antibiotic). Hydrolysis of the amide bond of the beta-lactam ring by the beta-lactamase makes an antimicrobial agent such as an antibiotic biologically inactive.

In various embodiments, the present invention is directed to compositions including one or more beta-lactamase enzyme of class EC 3.5.2.6. In some embodiments, the beta-lactamase is a group 1, 2, 3, or 4 beta-lactamase, in accordance with the functional classification scheme proposed by Bush et al. (1995, Antimicrob. Agents Chemother. 39: 1211-1233; the entire contents of which are incorporated herein by reference). Without wishing to be bound by theory, Group 1 beta-lactamases include cephalosporinases that are not well inhibited by clavulanic acid; Group 2 includes penicillinases, cephalosporinases and broad-spectrum beta-lactamases that are generally inhibited by active site-directed beta-lactamase inhibitors; Group 3 includes metallo-beta-lactamases that hydrolyze penicillins, cephalosporins and carbapenems, and that are poorly inhibited by almost all beta-lactam-containing molecules; and Group 4 includes penicillinases that are not well inhibited by clavulanic acid.

In some embodiments, the beta-lactamase is a class A, B, C, or D beta-lactamase, in accordance with the Ambler classification which divides beta-lactamases based on their amino acid sequences (Ambler 1980, Philos Trans R Soc Lond B Biol Sci. 289: 321-331; the entire contents of which are incorporated herein by reference). Without wishing to be bound by theory, classes A, C, and D beta-lactamases include evolutionarily distinct groups of serine beta-lactamases, and class B include the zinc-dependent ("EDTA-inhibited") beta-lactamases (see Ambler R. P. et al., 1991, Biochem J. 276: 269-270, the entire contents of which are incorporated herein by reference).

For example, in one embodiment, the beta-lactamase may be a class A enzyme which includes, but is not limited to, for example, KPC-1, KPC-2, KPC-3 and KPC-4. In another embodiment, the beta-lactamase may be a class B enzyme which includes, but is not limited to, for example, the IMP family, VIM family, GIM-1 and SPM-1 as well as others. In another embodiment, the beta-lactamase may be a class C enzyme such as an AmpC beta-lactamase. AmpC beta-lactamases hydrolyze broad and extended-spectrum cephalosporins (i.e., cephamycins and oxyimino-beta-lactams). In a further embodiment, the beta-lactamase may be a class D enzyme that includes, but is not limited to, for example, OXA-23, OXA-24, OXA-25, OXA-26, OXA-27, OXA-40 and OXA-40 as well as others. In some embodiments, the beta-lactamase may be an extended-spectrum beta-lactamase (ESBL), which hydrolyzes cephalosporins with an oxyimino chain. ESBLs include, but are not limited to, TEM, SHV, CTX-M, OXA, PER, VEB, GES, and IBC beta-lactamases. In other embodiments, the beta-lactamase may be an inhibitor-resistant β-lactamase, optionally selected from an AmpC-type β-lactamases, Carbapenemase, IMP-type carbapenemases (metallo-β-lactamases), VIMs (Verona integron-encoded metallo-β-lactamases), OXA (oxacillinase) group of β-lactamases, KPCs (*K. pneumonia* carbapenemases), CMY (Class C), SME, IMI, NMC, CcrA, and NDM (New Delhi metallo-β-lactamases, e.g. NDM-1) beta-lactamases.

In certain embodiments, the beta-lactamase is P1A, P2A, P3A or SYN-004 (synonyms for the same enzyme), or P4A. In an embodiment, the beta-lactamase is P1A or a derivative thereof. The P1A enzyme is a recombinant form of *Bacillus licheniformis* 749/C small exo beta-lactamase (see WO 2008/065247) which belongs to class A and is grouped to subgroup 2a in functional classification. *B. licheniformis* beta-lactamase and its P1A derivative are considered as penicillinases which have high hydrolytic capacity to degrade e.g. penicillin, ampicillin, amoxicillin or piperacillin and they are generally inhibited by active site-directed beta-lactamase inhibitors such as clavulanic acid, sulbactam or tazobactam. In another embodiment, the beta-lactamase is P2A or a derivative thereof as described, for example, in WO 2007/147945, the entire contents of which are incorporated herein by reference. The P2A enzyme belongs to class B and is a metallo-enzyme that requires one or two zinc ions as a cofactor for enzyme activity. In another embodiment, the beta-lactamase is P3A or a derivative thereof as described, for example, in WO 2011/148041 and U.S. Provisional Patent Application Nos. 61/980,844 and 62/046,627, the entire contents of all of which are incorporated herein by reference. In a further embodiment, the beta-lactamase is P4A or a derivative thereof as described, for example, U.S. Provisional Patent Application Nos. 61/980,844 and 62/046,627, the entire contents of all of which are incorporated herein by reference.

For example, the beta-lactamase may have the sequence of *Bacillus licheniformis* PenP, i.e., P1A (SEQ ID NO: 1) or is derived by one or more mutations of SEQ ID NO: 1. Provided herein is the 263 amino acid sequence of P1A (after removal of a 31 amino acid signal sequence and the QASKT (Gln-Ala-Ser-Lys-Thr) pentapeptide at the N-terminus, see SEQ ID NO: 3). As described herein, mutations may be made to this sequence to generate beta-lactamase derivatives.

```
                                               SEQ ID NO: 1
Glu Met Lys Asp Asp Phe Ala Lys Leu Glu Glu Gln

Phe Asp Ala Lys Leu Gly Ile Phe Ala Leu Asp Thr

Gly Thr Asn Arg Thr Val Ala Tyr Arg Pro Asp Glu

Arg Phe Ala Phe Ala Ser Thr Ile Lys Ala Leu Thr

Val Gly Val Leu Leu Gln Gln Lys Ser Ile Glu Asp

Leu Asn Gln Arg Ile Thr Tyr Thr Arg Asp Asp Leu

Val Asn Tyr Asn Pro Ile Thr Glu Lys His Val Asp

Thr Gly Met Thr Leu Lys Glu Leu Ala Asp Ala Ser
```

-continued

```
Leu Arg Tyr Ser Asp Asn Ala Ala Gln Asn Leu Ile

Leu Lys Gln Ile Gly Gly Pro Glu Ser Leu Lys Lys

Glu Leu Arg Lys Ile Gly Asp Glu Val Thr Asn Pro

Glu Arg Phe Glu Pro Glu Leu Asn Glu Val Asn Pro

Gly Glu Thr Gln Asp Thr Ser Thr Ala Arg Ala Leu

Val Thr Ser Leu Arg Ala Phe Ala Leu Glu Asp Lys

Leu Pro Ser Glu Lys Arg Glu Leu Leu Ile Asp Trp

Met Lys Arg Asn Thr Thr Gly Asp Ala Leu Ile Arg

Ala Gly Val Pro Asp Gly Trp Glu Val Ala Asp Lys

Thr Gly Ala Ala Ser Tyr Gly Thr Arg Asn Asp Ile

Ala Ile Ile Trp Pro Pro Lys Gly Asp Pro Val Val

Leu Ala Val Leu Ser Ser Arg Asp Lys Lys Asp Ala

Lys Tyr Asp Asp Lys Leu Ile Ala Glu Ala Thr Lys

Val Val Met Lys Ala Leu Asn Met Asn Gly Lys.
```

In some embodiments, SEQ ID NO: 1 may have a Met and/or Thr preceding the first residue of the sequence. In various embodiments, the Met may be cleaved. As described herein, mutations may be made to the sequence comprising the Met and/or Thr preceding the first residue to generate beta-lactamase derivatives.

Also provided herein is the 299 amino acid sequence of P1A before removal of a 31 amino acid signal sequence and the QASKT (Gln-Ala-Ser-Lys-Thr) pentapeptide at the N-terminus as SEQ ID NO: 3:

```
                                               SEQ ID NO: 3
Met Ile Gln Lys Arg Lys Arg Thr Val Ser Phe Arg

Leu Val Leu Met Cys Thr Leu Leu Phe Val Ser Leu

Pro Ile Thr Lys Thr Ser Ala Gln Ala Ser Lys Thr

Glu Met Lys Asp Asp Phe Ala Lys Leu Glu Glu Gln

Phe Asp Ala Lys Leu Gly Ile Phe Ala Leu Asp Thr

Gly Thr Asn Arg Thr Val Ala Tyr Arg Pro Asp Glu

Arg Phe Ala Phe Ala Ser Thr Ile Lys Ala Leu Thr

Val Gly Val Leu Leu Gln Gln Lys Ser Ile Glu Asp

Leu Asn Gln Arg Ile Thr Tyr Thr Arg Asp Asp Leu

Val Asn Tyr Asn Pro Ile Thr Glu Lys His Val Asp

Thr Gly Met Thr Leu Lys Glu Leu Ala Asp Ala Ser

Leu Arg Tyr Ser Asp Asn Ala Ala Gln Asn Leu Ile

Leu Lys Gln Ile Gly Gly Pro Glu Ser Leu Lys Lys

Glu Leu Arg Lys Ile Gly Asp Glu Val Thr Asn Pro

Glu Arg Phe Glu Pro Glu Leu Asn Glu Val Asn Pro

Gly Glu Thr Gln Asp Thr Ser Thr Ala Arg Ala Leu

Val Thr Ser Leu Arg Ala Phe Ala Leu Glu Asp Lys

Leu Pro Ser Glu Lys Arg Glu Leu Leu Ile Asp Trp

Met Lys Arg Asn Thr Thr Gly Asp Ala Leu Ile Arg
```

```
Ala Gly Val Pro Asp Gly Trp Glu Val Ala Asp Lys

Thr Gly Ala Ala Ser Tyr Gly Thr Arg Asn Asp Ile

Ala Ile Ile Trp Pro Pro Lys Gly Asp Pro Val Val

Leu Ala Val Leu Ser Ser Arg Asp Lys Lys Asp Ala

Lys Tyr Asp Asp Lys Leu Ile Ala Glu Ala Thr Lys

Val Val Met Lys Ala Leu Asn Met Asn Gly Lys
```

Further, the beta-lactamase polypeptide may include additional upstream residues from the first residue of SEQ ID NO: 1 (see, e.g., JBC 258 (18): 11211, 1983, the contents of which are hereby incorporated by reference—including the exo-large and exo-small versions of penP and penP1). Further, the beta-lactamase polypeptide may also include additional downstream residues from the last residue of SEQ ID NO: 1.

The polynucleotide sequence of P1A (after removal of a 31 amino acid signal sequence and the QAKST pentapeptide at the N-terminus) is provided as SEQ ID NO: 2. As described herein, mutations may be made to this sequence to generate the beta-lactamase derivatives (including, taking into account degeneracy of the genetic code).

```
                                            SEQ ID NO: 2
gagatgaaagatgattttgcaaaacttgaggaacaatttgatgcaaaa ctcgggatctttgcattggatacaggtacaaaccggacggtagcgtat cggccggatgagcgttttgcttttgcttcgacgattaaggctttaact gtaggcgtgcttttgcaacagaaatcaatagaagatctgaaccagaga ataacatatacacgtgatgatcttgtaaactacaacccgattacggaa aagcacgttgatacgggaatgacgctcaaagagcttgcggatgcttcg cttcgatatagtgacaatgcggcacagaatctcattcttaaacaaatt ggcggacctgaaagtttgaaaaaggaactgaggaagattggtgatgag gttacaaatcccgaacgattcgaaccagagttaaatgaagtgaatccg ggtgaaactcaggataccagtacagcaagagcacttgtcacaagcctt cgagcctttgctcttgaagataaacttccaagtgaaaaacgcgagctt ttaatcgattggatgaaacgaaataccactggagacgccttaatccgt gccggtgtgccggacggttgggaagtggctgataaaactggagcggca tcatatggaacccggaatgacattgccatcatttggccgccaaaagga gatcctgtcgttcttgcagtattatccagcagggataaaaaggacgcc aagtatgatgataaacttattgcagaggcaacaaggtggtaatgaaa gccttaaacatgaacggcaaataa
```

Also provided is the polynucleotide sequence of P1A before the removal of a 31 amino acid signal sequence and the QASKT pentapeptide at the N-terminus as SEQ ID NO: 4. As described herein, mutations may be made to this sequence to generate beta-lactamase derivatives (including, taking into account degeneracy of the genetic code).

```
                                            SEQ ID NO: 4
atgattcaaaaacgaaagcggacagtttcgttcagacttgtgcttatg tgcacgctgttatttgtcagtttgccgattacaaaaacatcagcgcaa gcttccaagacggagatgaaagatgattttgcaaaacttgaggaacaa tttgatgcaaaactcgggatctttgcattggatacaggtacaaaccgg acggtagcgtatcggccggatgagcgttttgcttttgcttcgacgatt aaggctttaactgtaggcgtgcttttgcaacagaaatcaatagaagat ctgaaccagagaataacatatacacgtgatgatcttgtaaactacaac ccgattacggaaaagcacgttgatacgggaatgacgctcaaagagctt gcggatgcttcgcttcgatatagtgacaatgcggcacagaatctcatt cttaaacaaattggcggacctgaaagtttgaaaaaggaactgaggaag attggtgatgaggttacaaatcccgaacgattcgaaccagagttaaat gaagtgaatccgggtgaaactcaggataccagtacagcaagagcactt gtcacaagccttcgagcctttgctcttgaagataaacttccaagtgaa aaacgcgagcttttaatcgattggatgaaacgaaataccactggagac gccttaatccgtgccggtgtgccggacggttgggaagtggctgataaa actggagcggcatcatatggaacccggaatgacattgccatcatttgg ccgccaaaaggagatcctgtcgttcttgcagtattatccagcagggat aaaaaggacgccaagtatgatgataaacttattgcagaggcaacaaag gtggtaatgaaagccttaaacatgaacggcaaataa
```

In some embodiments, mutagenesis of a beta-lactamase is performed to derive advantageous enzymes to be utilized by methods of the present invention (e.g. those that can target broad spectra of antibiotics). In some embodiments, beta-lactamase derivatives are obtained by site-directed mutagenesis, random mutagenesis, and/or directed evolution approaches. In some embodiments, mutation design is based on, inter alia, structural data (e.g. crystal structure data, homolog models, etc.) of the following: P1A crystal structure (Knox and Moews, J. Mol Biol., 220, 435-455 (1991)), CTX-M-44 (1BZA (Ibuka et al. *Journal of Molecular Biology* Volume 285, Issue 5 2079-2087 (1999), 1IYS (Ibuka et al. Biochemistry, 2003, 42 (36): 10634-43), 1IYO, 1IYP and 1IYQ (Shimamura et al. 2002 J. Biol. Chem. 277:46601-08), *Proteus vulgaris* K1 (1HZO, Nugaka et al. J Mol Biol. 2002 Mar. 15; 317(1):109-17) and *Proteus penneri* HugA (Liassine et al. Antimicrob Agents Chemother. 2002 January; 46(1):216-9. 2002), and reviewed in Bonnet, Antimicrob. Agents Chemother 48(1): 1-14 (2004) (for CTM-X), the contents of all of which are herein incorporated by reference in their entirety). In some embodiments, the present mutations are informed by analysis of structural data (e.g. crystal structure data, homolog models, etc.) of any one of the following beta-lactamases: P1A (see, e.g. U.S. Pat. No. 5,607,671, the contents of which are hereby incorporated by reference), P2A (see, e.g., WO 2007/147945, the contents of which are hereby incorporated by reference), P3A (see, e.g., WO 2011/148041, the contents of which are hereby incorporated by reference), CTX-M-3, CTX-M-4, CTX-M-5, CTX-M-9, CTX-M-10, CTX-M-14, CTX-M-15, CTX-M-16, CTX-M-18, CTX-M-19, CTX-M-25, CTX-M-26, CTX-M-27, CTX-M-32, CTX-M-44, CTX-M-45, and CTX-M-54. Such information is available to one skilled in the art of known databases, for example, Swiss-Prot Protein Sequence Data Bank, NCBI, and PDB.

In some embodiments, the beta-lactamase includes one or more (e.g. about 1, or about 2, or about 3, or about 4, or about 5, or about 6, or about 7, or about 8, or about 9, or about 10, or about 15, or about 20, or about 30, or about 40, or about 50, or about 60, or about 70, or about 80, or about 90, or about 100, or about 110, or about 120, or about 130, or about 140, or about 150) mutations to SEQ ID NO: 1 or SEQ ID NO: 3 or a sequence with at least 30%, 35%, 40%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.8%, or 99.9% identity to SEQ ID NO: 1 or SEQ ID NO: 3 (or about 60%, about 65%, about 70%, about 75%, about 80%, about 85%, about 90%, about 95%, about 96%, about 97%, about 98%, or about 99% identity to SEQ ID NO: 1 or SEQ ID NO: 3).

In various embodiments, one or more amino acid of SEQ ID NO: 1 or SEQ ID NO: 3 is substituted with a naturally occurring amino acid, such as a hydrophilic amino acid (e.g. a polar and positively charged hydrophilic amino acid, such as arginine (R) or lysine (K); a polar and neutral of charge hydrophilic amino acid, such as asparagine (N), glutamine (Q), serine (S), threonine (T), proline (P), and cysteine (C), a polar and negatively charged hydrophilic amino acid, such as aspartate (D) or glutamate (E), or an aromatic, polar and positively charged hydrophilic amino acid, such as histidine (H)) or a hydrophobic amino acid (e.g. a hydrophobic, aliphatic amino acid such as glycine (G), alanine (A), leucine (L), isoleucine (I), methionine (M), or valine (V), a hydrophobic, aromatic amino acid, such as phenylalanine (F), tryptophan (W), or tyrosine (Y) or a non-classical amino acid (e.g. selenocysteine, pyrrolysine, N-formylmethionine β-alanine, GABA and 6-Aminolevulinic acid. 4-Aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general). In some embodiments, SEQ ID NO: 1 may have a Met and/or Thr preceding the first residue of the sequence. These residues may be similarly mutated as above.

Illustrative mutations are described in U.S. Provisional Patent Application Nos. 61/980,844 and 62/046,627, the entire contents of a of which are incorporated herein by reference.

In all of the Class A beta-lactamase mutants, the numbering of residues corresponds to SEQ ID NO: 1. These residue numbers may be converted to Ambler numbers (Ambler et al., 1991, A standard numbering scheme for the Class A β-lactamases, *Biochem. J.* 276:269-272, the contents of which are hereby incorporated by reference) through use of any conventional bioinformatic method, for example by using BLAST (Basic Local Alignment Search Tools) or FASTA (FAST-All). For example, residue 244 corresponds to Ambler 276. For example, the following conversions may be used:

| Ambler Classification No. | SEQ ID NO: 1 Residue |
|---|---|
| F33 | F6 |
| I72 | I44 |
| Q135 | Q105 |
| G156 | G126 |
| T160 | T130 |
| A232 | A202 |
| A237 | A207 |
| A238 | A208 |
| S240 | S209 |
| T243 | T212 |
| R244 | R213 |
| S266 | S234 |
| D276 | D244 |

Furthermore, percent identity may also be assessed with these conventional bioinformatic methods.

In one embodiment, the beta-lactamase utilized by methods of the invention comprises an amino acid sequence having at least 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 1 or SEQ ID NO: 3 and one or more of the following mutations of Ambler classification: F33X, Q135X, G156X, A232X, A237X, A238X, S240X, T243X, R244X, S266X, and D276X, wherein X is any naturally-occurring amino acid and with the proviso that D276X is not present in the context of a single mutant. In some embodiments, X is a naturally occurring hydrophilic or hydrophobic amino acid residue or a non-classical amino acid.

In another embodiment, the beta-lactamase utilized by methods of the invention comprises an amino acid sequence having at least 60% sequence identity with SEQ ID NO: 1 or SEQ ID NO: 3 and one or more of the following mutations of Ambler classification: a hydrophobic residue other than phenylalanine (F) at position 33; a hydrophobic residue other than glutamine (Q) at position 135; a hydrophilic residue other than glycine (G) at position 156; a hydrophobic residue other than alanine (A) at position 232; a hydrophobic residue other than alanine (A) at position 237; a hydrophobic or hydrophilic residue other than alanine (A) at position 238; a hydrophilic residue other than serine (S) at position 240; a hydrophobic residue other than threonine (T) at position 243; a hydrophobic residue other than arginine (R) at position 244; a hydrophilic residue other than serine (S) at position 266; and a hydrophilic residue other than aspartate (D) at position 276, with the proviso that hydrophilic amino acid residue other than aspartic acid (D) at a position corresponding to position 276 is not present in the context of a single mutant.

As used throughout, a hydrophilic amino acid residue may include a polar and positively charged hydrophilic residue selected from arginine (R) and lysine (K), a polar and neutral of charge hydrophilic residue selected from asparagine (N), glutamine (Q), serine (S), threonine (T), proline (P), and cysteine (C), a polar and negatively charged hydrophilic residue selected from aspartate (D) and glutamate (E), or an aromatic, polar and positively charged hydrophilic including histidine (H). As used throughout, a hydrophobic amino acid residue may include a hydrophobic, aliphatic amino acid selected from glycine (G), alanine (A), leucine (L), isoleucine (I), methionine (M), or valine (V) or a hydrophobic, aromatic amino acid selected from phenylalanine (F), tryptophan (W), or tyrosine (Y).

Mutations may be made to the gene sequence of a beta-lactamase (e.g. SEQ ID NOs: 3 and 4) by reference to the genetic code, including taking into account codon degeneracy.

In some embodiments, the beta-lactamase utilized by methods of the invention comprises one or more of the following mutations at positions of Ambler classification: F33Y, Q135M, G156R, A232G, A237S, A238G or T, S240P or D, T243I, R244T, S266N, D276N or R or K, provided that D276N or R or K is not in the context of a single mutant. In one embodiment, the beta-lactamases comprise Q135M. In another embodiment, the beta-lactamases comprise G156R and A238T. In another embodiment, the beta-lactamases comprise F33Y and D276N. In still another embodiment, the beta-lactamases comprise F33Y, S240P, and D276N. In one embodiment, the beta-lactamases comprise F33Y, A238T, and D276N. In another embodiment, the beta-lactamases comprise A232G, A237S, A238G, and S240D. In a further embodiment, the beta-lactamases comprise A232G, A237S, A238G, S240D, and R244T. In another embodiment, the beta-lactamases comprise A232G, A237S, A238G, S240D, and D276R. In one embodiment, the beta-lactamases comprise A232G, A237S, A238G, S240D, and D276K. In one embodiment, the beta-lactamases comprise A232G, A237S, A238G, S240D, and Q135M. In one embodiment, the beta-lactamases comprise A238T. In one embodiment, the beta-lactamases comprise T243I, S266N, and D276N. In one embodiment, the beta-lactamases comprise A232G, A237S, A238G, S240D, and D276N.

In other embodiments, the beta-lactamases comprise an amino acid sequence having at least 60% sequence identity with SEQ ID NO: 1 or SEQ ID NO: 3 and the following of Ambler classification: a hydrophobic residue other than alanine (A) at position 232; a hydrophilic residue other than alanine (A) at position 237; a hydrophobic residue other than alanine (A) at position 238; a hydrophilic residue other than serine (S) at position 240; and a hydrophilic residue other than aspartate (D) at position 276. In some embodiments, the hydrophobic residue other than alanine (A) at position 232 is glycine (G). In some embodiments, the hydrophilic residue other than alanine (A) at position 237 is serine (S). In some embodiments, the hydrophobic residue other than alanine (A) at position 238 is glycine (G). In some embodiments, the hydrophilic residue other than serine (S) at position 240 is aspartate (D). In some embodiments, the other than aspartate (D) at position 276 is asparagine (N). In some embodiments, the beta-lactamase and/or pharmaceutical composition comprises one or more of A232G, A237S, A238G, S240D, and D276N. In some embodiments, the beta-lactamase comprises all of A232G, A237S, A238G, S240D, and D276N, the sequence of which is SEQ ID NO:5:

SEQ ID NO: 5
EMKDDFAKLEEQFDAKLGIFALDTGTNRTVAYRPDERFAFASTIKALT

VGVLLQQKSIEDLNQRITTRDDLVNYNPITEKHVDTGMTLKELADASL

RYSDNAAQNLILKQIGGPESLKKELRKIGDEVTNPERFEPELNEVNPG

ETQDTSTARALVTSLRAFALEDKLPSEKRELLIDWMKRNTTGDALIRA

GVPDGWEVGDKTGSGDYGTRNDIAIIWPPKGDPVVLAVLSSRDKKDAK

YDNKLIAEATKVVMKALNMNGK or

SEQ ID NO: 6 is derived from SEQ ID NO: 5, and further includes the signal and the addition of the QASKT amino acids:

SEQ ID NO: 6
MIQKRKRTVSFRLVLMCTLLFVSLPITKTSAQASKTEMKDDFAKLEEQ

FDAKLGIFALDTGTNRTVAYRPDERFAFASTIKALTVGVLLQQKSIED

LNQRITYTRDDLVNYNPITEKHVDTGMTLKELADASLRYSDNAAQNLI

LKQIGGPESLKKELRKIGDEVTNPERFEPELNEVNPGETQDTSTARAL

VTSLRAFALEDKLPSEKRELLIDWMKRNTTGDALIRAGVPDGWEVGDK

TGSGDYGTRNDIAIIWPPKGDPVVLAVLSSRDKKDAKYDNKLIAEATK

VVMKALNMNGK

An illustrative polynucleotide of the invention is SEQ ID NO: 7:

SEQ ID NO: 7
Atgattcaaaaacgaaagcggacagtttcgttcagacttgtgcttatg tgcacgctgttatttgtcagtttgccgattacaaaaacatcagcgcaa gcttccaagacggagatgaaagatgattttgcaaaacttgaggaacaa tttgatgcaaaactcgggatctttgcattggatacaggtacaaaccgg acggtagcgtatcggccggatgagcgttttgcttttgcttcgacgatt aaggctttaactgtaggcgtgcttttgcaacagaaatcaatagaagat ctgaaccagagaataacatatacacgtgatgatcttgtaaactacaac ccgattacggaaaagcacgttgatacgggaatgacgctcaaagagctt gcggatgcttcgcttcgatatagtgacaatgcggcacagaatctcatt cttaaacaaattggcggacctgaaagtttgaaaaaggaactgaggaag attggtgatgaggttacaaatcccgaacgattcgaaccagagttaaat gaagtgaatccgggtgaaactcaggataccagtacagcaagagcactt gtcacaagccttcgagcctttgctcttgaagataaacttccaagtgaa aaacgcgagcttttaatcgattggatgaaacgaaataccactggagac gccttaatccgtgccggtgtgccggacggttgggaagtgggtgataaa actggaagcggagattatggaacccggaatgacattgccatcatttgg ccgccaaaaggagatcctgtcgttcttgcagtattatccagcagggat aaaaaggacgccaagtatgataataaacttattgcagaggcaacaaag gtggtaatgaaagccttaaacatgaacggcaaataa Full nucleotide sequence of A232G, A237S, A238G, S240D, and D276N mutant, Hind III site (AAGCTT—in bold) and additional K and T amino acids. The leader and additional nucleotides (Hind III site and K and T amino acids—for the addition of the amino acid sequence QASKT) are underlined.

Additional sequences of beta-lactamases including P1A, P2A, P3A, and P4A and derivatives thereof are described for example, in WO2011/148041 and U.S. Provisional Patent Application Nos. 61/980,844 and 62/046,627, the entire contents of all of which are incorporated herein by reference. The following table lists representative beta-lactamases and their derivatives which can be utilized in methods of the present invention:

| Mutations relative to P1A (based on the Ambler classification) | Name |
|---|---|
| Wild type | RS310 (or P1A) |
| D276N | IS118 (or P3A) |
| I72S | IS222 |
| T160F | IS203 |
| R244T | IS217 |
| R244T D276K | IS215 |
| Q135M | IS197 |
| G156R A238T | IS235 |
| F33Y D276N | IS158 |
| F33Y S240P D276N | IS230 (or IS181) |
| F33Y A238T D276N | IS232 (or IS180) |
| I72S Q135M T160F (Block 1 mutants) | IS227 |
| A232G A237S A238G S240D (Block 2 mutants) | IS191 |
| A232G A237S A238G S240D R244T | IS229 |
| A232G A237S A238G S240D D276R | IS219 |
| A232G A237S A238G S240D D276K | IS221 |
| A232G A237S A238G S240D Q135M | IS224 |
| A238T | IS233 |
| T243I S266N D276N | IS234 (or IS176) |
| A232G A237S A238G S240D D276N | IS288 (or P4A) |

In various embodiments, the beta-lactamases possess desirable characteristics, including, for example, having an ability to efficiently target a broad spectra of antibiotics including oral antibiotics. In various embodiments, the beta-lactamases possess desirable enzyme kinetic characteristics. For example, in some embodiments, the beta-lactamases possess a low $K_M$ for at least one oral antibiotic, including, for example, a $K_M$ of less than about 500 μM, or about 100 μM, or about 10 μM, or about 1 μM, or about 0.1 μM (100 nM), or about 0.01 μM (10 nM), or about 1 nM. In various embodiments, the beta-lactamases possess a high $V_{max}$ for at least one oral antibiotic, including, for example, $V_{max}$ which is greater than about 100 s-1, or about 1000 s-1, or about 10000 s-1, or about 100000 s-1, or about 1000000 s-1. In various embodiments, the beta-lactamases possess catalytic efficiency that is greater than about $10^6 M^{-1} s^{-1}$ for at least one oral antibiotic.

In various embodiments, the beta-lactamases are stable and/or active in the GI tract, e.g. in one or more of the mouth, esophagus, stomach, duodenum, small intestine, duodenum, jejunum, ileum, large intestine, colon transversum, colon descendens, colon ascendens, colon sigmoidenum, cecum, and rectum. In a specific embodiment, the beta-lactamase is stable in the large intestine, optionally selected from one or more of colon transversum, colon descendens, colon ascendens, colon sigmoidenum and cecum. In a specific embodiment, the beta-lactamase is stable in the small intestine, optionally selected from one or more of duodenum, jejunum, and ileum. In some embodiments, the beta-lactamase is resistant to proteases in the GI tract, including for example, the small intestine. In some embodiments, the beta-lactamase is substantially active at a pH of about 6.0 to about 7.5, e.g. about 6.0, or about 6.1, or about 6.2, or about 6.3, or about 6.4, or about 6.5, or about 6.6, or about 6.7, or about 6.8, or about 6.9, or about 7.0, or about 7.1, or about 7.2, or about 7.3, or about 7.4, or about 7.5 (including, for example, via formulation, as described herein). In various embodiments, the beta-lactamases of the present invention are resistant to one or more beta-lactamase inhibitors, optionally selected from avibactam, tazobactam, sulbactam, and clavulanic acid. In other embodiments, as described herein the beta-lactamases of the present invention are susceptible to one or more beta-lactamase inhibitors and this property is exploited to ensure antibiotic hydrolysis does not interfere with the therapeutic benefit of the oral antibiotic. In some embodiments, stable refers to an enzyme that has a long enough half-life and maintains sufficient activity for therapeutic effectiveness.

In some embodiments, the beta-lactamases described herein, include derivatives that are modified, i.e., by the covalent attachment of any type of molecule to the beta-lactamase such that covalent attachment does not prevent the activity of the enzyme. For example, but not by way of limitation, derivatives include beta-lactamases that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out, including, but not limited to specific chemical cleavage, acetylation, formylation, metabolic synthesis of tunicamycin, etc. Additionally, the derivative can contain one or more non-classical amino acids.

In still other embodiments, the beta-lactamases described herein may be modified to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

The beta-lactamases described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the beta-lactamases having an acidic functional group, such as a carboxylic acid functional group, and a base. Suitable bases include, but are not limited to, hydroxides of alkali metals such as sodium, potassium, and lithium;

hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

In some embodiments, the compositions described herein are in the form of a pharmaceutically acceptable salt.

Further, any beta-lactamases described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, cellulose, hypromellose, lactose, sucrose, malt, rice, flour, chalk, silica gel, sodium stearate, glycerol monostearate, talc, sodium chloride, dried skim milk, glycerol, propylene, glycol, povidone, crosspovidone, water, ethanol and the like. Any agent described herein, if desired, can also comprise minor amounts of wetting or emulsifying agents, or pH buffering agents. Other examples of suitable pharmaceutical excipients are described in Remington's Pharmaceutical Sciences 1447-1676 (Alfonso R. Gennaro eds., 19th ed. 1995), incorporated herein by reference.

Where necessary, the beta-lactamases and/or pharmaceutical compositions (and/or additional therapeutic agents) can include a solubilizing agent. Also, the agents can be delivered with a suitable vehicle or delivery device. Compositions for administration can optionally include a local anesthetic such as, for example, lignocaine to lessen pain at the site of the injection. Combination therapies outlined herein can be co-delivered in a single delivery vehicle or delivery device.

Oral Antibiotics

In various embodiments, the beta-lactamases deactivate one or more oral antibiotics. In various embodiments, the beta-lactamases hydrolyze one or more oral antibiotics. In various embodiments, the described beta-lactamases and/or pharmaceutical compositions (and/or additional therapeutic agents) are formulated in a manner that preserves the therapeutic (e.g. systemic) action of one or more oral antibiotics while preventing the action of excess amounts these oral antibiotics lower in the GI tract, where they may disrupt the GI microbiota.

For example, the described beta-lactamases and/or pharmaceutical compositions (and/or additional therapeutic agents) are formulated in a manner that active antibiotic that is not absorbed from the GI tract after an oral dose or is returned in active form to the intestinal tract from the systemic circulation is deactivated. In certain embodiments, the orally administered antibiotics are selected from penicillins, cephalosporins, monobactams, and carbapenems.

Penicillins include, for example, Amdinocillin, Amoxicillin (e.g. NOVAMOX, AMOXIL); Ampicillin (e.g. PRINCIPEN); Azlocillin; Carbenicillin (e.g. GEOCILLIN); Cloxacillin (e.g. TEGOPEN); Cyclacillin, Dicloxacillin (e.g. DYNAPEN); Flucloxacillin (e.g. FLOXAPEN); Mezlocillin (e.g. MEZLIN); Methicillin (e.g. STAPHCILLIN); Nafcillin (e.g. UNIPEN); Oxacillin (e.g. PROSTAPHLIN); Penicillanic Acid, Penicillin G (e.g. PENTIDS or PFIZERPEN); Penicillin V (e.g. VEETIDS (PEN-VEE-K)); Piperacillin (e.g. PIPRACIL); Sulbactam, Temocillin (e.g. NEGABAN); and Ticarcillin (e.g. TICAR).

Illustrative penicillins include:

| Generic | Brand Name |
| --- | --- |
| Amoxicillin | AMOXIL, POLYMOX, TRIMOX, WYMOX |
| Ampicillin | OMNIPEN, POLYCILLIN, POLYCILLIN-N, PRINCIPEN, TOTACILLIN |
| Bacampicillin | SPECTROBID |
| Carbenicillin | GEOCILLIN, GEOPEN |
| Cloxacillin | CLOXAPEN |
| Dicloxacillin | DYNAPEN, DYCILL, PATHOCIL |
| Flucloxacillin | FLOPEN, FLOXAPEN, STAPHCILLIN |
| Mezlocillin | MEZLIN |
| Nafcillin | NAFCIL, NALLPEN, UNIPEN |
| Oxacillin | BACTOCILL, PROSTAPHLIN |
| Penicillin G | BICILLIN L-A, CRYSTICILLIN 300 A.S., PENTIDS, PERMAPEN, PFIZERPEN, PFIZERPEN-AS, WYCILLIN |
| Penicillin V | BEEPEN-VK, BETAPEN-VK, LEDERCILLIN VK, V-CILLIN K |
| Piperacillin | PIPRACIL |
| Pivampicillin | |
| Pivmecillinam | |
| Ticarcillin | TICAR |

Cephalosporins include, for example, a first generation cephalosporin (e.g. Cefadroxil (e.g. DURICEF); Cefazolin (e.g. ANCEF); Ceftolozane, Cefalotin/Cefalothin (e.g. KEFLIN); Cefalexin (e.g. KEFLEX); a second generation cephalosporin (e.g. Cefaclor (e.g. DISTACLOR); Cefamandole (e.g. MANDOL); Cefoxitin (e.g. MEFOXIN); Cefprozil (e.g. CEFZIL); Cefuroxime (e.g. CEFTIN, ZINNAT)); a third generation cephalosporin (e.g. Cefixime (e.g. SUPRAX); Cefdinir (e.g. OMNICEF, CEFDIEL); Cefditoren (e.g. SPECTRACEF); Cefoperazone (e.g. CEFOBID); Cefotaxime (e.g. CLAFORAN); Cefpodoxime (e.g. VANTIN); Ceftazidime (e.g. FORTAZ); Ceftibuten (e.g. CEDAX) Ceftizoxime (e.g. CEFIZOX); and Ceftriaxone (e.g. ROCEPHIN)); a fourth generation cephalosporin (e.g. Cefepime (e.g. MAXIPIME)); or a fifth generation cephalosporin (e.g. Ceftaroline fosamil (e.g. TEFLARO); Ceftobiprole (e.g. ZEFTERA)). Also included is Latamoxef (or moxalactam). In a specific embodiment, cephalosporins include, for example, cefoperazone, ceftriaxone or cefazolin.

Illustrative cephalosporins include

| Generic | Brand Name |
|---|---|
| First Generation | |
| Cefacetrile (cephacetrile) | CELOSPOR, CELTOL, CRISTACEF |
| Cefadroxil (cefadroxyl) | DURICEF, ULTRACEF |
| Cefalexin (cephalexin) | KEFLEX, KEFTAB |
| Cefaloglycin (cephaloglycin) | KEFGLYCIN |
| Cefalonium (cephalonium) | |
| Cefaloridine (cephaloradine) | |
| Cefalotin (cephalothin) | KEFLIN |
| Cefapirin (cephapirin) | CEFADYL |
| Cefatrizine | |
| Cefazaflur | |
| Cefazedone | |
| Cefazolin (cephazolin) | ANCEF, KEFZOL |
| Cefradine (cephradine) | VELOSEF |
| Cefroxadine | |
| Ceftezole | |
| Second Generation | |
| Cefaclor | CECLOR, CECLOR CD, DISTACLOR, KEFLOR, RANICOR |
| Cefamandole | MANDOL |
| Cefmetazole | |
| Cefonicid | MONOCID |
| Cefotetan | CEFOTAN |
| Cefoxitin | MEFOXIN |
| Cefprozil (cefproxil) | CEFZIL |
| Cefuroxime | CEFTIN, KEFUROX, ZINACEF, ZINNAT |
| Cefuzonam | |
| Third Generation | |
| Cefcapene | |
| Cefdaloxime | |
| Cefdinir | OMNICEF, CEFDIEL |
| Cefditoren | SPECTRACEF |
| Cefetamet | |
| Cefixime | SUPRAX |
| Cefmenoxime | CEFMAX |
| Cefodizime | |
| Cefotaxime | CLAFORAN |
| Cefpimizole | |
| Cefpodoxime | VANTIN |
| Cefteram | |
| Ceftibuten | CEDAX |
| Ceftiofur | EXCEDE |
| Ceftiolene | |
| Ceftizoxime | CEFIZOX |
| Ceftriaxone | ROCEPHIN |
| Cefoperazone | CEFOBID |
| Ceftazidime | CEPTAZ, FORTUM, FORTAZ, TAZICEF, TAZIDIME |
| Fourth Generation | |
| Cefclidine | |
| Cefepime | MAXIPIME |
| Cefluprenam | |
| Cefoselis | |
| Cefozopran | |
| Cefpirome | CEFROM |
| Cefquinome | |
| Fifth Generation | |
| Ceftobiprole | ZEFTERA |
| Ceftaroline | TEFLARO |
| Not Classified | |
| Cefaclomezine | |
| Cefaloram | |
| Cefaparole | |
| Cefcanel | |
| Cefedrolor | |
| Cefempidone | |
| Cefetrizole | |
| Cefivitril | |
| Cefmatilen | |
| Cefmepidium | |
| Cefovecin | |
| Cefoxazole | |
| Cefrotil | |
| Cefsumide | |
| Cefuracetime | |
| Ceftioxide | |

Monobactams include, for example, aztreonam (e.g. AZACTAM, CAYSTON), tigemonam, nocardicin A, and tabtoxin.

Carbapenems include, for example, meropenem, imipenem (by way of non-limiting example, imipenem/cilastatin), ertapenem, doripenem, panipenem/betamipron, biapenem, razupenem (PZ-601), tebipenem, lenapenem, and tomopenem. Carbapenems also include thienamycins.

Illustrative carbapenems include

| Generic | Brand Name |
|---|---|
| Imipenem, Imipenem/cilastatin | PRIMAXIN |
| Doripenem | DORIBAX |
| Meropenem | MERREM |
| Ertapenem | INVANZ |

Beta-Lactamase Inhibitors

In various embodiments, the described beta-lactamases and/or pharmaceutical compositions (and/or additional therapeutic agents) are formulated in a manner that preserves the therapeutic (e.g. systemic) action of one or more oral antibiotics while preventing the action of residual or excess amounts these oral antibiotics (e.g. active antibiotic that is not absorbed from the GI tract after an oral dose or is returned in active form to the intestinal tract from the systemic circulation) lower in the GI tract, where they may disrupt the GI microbiota and this dual purpose is effected, in part, by use of one or more beta-lactamase inhibitor.

For example, the described beta-lactamases may be administered in a patient that receives one or more beta-lactamase inhibitors (e.g. sequential or simultaneous co-administration, or co-formulation) such that the one or more beta-lactamase inhibitors act to protect the oral antibiotics higher in the GI tract (e.g. ileum and above, or the proximal small intestine) by reducing or eliminating beta-lactamase activity. However, the one or more beta-lactamase inhibitors do not have such inhibitory effects on beta-lactamase activity lower in the GI tract (e.g. distal small intestine and/or the colon) and therefore allow the described beta-lactamase to deactivate (e.g. hydrolyze) residual or excess oral antibiotic lower in the GI tract and thus prevent or mitigate damage to the GI microbiota.

In some embodiments, the beta-lactamase inhibitor tracks with the beta-lactam antibiotic such that both are available for absorption in the proximal small intestine. The beta-lactamase inhibitor serves to protect the beta-lactam antibiotic from the beta-lactamase in the proximal small intestine. The antibiotic and the inhibitor are then both absorbed into the bloodstream and thereby removed from the proximal small intestine. As the concentration of inhibitor decreases in the small intestine, the beta-lactamase becomes active. Any residual or excess antibiotic that remains in the intestine or re-enters with the bile will is inactivated prior to encountering the colonic microbiome.

In some embodiments, the beta-lactamase inhibitor includes, for example, tazobactam, sulbactam, clavulanic acid, avibactam, monobactam derivatives, ATMO derivatives, penems (e.g., BRL42715 and derivatives thereof, Syn1012, oxapenems, trinems, 1-(3-methylcarbapenems), penicillin and cephalosporin sulfone derivatives (e.g., 0-2/C-3-substituted penicillin and cephalosporin sulfones, C-6-substituted penicillin sulfones), non-6-lactam inhibitors (e.g., boronic acid transition state analogs, phophonates, NXL104, hydroxmates) and metallo-6-lactamase inhibitors such as thiol derivatives, pyridine dicarboxylates, trifluoromethyl ketones and alcohols, carbapenem analogs, tricyclic natural products, succinate derivatives, and C-6-mercaptomethyl penicillinates. Co-formulations of an oral antibiotic with one or more beta-lactamase inhibitors are also provided in some embodiments (e.g. Augmentin is a mixture of amoxicillin and clavulanic acid; Sultamicillin is a mixture of ampicillin and sulbactam).

Further, any of the beta-lactamase inhibitors described in Drawz, Clin Microbiol Rev. January 2010; 23(1): 160-201, the contents of which are hereby incorporated by reference in their entirety, are encompassed by the present invention.

Formulations and Administration

The present invention includes the described beta-lactamases and/or pharmaceutical compositions (and/or additional therapeutic agents) in various formulations. Any beta-lactamase and/or pharmaceutical composition (and/or additional therapeutic agents) described herein can take the form of solutions, suspensions, emulsion, drops, tablets, pills, pellets, capsules, capsules containing liquids, capsules containing multiparticulates, powders, suppositories, emulsions, aerosols, sprays, suspensions, delayed-release formulations, sustained-release formulations, controlled-release formulations, or any other form suitable for use. In one embodiment, the composition is in the form of a capsule or a tablet (see, e.g., U.S. Pat. No. 5,698,155).

The formulations comprising the beta-lactamases and/or pharmaceutical compositions (and/or additional therapeutic agents) may conveniently be presented in unit dosage forms. For example, the dosage forms may be prepared by methods which include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by press tableting)

In one embodiment, the beta-lactamases (and/or additional therapeutic agents) described herein is formulated as a composition adapted for a mode of administration described herein.

In some embodiments, the administration the beta-lactamases and/or pharmaceutical compositions (and/or additional therapeutic agents) is any one of oral, intravenous, and parenteral. In some embodiments, the administration of the beta-lactamases and/or pharmaceutical compositions (and/or additional therapeutic agents) is not intravenous in order to, for example, prevent interference with an antibiotic administered systemically. In other embodiments, routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically, particularly to the ears, nose, eyes, or skin. In some embodiments, the administering is effected orally or by parenteral injection.

In various embodiments, the administration the beta-lactamases and/or pharmaceutical compositions (and/or additional therapeutic agents) is into the GI tract via, for example, oral delivery, nasogastral tube, intestinal intubation (e.g. an enteral tube or feeding tube such as, for example, a jejunal tube or gastro-jejunal tube, etc.), endoscopy, colonoscopy, or enema.

In an embodiment, the beta-lactamases and/or pharmaceutical compositions (and/or additional therapeutic agents) described herein can be administered orally. In other embodiments, the beta-lactamases and/or pharmaceutical compositions (and/or additional therapeutic agents) can also be administered by any other convenient route, for example, by intravenous infusion or bolus injection, by absorption through epithelial or mucocutaneous linings (e.g., oral mucosa, rectal and intestinal mucosa, etc.) and can be administered together with an additional therapeutic agent. Administration can be systemic or local. In some embodiments, administration is not at the site of infection to avoid, for example, hydrolysis of an antibiotic at the site of infection. Various delivery systems are known, e.g., encapsulation in liposomes, microparticles, microcapsules, capsules, etc., and can be used for administration.

In specific embodiments, it may be desirable to administer locally to the area in need of treatment.

In one embodiment, the beta-lactamases and/or pharmaceutical compositions (and/or additional therapeutic agents) described herein is formulated as a composition adapted for oral administration to humans. Compositions for oral delivery can be in the form of tablets, lozenges, aqueous or oily suspensions, granules, powders, sprinkles, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration to provide a sustained action over an extended period of time. Selectively permeable membranes surrounding an osmotically active agent driving any beta-lactamases (and/or additional therapeutic agents) described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, ethacrylic acid and derivative polymers thereof, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

In various embodiments, the beta-lactamases and/or pharmaceutical compositions (and/or additional therapeutic agent) are formulated as solid dosage forms such as tablets, dispersible powders, granules, and capsules. In one embodiment, the beta-lactamases and/or pharmaceutical compositions (and/or additional therapeutic agent) are formulated as a capsule. In another embodiment, the beta-lactamases and/or pharmaceutical compositions (and/or additional therapeutic agent) are formulated as a tablet. In yet another embodiment, the beta-lactamases and/or pharmaceutical compositions (and/or additional therapeutic agent) are formulated as a soft-gel capsule. In a further embodiment, the beta-lactamases and/or pharmaceutical compositions (and/or additional therapeutic agent) are formulated as a gelatin capsule.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents.

Various methods may be used to formulate and/or deliver the agents described herein to a location of interest. For example, the beta-lactamases and/or pharmaceutical compositions (and/or additional therapeutic agents) described herein may be formulated for delivery to the gastrointestinal tract. The gastrointestinal tract includes organs of the digestive system such as mouth, esophagus, stomach, duodenum, small intestine, large intestine and rectum and includes all subsections thereof (e.g. the small intestine may include the duodenum, jejunum and ileum; the large intestine may include the colon transversum, colon descendens, colon ascendens, colon sigmoidenum and cecum). For example, the beta-lactamases and/or pharmaceutical compositions (and/or additional therapeutic agents) described herein may be formulated for delivery to one or more of the stomach, small intestine, large intestine and rectum and includes all subsections thereof (e.g. duodenum, jejunum and ileum, colon transversum, colon descendens, colon ascendens, colon sigmoidenum and cecum). In some embodiments, the compositions described herein may be formulated to deliver to the upper or lower GI tract. In an embodiment, the beta-lactamases and/or pharmaceutical compositions (and/or additional therapeutic agents) may be administered to a subject, by, for example, directly or indirectly contacting the mucosal tissues of the gastrointestinal tract.

For example, in various embodiments, the present invention provides modified release formulations comprising at least one beta-lactamase (and/or additional therapeutic agents), wherein the formulation releases a substantial amount of the beta-lactamase (and/or additional therapeutic agents) into one or more regions of the GI tract. For example, the formulation may release at least about 60% of the beta-lactamase after the stomach and into one or more regions of the GI tract. In various embodiments, the modified release formulations comprising at least one beta-lactamase (and/or additional therapeutic agents) are released in a manner that allows for the therapeutic (e.g. systemic) activity of one or more oral antibiotic (and/or a beta-lactamase inhibitor) but prevents or mitigates the deleterious effects of residual or excess oral antibiotics on the microbiota of the GI tract (e.g. active antibiotic that is not absorbed from the GI tract after an oral dose or is returned in active form to the intestinal tract from the systemic circulation). In various embodiments, the modified release formulations comprising at least one beta-lactamase (and/or additional therapeutic agents) are released distal to the release of one or more oral antibiotic (and/or a beta-lactamase inhibitor). For example, in various embodiments, the modified release formulations comprising at least one beta-lactamase (and/or additional therapeutic agents) are released distal to the ileum and below. For example, in various embodiments, the modified release formulations comprising at least one beta-lactamase (and/or additional therapeutic agents) are released is released in the distal small intestine and/or the colon.

In various embodiments, the modified-release formulation of the present invention releases at least 60% of the beta-lactamase (or additional therapeutic agents) after the stomach into one or more regions of the intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the intestine.

In various embodiments, the modified-release formulation of the present invention releases at least 60% of the beta-lactamase (or additional therapeutic agents) in the small intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the small intestine.

In one embodiment, the modified-release formulation of the present invention releases at least 60% of the beta-lactamase (or additional therapeutic agents) in the duodenum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the duodenum.

In one embodiment, the modified-release formulation of the present invention releases at least 60% of the beta-lactamase (or additional therapeutic agents) in the jejunum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the jejunum.

In one embodiment, the modified-release formulation of the present invention releases at least 60% of the beta-lactamase (or additional therapeutic agents) in the ileum and/or the ileocecal junction. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the ileum and/or the ileocecal junction.

In various embodiments, the modified-release formulation of the present invention releases at least 60% of the beta-lactamase (or additional therapeutic agents) in the large intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the large intestine.

In one embodiment, the modified-release formulation of the present invention releases at least 60% of the beta-lactamase (or additional therapeutic agents) in the cecum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the cecum.

In one embodiment, the modified-release formulation of the present invention releases at least 60% of the beta-lactamase (or additional therapeutic agents) in the ascending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the ascending colon.

In one embodiment, the modified-release formulation of the present invention releases at least 60% of the beta-lactamase (or additional therapeutic agents) in the transverse colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the transverse colon.

In one embodiment, the modified-release formulation of the present invention releases at least 60% of the beta-lactamase (or additional therapeutic agents) in the descending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the descending colon.

In one embodiment, the modified-release formulation of the present invention releases at least 60% of the beta-lactamase (or additional therapeutic agents) in the sigmoid colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the sigmoid colon.

In various embodiments, the modified-release formulation does not substantially release the beta-lactamase (or additional therapeutic agents) in the stomach.

In certain embodiments, the modified-release formulation releases the beta-lactamase (or additional therapeutic agents) at a specific pH. For example, in some embodiments, the modified-release formulation is substantially stable in an acidic environment and substantially unstable (e.g., dissolves rapidly or is physically unstable) in a near neutral to alkaline environment. In some embodiments, stability is indicative of not substantially releasing while instability is indicative of substantially releasing. For example, in some embodiments, the modified-release formulation is substantially stable at a pH of about 7.0 or less, or about 6.7 or less, or about 6.5 or less, or about 6.2 or less or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. In some embodiments, the present formulations are stable in lower pH areas and therefore do not substantially release in, for example, the stomach. In some embodiments, modified-release formulation is substantially stable at a pH of about 1 to about 4 or lower and substantially unstable at pH values that are greater. In these embodiments, the modified-release formulation is not substantially released in the stomach. In these embodiments, the modified-release formulation is substantially released in the small intestine (e.g. one or more of the duodenum, jejunum, and ileum) and/or large intestine (e.g. one or more of the cecum, ascending colon, transverse colon, descending colon, and sigmoid colon). In some embodiments, modified-release formulation is substantially stable at a pH of about 4 to about 5 or lower and consequentially is substantially unstable at pH values that are greater and therefore is not substantially released in the stomach and/or small intestine (e.g. one or more of the duodenum, jejunum, and ileum). In these embodiments, the modified-release formulation is substantially released in the large intestine (e.g. one or more of the cecum, ascending colon, transverse colon, descending colon, and sigmoid colon). In an embodiment, the modified-release formulation is substantially unstable at a pH of greater than about 6.2. In another embodiment, the modified-release formulation is substantially unstable at a pH of greater than about 6.7. In various embodiments, the pH values recited herein may be adjusted as known in the art to account for the state of the subject, e.g. whether in a fasting or postprandial state.

In some embodiments, the modified-release formulation is substantially stable in gastric fluid and substantially unstable in intestinal fluid and, accordingly, is substantially released in the small intestine (e.g. one or more of the duodenum, jejunum, and ileum) and/or large intestine (e.g. one or more of the cecum, ascending colon, transverse colon, descending colon, and sigmoid colon).

In some embodiments, the modified-release formulation is stable in gastric fluid or stable in acidic environments. These modified-release formulations release about 30% or less by weight of the beta-lactamase and/or additional therapeutic agent in the modified-release formulation in gastric fluid with a pH of about 4 to about 5 or less, or simulated gastric fluid with a pH of about 4 to about 5 or less, in about 15, or about 30, or about 45, or about 60, or about 90 minutes. Modified-release formulations of the of the invention may release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of the beta-lactamase and/or additional therapeutic agent in the modified-release formulation in gastric fluid with a pH of 4-5, or less or simulated gastric fluid with a pH of 4-5 or less, in about 15, or about 30, or about 45, or about 60, or about 90 minutes. Modified-release formulations of the invention may release about 1%, about 2%, about 3%, about 4%, about 5%, about 6%, about 7%, about 8%, about 9%, or about 10% by weight of the total beta-lactamase and/or additional therapeutic agent in the modified-release formulation in gastric fluid with a pH of 5 or less, or simulated gastric fluid with a pH of 5 or less, in about 15, or about 30, or about 45, or about 60, or about 90 minutes.

In some embodiments, the modified-release formulation is unstable in intestinal fluid. These modified-release formulations release about 70% or more by weight of the beta-lactamase and/or additional therapeutic agent in the modified-release formulation in intestinal fluid or simulated intestinal fluid in about 15, or about 30, or about 45, or about 60, or about 90 minutes. In some embodiments, the modified-release formulation is unstable in near neutral to alkaline environments. These modified-release formulations release about 70% or more by weight of the beta-lactamase and/or additional therapeutic agent in the modified-release formulation in intestinal fluid with a pH of about 4-5 or greater, or simulated intestinal fluid with a pH of about 4-5 or greater, in about 15, or about 30, or about 45, or about 60, or about 90 minutes. A modified-release formulation that is unstable in near neutral or alkaline environments may release 70% or more by weight of beta-lactamase and/or additional therapeutic agent in the modified-release formulation in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

In various embodiments, the modified-release formulations comprising a beta-lactamase are substantially stable in chyme. For example, there is, in some embodiments, a loss of less than about 50% or about 40%, or about 30%, or about 20%, or about 10% of beta-lactamase activity in about 10, or 9, or 8, or 7, or 6, or 5, or 4, or 3, or 2, or 1 hour from administration.

In various embodiments, the modified-release formulation of the present invention may utilize one or more modified-release coatings such as delayed-release coatings to provide for effective, delayed yet substantial delivery of the beta-lactamase to the GI tract together with, optionally, additional therapeutic agents. In one embodiment, the delayed-release coating includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly(methacrylic acid, methylmethacrylate), hydroxypropyl methylcellulose acetate succinate, cellulose acetate trimellitate, shellac or other suitable enteric coating polymers. The EUDRAGIT®-type polymer include, for example, EUDRAGIT® FS 30D, L 30 D-55, L 100-55, L 100, L 12,5, L 12,5 P, RL 30 D, RL PO, RL 100, RL 12,5, RS 30 D, RS PO, RS 100, RS 12,5, NE 30 D, NE 40 D, NM 30 D, S 100, S 12,5, and S 12,5 P. In some embodiments, one or more of EUDRAGIT® FS 30D, L 30 D-55, L 100-55, L 100, L 12,5, L 12,5 P RL 30 D, RL PO, RL 100, RL 12,5, RS 30 D, RS PO, RS 100, RS 12,5, NE 30 D, NE 40 D, NM 30 D, S 100, S 12,5 and S 12,5 P is used. The enteric agent may be a combination of the foregoing solutions or dispersions.

In one embodiment, the modified-release formulation may include one or more delayed-release coating(s) which remain essentially intact, or may be essentially insoluble, in gastric fluid. The stability of the delayed-release coating can be pH dependent. Delayed-release coatings that are pH dependent will be substantially stable in acidic environments (pH of about 5 or less), and substantially unstable in near neutral to alkaline environments (pH greater than about 5). For example, the delayed-release coating may essentially disintegrate or dissolve in near neutral to alkaline environments such as are found in the small intestine (e.g. one or more of the duodenum, jejunum, and ileum) and/or large intestine (e.g. one or more of the cecum, ascending colon, transverse colon, descending colon, and sigmoid colon).

By way of non-limiting example, there are various EUDRAGIT formulations that dissolve at rising pH, with formulations that dissolve at pH>5.5 (EUDRAGIT L30 D-550), pH>6.0 (EUDRAGIT L12, 5), and pH>7.0 (EUDRAGIT FS 30D). Since the ileum has the highest pH in the small intestine, ranging from 7.3 to 7.8, the use of EUDRAGIT FS 30D to coat the pellet containing the antibiotic-degrading enzyme, may delay the dissolution of the pellet until it reaches the ileum thereby localizing the release of the antibiotic-degrading enzyme to the ileum. However, the jejunum has a pH ranging from 6.6 to 7.4, therefore, the release may initiate in some patients in the jejunum, if the pH is at 7.0 or above. In such embodiments, the antibiotic-degrading enzyme may be delivered with an antibiotic/inhibitor combination as described. The different types of EUDRAGIT can be combined with each other, or multiple different types of EUDRAGIT coatings can be combined to fine tune the dissolution profile to achieve targeted delivery to achieve optimal function. For example, EUDRAGIT L100, EUDRAGIT S100, and triethyl citrate may be mixed together at a ratio of, for example, about 72.7/18.2/9.1, to form a coating that substantially releases at a pH of greater than about 6.2. In another example, EUDRAGIT L100, EUDRAGIT S100, and triethyl citrate may be mixed together at a ratio of, for example, about 30/60.9/9, to form a coating that substantially releases at a pH of greater than about 6.7. In a further example, DUOCOAT (KUECEPT) that uses two coatings of enteric polymers (like EUDRAGIT), an outer layer, and an inner layer of partially neutralized enteric polymer and a buffer agent. The DUOCOAT technology allows more rapid release of the therapeutic agent initiated at the targeted pH compared to a single coating of the enteric polymer (Liu et al., 2010, European J. Pharmaceutics and Biopharmaceuticals 47:311, the entire contents of all of which are incorporated herein by reference). Release was demonstrated to be targeted to the ileum and/or ileoceacal junction in 10 healthy volunteers (Varum et al., 2013, European J. Pharmaceutics and Biopharmaceuticals 84:573, the entire contents of all of which are incorporated herein by reference).

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, and EUDRAGIT NE®. Insoluble polymers useful in the present invention include polyvinyl esters, polyvinyl acetals, polyacrylic acid esters, butadiene styrene copolymers, and the like. In one embodiment, colonic delivery is achieved by use of a slowly-eroding wax plug (e.g., various PEGS, including for example, PEG6000) or pectin. In an embodiment, the present invention contemplates the use of a delayed-release coating that degrade as a function of time which comprises a swell layer comprising croscarmellos sodium and hydroxyproplycellulose. In such embodiment, the formulation may further include an osmotic rupture coating that comprises ethylcellulose such as ethylcellulose dispersions.

Alternatively, the stability of the modified-release formulation can be enzyme-dependent. Delayed-release coatings that are enzyme dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine, such as galactomannans. Also, the stability of the modified-release formulation can be dependent on enzyme stability in the presence of a microbial enzyme present in the gut flora. For example, in various embodiments, the delayed-release coating may be degraded by a microbial enzyme present in the gut flora. In an embodiment, the delayed-release coating may be degraded by a bacteria present in the small intestine. In another embodiment, the delayed-release coating may be degraded by a bacteria present in the large intestine.

In various embodiments, the modified-release formulations of the present invention are designed for immediate release (e.g. upon ingestion). In various embodiments, the modified-release formulations may have sustained-release profiles, i.e. slow release of the active ingredient(s) in the body (e.g., GI tract) over an extended period of time. In various embodiments, the modified-release formulations may have a delayed-release profile, i.e. not immediately release the active ingredient(s) upon ingestion; rather, postponement of the release of the active ingredient(s) until the composition is lower in the gastrointestinal tract; for example, for release in the small intestine (e.g., one or more of duodenum, jejunum, ileum) or the large intestine (e.g., one or more of cecum, ascending, transverse, descending or sigmoid portions of the colon, and rectum). For example, a composition can be enteric coated to delay release of the active ingredient(s) until it reaches the small intestine or large intestine. In some embodiments, there is not a substantial amount of the active ingredient(s) of the present formulations in the stool.

In various embodiments, the modified release formulation is designed for release in the colon. Various colon-specific delivery approaches may be utilized. For example, the modified release formulation may be formulated using a colon-specific drug delivery system (CODES) as described for example, in Li et al., AAPS PharmSciTech (2002), 3(4):

1-9, the entire contents of which are incorporated herein by reference. Drug release in such a system is triggered by colonic microflora coupled with pH-sensitive polymer coatings. For example, the formulation may be designed as a core tablet with three layers of polymer. The first coating is an acid-soluble polymer (e.g., EUDRAGIT E), the outer coating is enteric, along with an hydroxypropyl methylcellulose barrier layer interposed in between. In another embodiment, colon delivery may be achieved by formulating the beta-lactamase (and/or additional therapeutic agent) with specific polymers that degrade in the colon such as, for example, pectin. The pectin may be further gelled or crosslinked with a cation such as a zinc cation. In an embodiment, the formulation is in the form of ionically crosslinked pectin beads which are further coated with a polymer (e.g., EUDRAGIT polymer). Additional colon specific formulations include, but are not limited to, pressure-controlled drug delivery systems (prepared with, for example, ethylcellulose) and osmotic controlled drug delivery systems (i.e., ORDS-CT).

Formulations for colon specific delivery of beta-lactamases (and/or additional therapeutic agents), as described herein, may be evaluated using, for example, in vitro dissolution tests. For example, parallel dissolution studies in different buffers may be undertaken to characterize the behavior of the formulations at different pH levels. Alternatively, in vitro enzymatic tests may be carried out. For example, the formulations may be incubated in fermenters containing suitable medium for bacteria, and the amount of drug released at different time intervals is determined. Drug release studies can also be done in buffer medium containing enzymes or rat or guinea pig or rabbit cecal contents and the amount of drug released in a particular time is determined. In a further embodiment, in vivo evaluations may be carried out using animal models such as dogs, guinea pigs, rats, and pigs. Further, clinical evaluation of colon specific drug delivery formulations may be evaluated by calculating drug delivery index (DDI) which considers the relative ratio of RCE (relative colonic tissue exposure to the drug) to RSC (relative amount of drug in blood i.e. that is relative systemic exposure to the drug). Higher drug DDI indicates better colon drug delivery. Absorption of drugs from the colon may be monitored by colonoscopy and intubation.

In various embodiments, the present formulation provide for substantial uniform dissolution of the beta-lactamase (and/or additional therapeutic agent) in the area of release in the GI tract. In an embodiment, the present formulation minimizes patchy or heterogeneous release of the beta-lactamase. For example, when releasing in the distal small intestine or, especially the colon, the distribution of beta-lactamase (and/or additional therapeutic agent) may be heterogeneous and therefore require formulation to minimize local effects.

In some embodiments, a dual pulse formulation is provided. In various embodiments, the present invention provides for modified-release formulations that release multiple doses of the beta-lactamase, at different locations along the intestines, at different times, and/or at different pH. In an illustrative embodiment, the modified-release formulation comprises a first dose of the beta-lactamase and a second dose of the beta-lactamase, wherein the first dose and the second dose are released at different locations along the intestines, at different times, and/or at different pH. For example, the first dose is released at the duodenum, and the second dose is released at the ileum. In another example, the first dose is released at the jejunum, and the second dose is released at the ileum. In other embodiments, the first dose is released at a location along the small intestine (e.g., the duodenum), while the second dose is released along the large intestine (e.g., the ascending colon). In various embodiments, the modified-release formulation may release at least one dose, at least two doses, at least three doses, at least four doses, at least five doses, at least six doses, at least seven doses, or at least eight doses of the beta-lactamase at different locations along the intestines, at different times, and/or at different pH. Further the dual pulse description herein applies to modified-release formulations that release a beta-lactamase and an additional therapeutic agent.

In some embodiments, a dual pulse formulation is provided in which a dose of the beta-lactamase and a dose of an oral antibiotic (and/or a beta-lactamase inhibitor) are released at different locations along the intestines, at different times, and/or at different pH. For example, the dose of an oral antibiotic (and/or a beta-lactamase inhibitor) is released proximal to the dose of the beta-lactamase. For example, the dose of an oral antibiotic (and/or a beta-lactamase inhibitor) is released in the ileum and upstream and the dose of the beta-lactamase is released in the distal small intestine and/or the colon.

In various embodiments, the invention provides a formulation comprising: a core particle having a base coat comprising one or more beta-lactamases, and a delayed-release coating disposed over the coated core particle. The delayed-release coating may be substantially stable in acidic environments and/or gastric fluid, and/or substantially unstable in near neutral to alkaline environments or intestinal fluid thereby exposing the coated core particle to intestinal fluid. The base coat comprising one or more beta-lactamases may further comprise one or more additional therapeutic agents. Optionally a plurality of base coats may be applied to the core particle each of which may contain a beta-lactamase and/or an additional therapeutic agent. In an embodiment, the core particle includes sucrose.

In an embodiment, a beta-lactamases can be sprayed onto an inert core (e.g., a sucrose core or a cellulose core such as a microcrystalline sucrose or cellulose core) and spray-dried with an enteric layer to form beta-lactamase containing pellets or beads. In various embodiments, the enteric layer may comprise one or more enteric agents as described herein. For example, the enteric layer may comprise an EUDRAGIT®-type polymer such as EUDRAGIT L30 D-55, as described for example, in PCT/US2015/054606, the entire disclosure of which is hereby incorporated by reference. In such an embodiment, the formulation comprising the beta-lactamase containing pellets or beads may release the beta-lactamase at a pH of about 5.5.

In an embodiment, the enteric layer may comprise a mixture of EUDRAGIT®-type polymers. In various embodiments, the enteric layer may comprise a mixture of EUDRAGIT L100, EUDRAGIT S100, and triethyl citrate. In some embodiments, the enteric layer comprises about 65% to about 85% of EUDRAGITL100, about 10% to about 30% of EUDRAGIT S100, and about 1% to about 20% of triethyl citrate. In an embodiment, the enteric layer comprises about 73% of EUDRAGITL100, about 18% of EUDRAGIT S100, and about 9% of triethyl citrate. In an embodiment, the enteric layer comprises about 72.7% of EUDRAGITL100, about 18.2% of EUDRAGIT S100, and about 9.1% of triethyl citrate. In such embodiments, the formulation comprising the beta-lactamase containing pellets or beads may release the beta-lactamase at a pH of greater than about 6.2. In various embodiments, the beta-lactamase containing pellets or beads is spray-dried with an enteric layer having a coating weight of about 20%, about 25%, about 30%, about 35%, about 40%, about 45%, or about 50%. In an embodiment, the beta-lactamase containing pellets or beads is spray-dried with an enteric layer having a coating weight of about 35%. In various embodiments, the beta-lactamase containing pellets or beads is spray-dried with an enteric layer having a coating thickness of about 50 µM, about 55 µM, about 60 µM, about 65 µM, about 70 µM, about 75 µM, about 80 µM, about 85 µM, about 90 µM, about 95 µM, about 100 µM, about 105 µM, about 110 µM, about 115 µM, or about 120 µM. In an embodiment, the beta-lactamase containing pellets or beads is spray-dried with an enteric layer having a coating thickness of about 100 µM. In an embodiment, the beta-lactamase containing pellets or beads is spray-dried with an enteric layer having a coating thickness of about 99.7 µM.

In some embodiments, the enteric layer comprises about 20% to about 40% of EUDRAGITL100, about 50% to about 70% of EUDRAGIT S100, and about 1% to about 20% of triethyl citrate. In an embodiment, the enteric layer comprises about 30% of EUDRAGITL100, about 61% of EUDRAGIT S100, and about 9% of triethyl citrate. In an embodiment, the enteric layer comprises about 30% of EUDRAGITL100, about 60.9% of EUDRAGIT S100, and about 9.1% of triethyl citrate. In such embodiments, the formulation comprising the beta-lactamase containing pellets or beads may release the beta-lactamase at a pH of greater than about 6.7. In various embodiments, the beta-lactamase containing pellets or beads is spray-dried with an enteric layer having a coating weight of about 20%, about 25%, about 30%, about 35%, about 40%, about 45%, or about 50%. In an embodiment, the beta-lactamase containing pellets or beads is spray-dried with an enteric layer having a coating weight of about 35%. In various embodiments, the beta-lactamase containing pellets or beads is spray-dried with an enteric layer having a coating thickness of about 50 µM, about 55 µM, about 60 µM, about 65 µM, about 70 µM, about 75 µM, about 80 µM, about 85 µM, about 90 µM, about 95 µM, about 100 µM, about 105 µM, about 110 µM, about 115 µM, or about 120 µM. In an embodiment, the beta-lactamase containing pellets or beads is spray-dried with an enteric layer having a coating thickness of about 110 µM. In an embodiment, the beta-lactamase containing pellets or beads is spray-dried with an enteric layer having a coating thickness of about 113 µM.

In various embodiments, the invention provides a formulation comprising a delayed-release coating that releases the beta-lactamase in a pH-independent manner and/or a time-dependent manner. In various embodiments, the formulation comprises: a core particle having a base coat comprising one or more beta-lactamases, a swell layer, and an osmotic rupture coating disposed over the coated core particle with the swell layer. In an embodiment, a beta-lactamases can be sprayed onto an inert core (e.g., a sucrose core or a cellulose core such as a microcrystalline sucrose or cellulose core) with the swell layer and the osmotic rupture coating added subsequently.

In such embodiments, the delayed-release coating including the swell layer and the osmotic rupture coating allows for release of the beta-lactamase within a specified time frame. In various embodiments, the beta-lactamase is released after about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, or about 10 hours after ingestion. In various embodiments, the swell layer comprises about 60% to about 80% of croscarmellos sodium (e.g., AcDiSol) and about 20% to about 40% of hydroxyproplycellulose (HPC). In an embodiment, the swell layer comprises about 71% pulverized croscarmellos sodium and about 29% hydroxyproplycellulose. In an embodiment, the swell layer comprises about 71.4% pulverized croscarmellos sodium and about 28.6% hydroxyproplycellulose. In various embodiments, the osmotic rupture coating comprises about 65% to about 85% of ethylcellulose dispersion (e.g., Aquacoat ECD) and about 15% to about 35% triethyl citrate. In an embodiment, the osmotic rupture coating comprises about 75% ethylcellulose dispersion and about 25% triethyl citrate. In various embodiments, the beta-lactamase containing pellets or beads with the swell layer and osmotic rupture coating has a coating weight of about 5%, about 10%, about 15%, about 20%, about 25%, or about 30%. In an embodiment, the beta-lactamase containing pellets or beads with the swell layer and osmotic rupture coating has a coating weight of about 13.5%. In various embodiments, the beta-lactamase containing pellets or beads with the swell layer and osmotic rupture coating has a coating thickness of about 20 µM, about 25 µM, about 30 µM, about 35 µM, about 40 µM, about 45 µM, about 50 µM, about 55 µM, or about 60 µM. In an embodiment, the beta-lactamase containing pellets or beads with the swell layer and osmotic rupture coating has a coating thickness of about 50 µM. In an embodiment, the beta-lactamase containing pellets or beads with the swell layer and osmotic rupture coating has a coating thickness of about 48 µM.

Optionally, the core particle may comprise one or more beta-lactamases and/or one or more additional therapeutic agents. In one embodiment, one or more doses of the beta-lactamase may be encapsulated in a core particle, for example, in the form of a microsphere or a mini-sphere. For example, the beta-lactamase may be combined with a polymer (e.g., latex), and then formed into a particulate, microencapsulated enzyme preparation, without using a sucrose core. The microspheres or mini-spheres thus formed may be optionally covered with a delayed-release coating.

A variety of approaches for generating particulates (such as microspheres, mini-spheres, aggregates, other) may be utilized for the inclusion of enzymatic proteins. They typically involve at least two phases, one containing the protein, and one containing a polymer that forms the backbone of the particulate. Most common are coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form, for example, microspheres or mini-spheres. Alternatively, the beta-lactamase and stabilizing excipients (for example, trehalose, mannitol, Tween 80, polyvinyl alcohol) are combined and sprayed from aqueous solution and collected. The particles are then suspended in a dry, water immiscible organic solvent containing polymer and release modifying compounds, and the suspension sonicated to disperse the particles. An additional approach uses aqueous phases but no organic solvent. Specifically, the enzymatic protein, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. When the release modifiers are insoluble at acidic conditions but soluble at higher pHs (such as carboxylic acid) then release from the matrix is inhibited in the gastric environment. In an embodiment, the beta-lactamase may be initially solubilized as an emulsion, microemulsion, or suspension and then formulated into solid mini-spheres or microspheres. The formulation may then be coated with, for example, a delayed-release, sustained-release, or controlled-release coating to achieve delivery at a specific location such as, for example, the intestines.

In various embodiments, the formulation may comprise a plurality of modified-release particles or beads or pellets or microspheres. In an embodiment, the formulation is in the form of capsules comprising multiple beads. In another embodiment, the formulation is in the form of capsules comprising multiple pellets. In another embodiment, the formulation is in the form of capsules comprising multiple microspheres or mini-spheres.

In some embodiments, before applying the delayed-release coating to the coated core particle, the particle can optionally be covered with one or more separating layers comprising pharmaceutical excipients including alkaline compounds such as for instance pH-buffering compounds. The separating layer essentially separates the coated core particle from the delayed-release coating.

The separating layer can be applied to the coated core particle by coating or layering procedures typically used with coating equipment such as a coating pan, coating granulator or in a fluidized bed apparatus using water and/or organic solvents for the coating process. As an alternative the separating layer can be applied to the core material by using a powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methyl-cellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, sodium stearyl fumarate, titanium dioxide, talc and other additives can also be included in the separating layer.

In some embodiments, the coated particles with the delayed-release coating may be further covered with an overcoat layer. The overcoat layer can be applied as described for the other coating compositions. The overcoat materials are pharmaceutically acceptable compounds such as sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. The overcoat materials can prevent potential agglomeration of particles coated with the delayed-release coating, protect the delayed-release coating from cracking during the compaction process or enhance the tableting process.

In various embodiments, the formulation may comprise a plurality of modified-release particles or pellets or microspheres. In one embodiment, the formulation is in the form of capsules comprising multiple pellets. In one embodiment, the formulation is in the form of capsules comprising multiple microspheres.

In some embodiments, the modified-release formulation is a capsule filled with a plurality of beta-lactamase-containing pellets (e.g., P3A (or the other beta-lactamase agents described herein, and variants thereof)-containing pellets) from which the beta-lactamase is released. In an embodiment, the capsule is a gelatin capsule, such as a hard gelatin capsule. In another embodiment, the capsule is a hydroxypropyl methylcellulose (HPMC) capsule. For example, the formulation may be in the form of capsules comprising multiple pellets. For example, the formulation may be in the form of capsules such as, for example, gelatin or hydroxypropyl methylcellulose (HPMC) capsules comprising multiple enteric-coated pellets containing beta-lactamase (e.g. P3A, or the other beta-lactamase agents described herein, and variants thereof). In another example, the formulation may be in the form of capsules such as, for example, gelatin or hydroxypropyl methylcellulose (HPMC) capsules comprising multiple pellets containing beta-lactamase (e.g. P3A, or the other beta-lactamase agents described herein, and variants thereof) coated with an osmotic-rupture coating. In such embodiments, a combination of pellets may be utilized in which each pellet is designed to release at a specific time point or location. In various embodiments, the pellets (e.g., enteric-coated pellets) are designed to pass through the stomach unchanged and then release the beta-lactamase (e.g. P3A, or the other beta-lactamase agents described herein, and variants thereof) into one or more regions of the intestines. In some embodiments, the beta-lactamase-containing pellets may be enteric-coated to release the beta-lactamase (e.g. P3A, or the other beta-lactamase agents described herein, and variants thereof) at different intestinal pH values. In some embodiments, the beta-lactamase-containing pellets may be coated with an osmotic-rupture coating to release the beta-lactamase (e.g. P3A, or the other beta-lactamase agents described herein, and variants thereof) within specific time frames.

In various embodiments, the formulation of the present invention is in the form of a capsule (e.g., a hard gelatin or HPMC capsule) comprising a plurality of enteric-coated beta-lactamase-containing pellets. In such embodiments, the pellets (or each individual pellet) comprise a beta-lactamase (e.g. P3A, or the other beta-lactamase agents described herein, and variants thereof) and a sucrose sphere, which the beta-lactamase, for example, P3A or a variant, is sprayed onto, a coating comprising for example one or more enteric polymers, and/or additional excipients and/or buffer salts. For example, the pellets may comprise a binder excipient (e.g., hydroxypropylcellulose (HPC) or hydroxypropyl methylcellulose (HPMC)), one or more enteric polymers (e.g., EUDRAGIT L 30 D-55, EUDRAGIT L100, EUDRAGIT S100), a plasticizer (e.g., triethyl citrate), and buffer salts.

In various embodiments, the formulation of the present invention is in the form of a capsule (e.g., a hard gelatin or HPMC capsule) comprising a plurality of enteric-coated beta-lactamase-containing pellets. In such embodiments, the pellets (or each individual pellet) comprise about 10-20% by weight of beta-lactamase (e.g. P3A, or the other beta-lactamase agents described herein, and variants thereof). For example, the beta-lactamase (e.g. P3A, or the other beta-lactamase agents described herein, and variants thereof) may be present at about 10%, about 11%, about 12%, about 13%, about 14%, about 15%, about 16%, about 17%, about 18%, about 19%, or about 20% by weight. In some embodiments, the pellets (or each individual pellet) comprise about 10-25% by weight sucrose sphere, which the beta-lactamase, for example, P3A or a variant, is sprayed onto. For example, the sucrose sphere may be present at about 10%, about 11%, about 12%, about 13%, about 14%, about 15%, about 16%, about 17%, about 18%, about 19%, about 20%, about 21%, about 22%, about 23%, about 24%, or about 25% by weight. In various embodiments, the pellets (or each individual pellet) comprise about 20-35% by weight a binder excipient (e.g., hydroxypropylcellulose (HPC) or hydroxypropyl methylcellulose (HPMC)). For example, the binder excipient may be present at about 20%, about 21%, about 22%, about 23%, about 24%, or about 25%, about 26%, about 27%, about 28%, about 29%, about 30%, about 31%, about 32%, about 33%, about 34%, or about 35% by weight. In some embodiments, the pellets (or each individual pellet) comprise about 10-30% by weight of a first enteric polymer (e.g., EUDRAGIT L100). For example, the first enteric polymer (e.g., EUDRAGIT L100) may be present at about about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% by weight. In some embodiments, the pellets (or each individual pellet) comprise about 1-30% by weight of a second enteric polymer (e.g., EUDRAGIT S100). For example, the second enteric polymer (e.g., EUDRAGIT S100) may be present at about about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% by weight. In some embodiments, the pellets (or each individual pellet) comprise about 1-10% by weight of plasticizer (e.g., triethyl citrate). For example, the plasticizer may be present at about 1%, about 2%, about 3%, about 4%, about 5%, about 6%, about 7%, about 8%, about 9%, or about 10% by weight. In some embodiments, the pellets (or each individual pellet) further comprise about 1-2% by weight buffer salts. For example, the buffer salts may be present at about 1.1%, about 1.2%, about 1.3%, about 1.4%, about 1.5%, about 1.6%, about 1.7%, about 1.8%, about 1.9%, or about 2% by weight. The weight as described herein refers to the total weight of all components excluding the weight of the capsule itself.

In some embodiments, the pellets (or each individual pellet) comprise about 14% by weight of the beta-lactamase (e.g. P3A, or the other beta-lactamase agents described herein, and variants thereof); about 21% by weight sucrose sphere; about 31% by weight a binder excipient (e.g., hydroxypropylcellulose (HPC) or hydroxypropyl methylcellulose (HPMC)); about 24% by weight a first enteric polymer (e.g., EUDRAGIT L100); about 6% by weight a second enteric polymer (e.g., EUDRAGIT S100); about 3% by weight of plasticizer (e.g., triethyl citrate); and about 1% by weight buffer salts. The weight as described herein refers to the total weight of all components excluding the weight of the capsule itself. In such embodiments, the pellets may release the beta-lactamase at a pH of greater than about 6, about 6.1, about 6.2, about 6.3, about 6.4, or about 6.5. In an embodment, the pellets may release the beta-lactamase at a pH of greater than about 6.2.

For example, the pellets (or each individual pellet) comprise about 13.9% by weight of the beta-lactamase (e.g. P3A, or the other beta-lactamase agents described herein, and variants thereof); about 20.5% by weight sucrose sphere; about 30.7% by weight a binder excipient (e.g., hydroxypropylcellulose (HPC)); about 24.3% by weight a first enteric polymer (e.g., EUDRAGIT L100); about 6.1% by weight a second enteric polymer (e.g., EUDRAGIT S100); about 3% by weight of plasticizer (e.g., triethyl citrate); and about 1.4% by weight buffer salts. The weight as described herein refers to the total weight of all components excluding the weight of the capsule itself. In an embodiment, the pellets may release the beta-lactamase at a pH of greater than about 6.2.

In some embodiments, the pellets (or each individual pellet) comprise about 13% by weight of the beta-lactamase (e.g. P3A, or the other beta-lactamase agents described herein, and variants thereof); about 18% by weight sucrose sphere; about 28% by weight a binder excipient (e.g., hydroxypropylcellulose (HPC) or hydroxypropyl methylcellulose (HPMC)); about 12% by weight a first enteric polymer (e.g., EUDRAGIT L100); about 25% by weight a second enteric polymer (e.g., EUDRAGIT S100); about 4% by weight of plasticizer (e.g., triethyl citrate); and about 1% by weight buffer salts. The weight as described herein refers to the total weight of all components excluding the weight of the capsule itself. In such embodiments, the pellets may release the beta-lactamase at a pH of greater than about 6.5, about 6.6, about 6.7, about 6.8, about 6.9, or about 7.0. In an embodmient, the pellets may release the beta-lactamase at a pH of greater than about 6.7.

For example, the pellets (or each individual pellet) comprise about 12.5% by weight of the beta-lactamase (e.g. P3A, or the other beta-lactamase agents described herein, and variants thereof); about 18.4% by weight sucrose sphere; about 27.5% by weight a binder excipient (e.g., hydroxypropylcellulose (HPC)); about 12.2% by weight a first enteric polymer (e.g., EUDRAGIT L100); about 24.5% by weight a second enteric polymer (e.g., EUDRAGIT S100); about 3.7% by weight of plasticizer (e.g., triethyl citrate); and about 1.3% by weight buffer salts. The weight as described herein refers to the total weight of all components excluding the weight of the capsule itself. In the embodiment, the pellets may release the beta-lactamase at a pH of greater than about 6.7.

In various embodiments, the formulation of the present invention is in the form of a capsule (e.g., a hard gelatin or HPMC capsule) comprising about 50 mg of the beta-lactamase (e.g. P3A, or the other beta-lactamase agents described herein, and variants thereof). The capsule includes a plurality of enteric-coated beta-lactamase-containing pellets. In such embodiments, the formulation comprises about 5-15% by weight of the beta-lactamase (e.g. P3A, or the other beta-lactamase agents described herein, and variants thereof). For example, the beta-lactamase (e.g. P3A, or the other beta-lactamase agents described herein, and variants thereof) may be present at about about 5%, about 6%, about 7%, about 8%, about 9%, about 10%, about 11%, about 12%, about 13%, about 14%, or about 15% by weight. In some embodiments, the formulation comprises about 10-20% by weight sucrose sphere. For example, the sucrose sphere may be present about 10%, about 11%, about 12%, about 13%, about 14%, about 15%, about 16%, about 17%, about 18%, about 19%, or about 20% by weight. In various embodiments, the formulation comprises about 20-30% by weight a binder excipient (e.g., hydroxypropylcellulose (HPC) or hydroxypropyl methylcellulose (HPMC)). For example, the binder excipient may be present at abuot 20%, about 21%, about 22%, about 23%, about 24%, about 25%, about 26%, about 27%, about 28%, about 29%, or about 30% by weight. In some embodiments, the formulation comprises about 5-25% by weight a first enteric polymer (e.g., EUDRAGIT L100). For example, the first enteric polymer may be present at about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight. In some embodiments, the formulation comprises about 1-25% by weight a second enteric polymer (e.g., EUDRAGIT S100). For example, the second enteric polymer may be present at about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight. In some embodiments, the formulation comprises about 1-10% by weight of plasticizer (e.g., triethyl citrate). For example, the plasticizer may be present at about 1%, about 2%, about 3%, about 4%, about 5%, about 6%, about 7%, about 8%, about 9%, or about 10% by weight. In some embodiments, the formulation comprises about 0.5-1.5% by weight buffer salts. For example, the buffer salts may be present at about about 0.5%, about 0.6%, about 0.7%, about 0.8%, about 0.9%, about 1.1%, about 1.2%, about 1.3%, about 1.4%, or about 1.5% by weight. In some embodiments, the formulation comprises about 15-25% by weight gelatin or HPMC capsule. For example, the gelatin or HPMC capsule may be about 15%, about 16%, about 17%, about 18%, about 19%, about 20% about 21%, about 22%, about 23%, about 24%, or about 25% by weight.

In some embodiments, the formulation of the present invention comprises about 50 mg of the beta-lactamase (e.g. P3A, or the other beta-lactamase agents described herein, and variants thereof). In such embodiments, the formulation comprises about 11% by weight of the beta-lactamase (e.g. P3A, or the other beta-lactamase agents described herein, and variants thereof); about 17% by weight sucrose sphere; about 25% by weight a binder excipient (e.g., hydroxypropylcellulose (HPC)); about 20% by weight a first enteric polymer (e.g., EUDRAGIT L100); about 5% by weight a second enteric polymer (e.g., EUDRAGIT S100); about 2% by weight of plasticizer (e.g., triethyl citrate); about 1% by weight buffer salts; and about 21% by weight gelatin or HPMC capsule. In such embodiments, the pellets within the capsule may release the beta-lactamase at a pH of greater than about 6, about 6.1, about 6.2, about 6.3, about 6.4, or about 6.5. In an embodmient, the pellets may release the beta-lactamase at a pH of greater than about 6.2.

For example, the formulation comprises about 11.2% by weight of the beta-lactamase (e.g. P3A, or the other beta-lactamase agents described herein, and variants thereof); about 16.6% by weight sucrose sphere; about 24.8% by weight a binder excipient (e.g., hydroxypropylcellulose (HPC)); about 19.7% by weight a first enteric polymer (e.g., EUDRAGIT L100); about 4.9% by weight a second enteric polymer (e.g., EUDRAGIT S100); about 2.4% by weight of plasticizer (e.g., triethyl citrate); about 1.1% by weight buffer salts; and about 20.9% by weight gelatin or HPMC capsule. In an embodmient, the pellets within the capsule may release the beta-lactamase at a pH of greater than about 6.2.

In some embodiments, the formulation of the present invention comprises about 50 mg of the beta-lactamase (e.g. P3A, or the other beta-lactamase agents described herein, and variants thereof). In such embodiments, the formulation comprises about 10% by weight of the beta-lactamase (e.g. P3A, or the other beta-lactamase agents described herein, and variants thereof); about 15% by weight sucrose sphere; about 22% by weight a binder excipient (e.g., hydroxypropylcellulose (HPC)); about 10% by weight a first enteric polymer (e.g., EUDRAGIT L100); about 20% by weight a second enteric polymer (e.g., EUDRAGIT S100); about 3% by weight of plasticizer (e.g., triethyl citrate); about 1% by weight buffer salts; and about 19% by weight gelatin or HPMC capsule. In such embodiments, the pellets within the capsule may release the beta-lactamase at a pH of greater than about 6.5, about 6.6, about 6.7, about 6.8, about 6.9, or about 7.0. In an embodmient, the pellets may release the beta-lactamase at a pH of greater than about 6.7.

For example, the formulation comprises about 10.1% by weight of the beta-lactamase (e.g. P3A, or the other beta-lactamase agents described herein, and variants thereof); about 14.9% by weight sucrose sphere; about 22.4% by weight a binder excipient (e.g., hydroxypropylcellulose (HPC)); about 9.9% by weight a first enteric polymer (e.g., EUDRAGIT L100); about 19.9% by weight a second enteric polymer (e.g., EUDRAGIT S100); about 3% by weight of plasticizer (e.g., triethyl citrate); about 1% by weight buffer salts; and about 18.8% by weight gelatin or HPMC capsule. In an embodmient, the pellets within the capsule may release the beta-lactamase at a pH of greater than about 6.7.

In various embodiments, the formulation of the present invention is in the form of a capsule (e.g., a hard gelatin or HPMC capsule) comprising a plurality of beta-lactamase-containing pellets whch are coated with a swelling layer and/or an osmotic rupture coating. In such embodiments, the pellets (or each individual pellet) comprise a beta-lactamase (e.g. P3A, or the other beta-lactamase agents described herein, and variants thereof) and a sucrose sphere, which the beta-lactamase, for example, P3A or a variant, is sprayed onto, one or more coatings comprising for example one or more swelling layers and/or osmotic rupture coatings, and/or additional excipients and/or buffer salts. For example, the pellets may comprise a binder excipient (e.g., hydroxypropylcellulose (HPC) or hydroxypropyl methylcellulose (HPMC)), one or more swelling layers comprising, for example, croscarmellos sodium (e.g., pulverized croscarmellos sodium such as AcDiSol), one or more osmotic rupture coatings comprising, for example, ethylcellulose (e.g., ethylcellulose dispersions such as Aquacoat ECD), one or more excipient s (e.g., talc), and buffer salts.

In various embodiments, the formulation of the present invention is in the form of a capsule (e.g., a hard gelatin or HPMC capsule) comprising a plurality of beta-lactamase-containing pellets coated with a swelling layer and/or an osmotic rupture coating. In such embodiments, the pellets (or each individual pellet) comprise about 5-15% by weight of beta-lactamase (e.g. P3A, or the other beta-lactamase agents described herein, and variants thereof). For example, the beta-lactamase (e.g. P3A, or the other beta-lactamase agents described herein, and variants thereof) may be present at about 5%, about 6%, about 7%, about 8%, about 9%, about 10%, about 11%, about 12%, about 13%, about 14%, or about 15% by weight. In some embodiments, the pellets (or each individual pellet) comprise about 10-20% by weight sucrose sphere, which the beta-lactamase, for example, P3A or a variant, is sprayed onto. For example, the sucrose sphere may be present at about 10%, about 11%, about 12%, about 13%, about 14%, about 15%, about 16%, about 17%, about 18%, about 19%, or about 20% by weight. In various embodiments, the pellets (or each individual pellet) comprise about 25-35% by weight a binder excipient (e.g., hydroxypropylcellulose (HPC) or hydroxypropyl methylcellulose (HPMC)). For example, the binder excipient may be present at about 25%, about 26%, about 27%, about 28%, about 29%, about 30%, about 31%, about 32%, about 33%, about 34%, or about 35% by weight. In some embodiments, the pellets (or each individual pellet) comprise a swelling layer comprising pulverized croscarmellos sodium (e.g., AcDiSol), which is about 20-30% by weight. For example, the pulverized croscarmellos sodium (e.g., AcDiSol) may be present at about 20%, about 21%, about 22%, about 23%, about 24%, about 25%, about 26%, about 27%, about 28%, about 29%, or about 30% by weight. In some embodiments, the pellets (or each individual pellet) comprise an osmotic rupture coating comprising ethylcellulose dispersion (e.g., Aquacoat ECD), which is about 1-10% by weight. For example, the ethylcellulose dispersion (e.g., Aquacoat ECD) may be present at about 1%, about 2%, about 3%, about 4%, about 5%, about 6%, about 7%, about 8%, about 9%, or about 10% by weight. In some embodiments, the pellets (or each individual pellet) comprise about 1-10% by weight of an excipient (e.g., talc). For example, the excipient may be present at about 1%, about 2%, about 3%, about 4%, about 5%, about 6%, about 7%, about 8%, about 9%, or about 10% by weight. In some embodiments, the pellets (or each individual pellet) further comprise about 0.5-1.5% by weight buffer salts. For example, the buffer salts may be present at about 0.5%, about 0.6%, about 0.7%, about 0.8%, about 0.9%, about 1.1%, about 1.2%, about 1.3%, about 1.4%, or about 1.5% by weight. The weight as described herein refers to the total weight of all components excluding the weight of the capsule itself.

In some embodiments, the pellets (or each individual pellet) comprise about 11% by weight of the beta-lactamase (e.g. P3A, or the other beta-lactamase agents described herein, and variants thereof); about 17% by weight sucrose sphere; about 31% by weight a binder excipient (e.g., hydroxypropylcellulose (HPC) or hydroxypropyl methylcellulose (HPMC)); about 25% by weight pulverized croscarmellos sodium (e.g., AcDiSol); about 7% by weight ethylcellulose dispersion (e.g., Aquacoat ECD); about 9% by weight of an excipient (e.g., talc); and about 1% by weight buffer salts. The weight as described herein refers to the total weight of all components excluding the weight of the capsule itself.

For example, the pellets (or each individual pellet) comprise about 11.2% by weight of the beta-lactamase (e.g. P3A, or the other beta-lactamase agents described herein, and variants thereof); about 16.5% by weight sucrose sphere; about 31.3% by weight a binder excipient (e.g., hydroxypropylcellulose (HPC) or hydroxypropyl methylcellulose (HPMC)); about 24.8% by weight pulverized croscarmellos sodium (e.g., AcDiSol); about 6.6% by weight ethylcellulose dispersion (e.g., Aquacoat ECD); about 8.6% by weight of an excipient (e.g., talc); and about 1.1% by weight buffer salts. The weight as described herein refers to the total weight of all components excluding the weight of the capsule itself. The weight as described herein refers to the total weight of all components excluding the weight of the capsule itself.

In various embodiments, the formulation of the present invention is in the form of a capsule (e.g., a hard gelatin or HPMC capsule) comprising about 50 mg of the beta-lactamase (e.g. P3A, or the other beta-lactamase agents described herein, and variants thereof). The capsule includes a plurality of beta-lactamase-containing pellets coated with a swelling layer and/or an osmotic rupture coating. In such embodiments, the formulation comprises about 5-15% by weight of the beta-lactamase (e.g. P3A, or the other beta-lactamase agents described herein, and variants thereof). For example, the beta-lactamase (e.g. P3A, or the other beta-lactamase agents described herein, and variants thereof) may be present at about about 5%, about 6%, about 7%, about 8%, about 9%, about 10%, about 11%, about 12%, about 13%, about 14%, or about 15% by weight. In some embodiments, the formulation comprises about 10-20% by weight sucrose sphere. For example, the sucrose sphere may be present about 10%, about 11%, about 12%, about 13%, about 14%, about 15%, about 16%, about 17%, about 18%, about 19%, or about 20% by weight. In some embodiments, the formulation comprises about 20-30% by weight a binder excipient (e.g., hydroxypropylcellulose (HPC) or hydroxypropyl methylcellulose (HPMC)). For example, the binder excipient may be present at about 20%, about 21%, about 22%, about 23%, about 24%, about 25%, about 26%, about 27%, about 28%, about 29%, or about 30% by weight. In some embodiments, the formulation comprises about 15-25% by weight croscarmellos sodium (e.g., AcDiSol). For example, the croscarmellos sodium (e.g., AcDiSol) may be present at about 15%, about 16%, about 17%, about 18%, about 19%, about 20%, about 21%, about 22%, about 23%, about 24%, or about 25% by weight. In some embodiments, the formulation comprises about 1-10% by weight ethylcellulose dispersion (e.g., Aquacoat ECD). For example, the ethylcellulose dispersion (e.g., Aquacoat ECD) may be present at about 1%, about 2%, about 3%, about 4%, about 5%, about 6%, about 7%, about 8%, about 9%, or about 10% by weight. In some embodiments, the formulation comprises about 1-10% by weight of an excipient (e.g., talc). For example, the excipient may be present at about 1%, about 2%, about 3%, about 4%, about 5%, about 6%, about 7%, about 8%, about 9%, or about 10% by weight. In some embodiments, the formulation comprises about 0.5-1.5% by weight buffer salts. For example, the buffer salts may be present at about about 0.5%, about 0.6%, about 0.7%, about 0.8%, about 0.9%, about 1.1%, about 1.2%, about 1.3%, about 1.4%, or about 1.5% by weight. In some embodiments, the formulation comprises about 10-20% by weight gelatin or HPMC capsule. For example, the gelatin or HPMC capsule may be about 10%, about 11%, about 12%, about 13%, about 14%, about 15%, about 16%, about 17%, about 18%, about 19%, or about 20% by weight.

In some embodiments, the formulation of the present invention comprises about 50 mg of the beta-lactamase (e.g. P3A, or the other beta-lactamase agents described herein, and variants thereof). In such embodiments, the formulation comprises about 9% by weight of the beta-lactamase (e.g. P3A, or the other beta-lactamase agents described herein, and variants thereof); about 14% by weight sucrose sphere; about 26% by weight a binder excipient (e.g., hydroxypropylcellulose (HPC) or hydroxypropyl methylcellulose (HPMC)); about 20% by weight croscarmellos sodium (e.g., AcDiSol); about 5% by weight ethylcellulose dispersion (e.g., Aquacoat ECD); about 7% by weight of an excipient (e.g., talc); about 1% by weight buffer salts; and about 17% by weight gelatin or HPMC capsule.

For example, the formulation may comprise about 9.3% by weight of the beta-lactamase (e.g. P3A, or the other beta-lactamase agents described herein, and variants thereof); about 13.7% by weight sucrose sphere; about 26% by weight a binder excipient (e.g., hydroxypropylcellulose (HPC) or hydroxypropyl methylcellulose (HPMC)); about 20.4% by weight croscarmellos sodium (e.g., AcDiSol); about 5.4% by weight ethylcellulose dispersion (e.g., Aquacoat ECD); about 7.1% by weight of an excipient (e.g., talc); about 0.9% by weight buffer salts; and about 17.3% by weight gelatin or HPMC capsule.

In some embodiments, the present formulations are those presented in TABLE 5.

In various embodiments, the formulations may combine a beta-lactamase with a latex, or other polymer, and a particulate, micro-encapsulated enzyme preparation will be formed. The microspheres then may be covered with a pH-dependent enteric coating. In some embodiments, no sucrose core is required and this allows for higher drug loading per pellet and therefore a smaller capsule size for therapy. There are a variety of approaches for generating particulates (such as microspheres, aggregates, other) that are amenable to the inclusion of proteins. In some embodiments, the approaches involve at least two phases, one containing the protein, and one containing a polymer that forms the backbone of the particulate. For example, one or more of the following may be used: coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form the microspheres.

In some embodiments, the protein and stabilizing excipients (e.g., trehalose, mannitol, Tween 80, polyvinyl alcohol) are combined and then the mixture is sprayed from aqueous solution and particles that are formed are collected. The particles are then suspended in a dry, water immiscible organic solvent containing polymer and release modifying compounds, and the suspension sonicated to disperse the particles. It is anticipated that the enzyme will retain its activity following this process. Another approach uses aqueous phases but no organic solvent. Here, the enzyme, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. If the release modifiers are insoluble at acidic conditions but soluble at higher pHs (such as carboxylic acidic) then release from the matrix should be inhibited in the gastric environment.

In various embodiments, the formulations of the present invention take the form of those as described in U.S. Provisional Patent Application No. 62/061,507, the entire contents of all of which are incorporated herein by reference.

In various embodiments, the formulations of the present invention take the form of those as described in one or more of U.S. Pat. Nos. 8,535,713 and 8,911,777 and US Patent Publication Nos. 20120141585, 20120141531, 2006/001896, 2007/0292523, 2008/0020018, 2008/0113031, 2010/0203120, 2010/0255087, 2010/0297221, 2011/0052645, 2013/0243873, 2013/0330411, 2014/0017313, and 2014/0234418, the contents of which are hereby incorporated by reference in their entirety.

In various embodiments, the formulations of the present invention take the form of those as described in International Patent Publication No. WO 2008/135090, the contents of which are hereby incorporated by reference in their entirety.

In various embodiments, the formulations of the present invention take the form of those described in one or more of U.S. Pat. Nos. 4,196,564; 4,196,565; 4,247,006; 4,250,997; 4,268,265; 5,317,849; 6,572,892; 7,712,634; 8,074,835; 8,398,912; 8,440,224; 8,557,294; 8,646,591; 8,739,812; 8,810,259; 8,852,631; and 8,911,788 and US Patent Publication Nos. 2014/0302132; 2014/022735T 20140088202; 20130287842; 2013/0295188; 2013/0307962 and 20130184290 the contents of which are hereby incorporated by reference in their entirety.

In some embodiments, the present formulation includes about 0.1-1% beta-lactamase, about 0.1-1% pore former, about 5-15% matrix, about 0.1-1% lubricant, about 0.1-1% buffer, about 0.5-5% protectant, and about 80-90% water. In some embodiments, the present formulation includes about 0.1-1% beta-lactamase (e.g. P3A), about 0.1-1% pore former (e.g. HPMCAS-MF), about 5-15% matrix (e.g. Aquacoat (FMC)), about 0.1-1% lubricant (e.g. Sodium-Stearyl Fumarate), about 0.1-1% buffer (e.g. Sodium Hydrogen Phosphate), about 0.5-5% protectant (e.g. Trehalose), and about 80-90% water.

In some embodiments, the present formulation includes about 0.5% beta-lactamase, about 0.5% pore former, about 10% matrix, about 0.5% lubricant, about 0.5% buffer, about 1% protectant, and about 90% water. In some embodiments, the present formulation includes about 0.5% beta-lactamase (e.g. P3A), about 0.5% pore former (e.g. HPMCAS-MF), about 10% matrix (e.g. Aquacoat (FMC)), about 0.5% lubricant (e.g. Sodium-Stearyl Fumarate), about 0.5% buffer (e.g. Sodium Hydrogen Phosphate), about 1% protectant (e.g. Trehalose), and about 90% water.

In some embodiments, the present formulation includes about 0.5% beta-lactamase, about 0.3% pore former, about 10.1% matrix, about 0.2% lubricant, about 0.1% buffer, about 1% protectant, and about 88.8% water. In some embodiments, the present formulation includes about 0.5% beta-lactamase (e.g. P3A), about 0.3% pore former (e.g. HPMCAS-MF), about 10.1% matrix (e.g. Aquacoat (FMC)), about 0.2% lubricant (e.g. Sodium-Stearyl Fumarate), about 0.1% buffer (e.g. Sodium Hydrogen Phosphate), about 1% protectant (e.g. Trehalose), and about 88.8% water.

In some embodiments, the present formulation is that of TABLE 7.

In some embodiments, the present formulation includes about 0.5-2.5% beta-lactamase, about 0.1-1% pore former, about 5-15% matrix, about 0.1-1% lubricant, about 0.1-1% buffer, and about 80-90% water. In some embodiments, the present formulation includes about 0.5-2.5% beta-lactamase (e.g. P3A), about 0.1-1% pore former (e.g. HPMCAS-MF), about 5-15% matrix (e.g. Aquacoat (FMC)), about 0.1-1% lubricant (e.g. Sodium-Stearyl Fumarate), about 0.1-1% buffer (e.g. Sodium Hydrogen Phosphate), and about 80-90% water.

In some embodiments, the present formulation includes about 2.5% beta-lactamase, about 0.5% pore former, about 10% matrix, about 0.5% lubricant, about 0.5% buffer, and about 90% water. In some embodiments, the present formulation includes about 2.5% beta-lactamase (e.g. P3A), about 0.5% pore former (e.g. HPMCAS-MF), about 10% matrix (e.g. Aquacoat (FMC)), about 0.5% lubricant (e.g. Sodium-Stearyl Fumarate), about 0.5% buffer (e.g. Sodium Hydrogen Phosphate), and about 90% water.

In some embodiments, the present formulation includes about 2.3% beta-lactamase, about 0.3% pore former, about 10% matrix, about 0.1% lubricant, about 0.1% buffer, and about 88.8% water. In some embodiments, the present formulation includes about 2.3% beta-lactamase (e.g. P3A), about 0.3% pore former (e.g. HPMCAS-MF), about 10% matrix (e.g. Aquacoat (FMC)), about 0.1% lubricant (e.g. Sodium-Stearyl Fumarate), about 0.1% buffer (e.g. Sodium Hydrogen Phosphate), and about 88.8% water.

In some embodiments, the present formulation is that of TABLE 8.

In various embodiments, the beta-lactamase described herein is formulated for microorganism-based release. In some embodiments, the beta-lactamase is formulated for release by a genetically-modified microorganism, optionally selected from fungi, bacteria, and algae. In some embodiments, the genetically-modified microorganism is resistant to one or more oral antibiotic. For example, the invention may pertain to a genetically-modified microorganism comprising one or more beta-lactamases that is formulated for GI tract delivery as described herein and that releases the beta-lactamases, e.g. by secretion. For example, a genetically-modified microorganism comprising one or more beta-lactamases may be formulated for release in the distal small intestine and/or colon and, when released, in turn, secretes or otherwise releases (e.g. via genetically-modified microorganism death or digestion) the beta-lactamase so it may eliminate residual or excess oral antibiotic (e.g. active antibiotic that is not absorbed from the GI tract after an oral dose or is returned in active form to the intestinal tract from the systemic circulation) and prevent GI tract microbiota disruption.

In various embodiments, the genetically-modified microorganism comprising one or more beta-lactamases is formulated so as to deliver viable recombinant yeast cells to the intestines where active beta-lactamases are secreted by the genetically-modified microorganisms. In one embodiment, the genetically-modified microorganism comprising one or more beta-lactamases is formulated as an enteric-coated capsule which directly releases the recombinant genetically-modified microorganism in the intestines. In other embodiments, the genetically-modified microorganism comprising one or more beta-lactamases can be formulated as a gelatin capsule, or the genetically-modified microorganism comprising one or more beta-lactamases can be dissolved in a liquid and ingested. In such embodiments, the genetically-modified microorganism comprising one or more beta-lactamases is delivered anywhere along the GI tract. As described herein, the genetically-modified microorganism comprising one or more beta-lactamases can be released in the distal small intestine and/or the colon; however, delivery anywhere in the GI tract is also imagined, for example, where the genetically-modified microorganism comprising one or more beta-lactamases is able to transit to the area of interest without loss of activity or disruption of the systemic activity of the oral antibiotics. By way of illustration, in some embodiments, a recombinant yeast cell, for example, *Saccharomyces boulardii*, is resistant to stomach acid and remains viable during transit to the intestine, where it secretes active beta-lactamases for neutralizing residual or excess oral antibiotic (e.g. active antibiotic that is not absorbed from the GI tract after an oral dose or is returned in active form to the intestinal tract from the systemic circulation) in the lower GI tract.

In some embodiments, genetically-modified microorganism comprising one or more beta-lactamases quickly transits through the small intestine but transits slowly in the colon and therefore remains in the colon longer and any beta lactamase it secretes or releases concentrates in the colon.

In some embodiments, the genetically-modified microorganism is a yeast cell. In various embodiments, the yeast cell is selected from *Saccharomyces* spp., *Hansenula* spp., *Kluyveromyces* spp. *Schizzosaccharomyces* spp. *Zygosaccharoinyces* spp., *Pichia* spp., *Monascus* spp., *Geotrichum* spp. and *Yarrowia* spp. In various embodiments, the present invention contemplates expression of a beta-lactamase in a recombinant yeast cell. The recombinant yeast cell may be generated by stable integration into yeast chromosomal DNA of expression cassette(s) that encode and can express the one or more beta-lactamases. Alternatively, recombinant yeast cell may be generated using a process in which the yeast maintains an expression cassette(s) that encode and can express the one or more beta-lactamases on a stable episome. The recombinant yeast cell may be any yeast cell that is capable of surviving in the mammalian intestine. In various embodiments, the yeast cell has a known probiotic capacity, such as yeast strains selected from kefir, kombucha or dairy products. I In one embodiment, the recombinant yeast cell is *Saccharomyces cerevisiae*. In another embodiment, the recombinant yeast cell is the *Saccharomyces cerevisiae* subspecies *Saccharomyces boulardii* (by way of non-limiting example, ATCC 74352 and/or any cells in U.S. Pat. Nos. 6,010,695 and 7,799,328 the contents of which are hereby incorporated by reference in their entirety). *S. cerevasiae* has been marketed for over 40 years as a probiotic. It has been used for the prevention and the treatment of diarrheal diseases, including antibiotic-associated diarrhea and *C. difficile* infection (reviewed by Kelesidis and Pothoulakis, 2012; Hatoum et al., 2012). *S. boulardii* differs from other *S. cerevasiae* strains as the optimal growth temperature of *S. boulardii* is 37° C. while other strains prefer lower temperatures (between 30 and 33° C.), *S. boulardii* is resistant to low pH and is highly tolerant to bile acids (Edwards-Ingram et al., 2007; Graff et al., 2008). *S. boulardii* was demonstrated to survive the intestinal tract in humans (Klein et al., 1993) where 0.1% viable yeast was recovered in feces after a single administration of $10^{10}$ cells. Concurrent antibiotic treatment increased recovery two-fold (Klein et al., 1993).

In some embodiments, the genetically-modified microorganism is a bacterial cell. In some embodiments, the bacterial cell is a *Bacillus* spp. In some embodiments, the genetically-modified microorganism is an algal cell (e.g. *Chlamydomonas* spp., e.g. *Chlamydomonas reinhardtii*) or the chloroplasts thereof.

In some embodiments, the genetically-modified microorganism is one or more of *Saccharomyces boulardii; Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus* (Bio-K+CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve*, and *Streptococcus salivarius* subsp. *thermophilus* (VSL #3)).

Such genetically-modified microorganisms may be administered as described herein, including by way of example, enterally, such as orally.

Administration and Dosage

It will be appreciated that the actual dose of the beta-lactamase (and/or additional therapeutic agents) to be administered according to the present invention will vary according to, for example, the particular dosage form and the mode of administration. Many factors that may modify the action of the beta-lactamase (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

Individual doses of the beta-lactamase (and/or additional therapeutic agents) can be administered in unit dosage forms (e.g., tablets or capsules) containing, for example, from about 0.01 mg to about 5,000 mg, from about 0.01 mg to about 4,000 mg, from about 0.01 mg to about 3,000 mg, from about 0.01 mg to about 2,000 mg, from about 0.01 mg to about 1,000 mg, from about 0.01 mg to about 950 mg, from about 0.01 mg to about 900 mg, from about 0.01 mg to about 850 mg, from about 0.01 mg to about 800 mg, from about 0.01 mg to about 750 mg, from about 0.01 mg to about 700 mg, from about 0.01 mg to about 650 mg, from about 0.01 mg to about 600 mg, from about 0.01 mg to about 550 mg, from about 0.01 mg to about 500 mg, from about 0.01 mg to about 450 mg, from about 0.01 mg to about 400 mg, from about 0.01 mg to about 350 mg, from about 0.01 mg to about 300 mg, from about 0.01 mg to about 250 mg, from about 0.01 mg to about 200 mg, from about 0.01 mg to about 150 mg, from about 0.01 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg of the active ingredient per unit dosage form, or from about 5 mg to about 80 mg per unit dosage form. For example, a unit dosage form can include about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 2,000 mg, about 3,000 mg, about 4,000 mg, or about 5,000 mg of the active ingredient, inclusive of all values and ranges therebetween.

In one embodiment, the beta-lactamase (and/or additional therapeutic agents) is administered at an amount of from about 0.01 mg to about 100 mg daily, an amount of from about 0.01 mg to about 5,000 mg daily, about 0.01 mg to about 4,000 mg daily, about 0.01 mg to about 3,000 mg daily, about 0.01 mg to about 2,000 mg daily, about 0.01 mg to about 1,000 mg daily, from about 0.01 mg to about 950 mg daily, from about 0.01 mg to about 900 mg daily, from about 0.01 mg to about 850 mg daily, from about 0.01 mg to about 800 mg daily, from about 0.01 mg to about 750 mg daily, from about 0.01 mg to about 700 mg daily, from about 0.01 mg to about 650 mg daily, from about 0.01 mg to about 600 mg daily, from about 0.01 mg to about 550 mg daily, from about 0.01 mg to about 500 mg daily, from about 0.01 mg to about 450 mg daily, from about 0.01 mg to about 400 mg daily, from about 0.01 mg to about 350 mg daily, from about 0.01 mg to about 300 mg daily, from about 0.01 mg to about 250 mg daily, from about 0.01 mg to about 200 mg daily, from about 0.01 mg to about 150 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the beta-lactamase (and/or additional therapeutic agents) is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 2,000 mg, about 3,000 mg, about 4,000 mg, or about 5,000 mg inclusive of all values and ranges therebetween.

In some embodiments, a suitable dosage of the beta-lactamase (and/or additional therapeutic agents) is in a range of about 0.01 mg/kg to about 100 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 20 mg/kg body weight, about 30 mg/kg body weight, about 40 mg/kg body weight, about 50 mg/kg body weight, about 60 mg/kg body weight, about 70 mg/kg body weight, about 80 mg/kg body weight, about 90 mg/kg body weight, or about 100 mg/kg body weight, inclusive of all values and ranges therebetween. In other embodiments, a suitable dosage of the beta-lactamases (and/or additional therapeutic agents) in a range of about 0.01 mg/kg to about 100 mg/kg of body weight, in a range of about 0.01 mg/kg to about 90 mg/kg of body weight, in a range of about 0.01 mg/kg to about 80 mg/kg of body weight, in a range of about 0.01 mg/kg to about 70 mg/kg of body weight, in a range of about 0.01 mg/kg to about 60 mg/kg of body weight, in a range of about 0.01 mg/kg to about 50 mg/kg of body weight, in a range of about 0.01 mg/kg to about 40 mg/kg of body weight, in a range of about 0.01 mg/kg to about 30 mg/kg of body weight, in a range of about 0.01 mg/kg to about 20 mg/kg of body weight, in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of about 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In accordance with certain embodiments of the invention, the beta-lactamase may be administered, for example, more than once daily, about once per day, about every other day, about every third day, about once a week, about once every two weeks, about once every month, about once every two months, about once every three months, about once every six months, or about once every year.

Additional Therapeutic Agents and Combination Therapy or Co-Formulation

Administration of the present formulations may be combined with additional therapeutic agents. Co-administration of the additional therapeutic agent and the present formulations may be simultaneous or sequential. Further, the present formulations may comprise an additional therapeutic agent (e.g. via co-formulation). For example, the additional therapeutic agent and the beta-lactamase may be combined into a single formulation.

In one embodiment, the additional therapeutic agent and the beta-lactamase are administered to a subject simultaneously. The term "simultaneously" as used herein, means that the additional therapeutic agent and the beta-lactamase are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the beta-lactamase can be by simultaneous administration of a single formulation (e.g., a formulation comprising the additional therapeutic agent and the beta-lactamase) or of separate formulations (e.g., a first formulation including the additional therapeutic agent and a second formulation including the beta-lactamase).

Co-administration does not require the additional therapeutic agents to be administered simultaneously, if the timing of their administration is such that the pharmacological activities of the additional therapeutic agent and the beta-lactamase overlap in time. For example, the additional therapeutic agent and the beta-lactamase can be administered sequentially. The term "sequentially" as used herein means that the additional therapeutic agent and the beta-lactamase are administered with a time separation of more than about 60 minutes. For example, the time between the sequential administration of the additional therapeutic agent and the beta-lactamase can be more than about 60 minutes, more than about 2 hours, more than about 5 hours, more than about 10 hours, more than about 1 day, more than about 2 days, more than about 3 days, or more than about 1 week apart. The optimal administration times will depend on the rates of metabolism, excretion, and/or the pharmacodynamic activity of the additional therapeutic agent and the beta-lactamase being administered. Either the additional therapeutic agent or the beta-lactamase may be administered first.

In a further embodiment, the additional therapeutic agent and the beta-lactamase are administered to a subject simultaneously but the release of additional therapeutic agent and the beta-lactamase from their respective dosage forms (or single unit dosage form if co-formulated) in the GI tract occurs sequentially.

Co-administration also does not require the additional therapeutic agents to be administered to the subject by the same route of administration. Rather, each additional therapeutic agent can be administered by any appropriate route, for example, parenterally or non-parenterally.

In some embodiments, the additional therapeutic agent is an anti-bacterial agent, which includes, but is not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin);

monobactam antibiotics (aztreonam); and carbapenem antibiotics (ertapenem, doripenem, imipenem/cilastatin, and meropenem). In some embodiments, any of the penicillins and cephalosporins described herein may be the additional therapeutic agent.

In some embodiments, the additional therapeutic agent is a beta-lactamase inhibitor. Exemplary beta-lactamase inhibitors include, for example, tazobactam, sulbactam, clavulanic acid, avibactam, monobactam derivatives, ATMO derivatives, penems (e.g., BRL42715 and derivatives thereof, Syn1012, oxapenems, trinems, 1-(3-methylcarbapenems), penicillin and cephalosporin sulfone derivatives (e.g., 0-2/C-3-substituted penicillin and cephalosporin sulfones, C-6-substituted penicillin sulfones), non-6-lactam inhibitors (e.g., boronic acid transition state analogs, phophonates, NXL104, hydroxmates) and metallo-6-lactamase inhibitors such as thiol derivatives, pyridine dicarboxylates, trifluoromethyl ketones and alcohols, carbapenem analogs, tricyclic natural products, succinate derivatives, and C-6-mercaptomethyl penicillinates.

In some embodiments, the additional therapeutic agent is an adjunctive therapy that is used in, for example, the treatment of CDI as described herein. In some embodiments, the additional therapeutic agent is metronidazole (e.g. FLAGYL), fidaxomicin (e.g. DIFICID), or vancomycin (e.g. Vancocin), rifaximin, charcoal-based binders/adsorbents (e.g. DAV132), fecal bacteriotherapy, probiotic therapy (see, e.g., *Intnat→l J Inf Dis,* 16 (11): e786, the contents of which are hereby incorporated by reference, illustrative probiotics include *Saccharomyces boulardii; Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus* (Bio-K+ CL1285); combination of *Lactobacillus casei, Lactobacillus bulgaricus, Streptococcus thermophilus* (Actimel); combination of *Lactobacillus acidophilus, Bifidobacterium bifidum* (Florajen3);

combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve, Streptococcus salivarius* subsp. *thermophilus* (VSL #3)) and antibody or other biologic therapy (e.g. monoclonal antibodies against *C. difficile* toxins A and B as described in N Engl J Med. 2010; 362(3):197, the contents of which are hereby incorporated by reference in their entirety; neutralizing binding proteins, for example, arranged as multimers, which are directed to one or more of SEQ ID NOs. recited in United States Patent Publication No. 2013/0058962 (e.g. one or more of SEQ ID Nos.: 59, 60, 95, 67, 68, and 87), the contents of which are hereby incorporated by reference); or any neutralizing binding protein directed against *C. difficile* binary toxin.

In some embodiments, the additional therapeutic agent is an antidiarrheal agent. Antidiarrheal agents suitable for use in the present invention include, but are not limited to, DPP-IV inhibitors, natural opioids, such as tincture of opium, paregoric, and codeine, synthetic opioids, such as diphenoxylate, difenoxin and loperamide, bismuth subsalicylate, lanreotide, vapreotide and octreotide, motiln antagonists, COX2 inhibitors like celecoxib, glutamine, thalidomide and traditional antidiarrheal remedies, such as kaolin, pectin, berberine and muscarinic agents.

In some embodiments, the additional therapeutic agent is an anti-inflammatory agent such as steroidal anti-inflammatory agents or non-steroidal anti-inflammatory agents (NSAIDS). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluorometholone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. Additional anti-inflammatory agents are described, for example, in U.S. Pat. No. 4,537,776, the entire contents of which is incorporated by reference herein.

In some embodiments, the additional therapeutic agent may be an analgesic. Analgesics useful in the compositions and methods of the present invention include, without limitation, morphine, codeine, heroine, methadone and related compounds, thebaine, orpiavine, and their derivatives, buprenorphine, the piperidines, morphinans, benzomorphans, tetrahydroisoquinolines, thiambutanes, benzylamines, tilidine, viminol, nefopam, capsaicin(8-methyl-N-vanillyl-6E-nonenamide), "synthetic" capsaicin(N-vanillylnonamide), and related compounds.

In some embodiments, the additional therapeutic agent may be an anti-viral agent that includes, but is not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet.

For all additional therapeutic agent compositions and methods, targeting to various parts of the GI tract may be employed as described herein.

In some embodiments, the present formulations are administered to a subject to avoid treatment with an additional therapeutic agent. For example, in the context of preventing C. difficile infection (CDI) and/or a C. difficile-associated disease, the present formulations may be provided to a subject to avoid the necessity of receiving, for example, vancomycin.

Methods of Treatment

In various aspects, the present invention provides methods for protecting a subject's gastrointestinal microbiome, comprising administering an effective amount of a pharmaceutical composition comprising a beta-lactamase, for example, any of the formulations described herein, to a subject who is undergoing treatment or has recently undergone treatment with an oral antibiotic. The beta-lactamase is capable of deactivating (by way of non-limitation, hydrolyzing) the oral antibiotic. In various embodiments, the oral antibiotic is one or more of a ceftriaxone, cefotaxime, cefazolin, cefoperazone, cefuroxime, and piperacillin.

In various embodiments, the subjects include, but are not limited to, subjects that are at a particular risk for a microbiome-mediated disorder, such as those undergoing treatment or has recently undergone treatment with an oral antibiotic. For example, the subject may be taking an oral antibiotic during the past 30 or so days and/or have an immune system that is weak (e.g. from a chronic illness) and/or are women and/or are elderly (e.g. over about 65 years old) and/or are elderly woman and/or undergo treatment with for heartburn or stomach acid disorders (e.g. with agents such as PREVACID, TAGAMET, PRILOSEC, or NEXIUM and related drugs) and/or have recently been in the hospital, including in an intensive care unit, or live in a nursing home. Accordingly, in some embodiments, the methods and uses of the present invention treat or prevent a nosocomial infection and/or a secondary emergent infection and/or a hospital acquired infection (HAI).

In some embodiments, the methods and uses of the present invention include those in which an initial and/or adjunctive therapy is administered to a subject. Initial and/or adjunctive therapy indicates therapy that is used to treat for example, a microbiome-mediated disorder or disease upon detection of such disorder or disease. In some embodiments, the initial and/or adjunctive therapy is one or more of metronidazole, vancomycin, fidaxomicin, rifaximin, charcoal-based binder/adsorbent, fecal bacteriotherapy, probiotic therapy, and antibody therapy, as described herein. In various embodiments, the methods and uses of the present invention include use of the pharmaceutical compositions and formulations including beta-lactamase (and/or additional therapeutic agent) as an adjuvant to any of these initial and/or adjunctive therapies (including co-administration or sequential administration). In various embodiments, the methods and uses of the present invention include use of the pharmaceutical compositions and formulations including beta-lactamase (and/or additional therapeutic agent) in a subject undergoing initial and/or adjunctive therapies.

In some embodiments, the methods and uses of the present invention include those in which an oral antibiotic and a beta-lactamase inhibitor are administered to a subject. In various embodiments, the subject may be receiving a co-formulation of an oral antibiotic with one or more beta-lactamase inhibitors (e.g. Augmentin is a mixture of amoxicillin and clavulanic acid). Such co-formulations include, but are not limited to, amoxicillin-clavulanic acid (Augmentin, ticarcillin-clavulanic acid (Timentin), ampicillin-sulbactam (Sultamicillin, e.g. Unasyn), piperacillin-tazobactam (Zosyn), and cefoperazone-sulbactam. In various embodiments, methods of the present invention comprise further administering a beta-lactamase inhibitor that releases in the GI tract proximal to the beta-lactamase. In an embodiment, the beta-lactamase inhibitor may be released at various parts of the GI tract where the oral antibiotic may be active. For example, the beta-lactamase inhibitor may be released at the stomach, duodenum, jejunum and ileum.

Exemplary beta-lactamase inhibitors include, for example, tazobactam, sulbactam, clavulanic acid, avibactam, monobactam derivatives, ATMO derivatives, penems (e.g., BRL42715 and derivatives thereof, Syn1012, oxapenems, trinems, 1-(3-methylcarbapenems), penicillin and cephalosporin sulfone derivatives (e.g., C-2/C-3-substituted penicillin and cephalosporin sulfones, C-6-substituted penicillin sulfones), non-β-lactam inhibitors (e.g., boronic acid transition state analogs, phophonates, NXL104, hydroxmates) and metallo-β-lactamase inhibitors such as thiol derivatives, pyridine dicarboxylates, trifluoromethyl ketones and alcohols, carbapenem analogs, tricyclic natural products, succinate derivatives, and C-6-mercaptomethyl penicillinates.

In various embodiments, the methods of the invention comprise treating or preventing a microbiome-mediated disorder. Illustrative microbiome-mediated disorder includes, but are not limited to, for example, those found in Table 3 of WO2014/121298, the entire contents of which are incorporated herein by reference. For example, the microbiome-mediated disorder may be selected from an antibiotic-induced adverse effect, a *C. difficile* infection (CDI), a *C. difficile*-associated disease, ulcerative colitis, Crohn's disease, and irritable bowel syndrome. In various embodiments, the microbiome-mediated disorder is an antibiotic-induced adverse effect, a *C. difficile* infection (CDI), or a *C. difficile*-associated disease. In an embodiment, the present invention provides methods for treating an antibiotic-induced adverse effect in the GI tract, comprising administering an effective amount of a pharmaceutical composition or formulation including beta-lactamase (and/or additional therapeutic agent) described herein to a subject who is undergoing treatment or has recently undergone treatment with an oral antibiotic. In another embodiment, the present invention provides methods for preventing an antibiotic-induced adverse effect in the GI tract, comprising administering an effective amount of a pharmaceutical composition or formulation including beta-lactamase (and/or additional therapeutic agent) described herein to a subject who is undergoing treatment or has recently undergone treatment with an oral antibiotic.

In an embodiment, the present invention provides methods for treating *C. difficile* infection (CDI) and/or a *C. difficile*-associated disease, comprising administering an effective amount of a pharmaceutical composition or formulation including beta-lactamase (and/or additional therapeutic agent) described herein to a subject who is undergoing treatment or has recently undergone treatment with an oral antibiotic. In another embodiment, the present invention provides methods for preventing *C. difficile* infection (CDI) and/or a *C. difficile*-associated disease, comprising administering an effective amount of a pharmaceutical composition or formulation including beta-lactamase (and/or additional therapeutic agent) described herein to a subject who is undergoing treatment or has recently undergone treatment with an oral antibiotic.

In various embodiments, the present invention relates to methods of preventing and/or reducing the likelihood that a subject becomes afflicted with an antibiotic-associated adverse effect (e.g. *Clostridium difficile* infection, antibiotic associated diarrhea) by administering an effective amount of a beta-lactamase formulation as described herein, such as those presented in TABLES 1, 5, 7, and 8. In some embodiments, the formulation, optionally, in the form of a capsule (e.g., a hard gelatin or HPMC capsule) comprises a plurality of enteric-coated beta-lactamase-containing pellets. In some embodiments, the formulation, optionally, in the form of a capsule (e.g., a hard gelatin or HPMC capsule) comprises a plurality of beta-lactamase-containing pellets coated with an osmotic rupture coating.

In some embodiments, the beta-lactamase-containing pellets (or each individual pellet) comprises a beta-lactamase (e.g. P3A, or the other beta-lactamase agents described herein, and variants thereof), a sucrose sphere, which the beta-lactamase, for example, P3A or a variant, is sprayed onto, a binder excipient (e.g., hydroxypropylcellulose (HPC)), an enteric polymer (e.g., EUDRAGIT L 30 D-55), a plasticizer (e.g., triethyl citrate), a glidant (e.g., glyceryl monostearate), an emulsifier, and buffer salts, where to subject is receiving an oral beta-lactam antibiotic which is a substrate of the beta-lactamase. In various embodiments, the above method involves a formulation, optionally in the form of a capsule e.g., a hard gelatin or HPMC capsule) comprising a plurality of enteric-coated beta-lactamase-containing pellets, the pellets (or each individual pellet) comprising about 10-20% by weight of beta-lactamase (e.g. P3A, or the other beta-lactamase agents described herein, and variants thereof). For example, the beta-lactamase (e.g. P3A, or the other beta-lactamase agents described herein, and variants thereof) may be present at about 10%, about 11%, about 12%, about 13%, about 14%, about 15%, about 16%, about 17%, about 18%, about 19%, or about 20% by weight. In some embodiments, the pellets (or each individual pellet) comprise about 20-30% by weight sucrose sphere, which the beta-lactamase, for example, P3A or a variant, is sprayed onto. For example, the sucrose sphere may be present at about 20%, about 21%, about 22%, about 23%, about 24%, about 25%, about 26%, about 27%, about 28%, about 29%, or about 30% by weight. In various embodiments, the pellets (or each individual pellet) comprise about 30-40% by weight a binder excipient (e.g., hydroxypropylcellulose (HPC)). For example, the binder excipient may be present at about 30%, about 31%, about 32%, about 33%, about 34%, about 35%, about 36%, about 37%, about 38%, about 39%, or about 40% by weight. In some embodiments, the pellets (or each individual pellet) comprise about 15-25% by weight an enteric polymer (e.g., EUDRAGIT L 30 D-55). For example, the enteric polymer may be present at about 15%, about 16%, about 17%, about 18%, about 19%, about 20%, about 21%, about 22%, about 23%, about 24%, or about 25% by weight. In some embodiments, the pellets (or each individual pellet) comprise about 1.5-2.5% by weight of plasticizer (e.g., triethyl citrate). For example, the plasticizer may be present at about 1.5%, about 1.6%, about 1.7%, about 1.8%, about 1.9%, about 2%, about 2.1%, about 2.2%, about 2.3%, about 2.4%, about 2.5% by weight. In some embodiments, the pellets (or each individual pellet) comprise about 0.5-1.5% by weight glidant (e.g., glyceryl monostearate). For example, the glidant may be present at about 0.5%, about 0.6%, about 0.7%, about 0.8%, about 0.9%, about 1%, about 1.1%, about 1.2%, about 1.3%, about 1.4%, or about 1.5% by weight. In some embodiments, the pellets (or each individual pellet) comprise about 0.1-1.0% by weight emulsifier (e.g. polysorbate-80). For example, the emulsifier may be present at about 0.1%, about 0.2%, about 0.3%, about 0.4%, about 0.5%, about 0.6%, about 0.7%, about 0.8%, about 0.9%, or about 1% by weight. In some embodiments, the pellets (or each individual pellet) further comprise about 1-2% by weight buffer salts. For example, the buffer salts may be present at about 1.1%, about 1.2%, about 1.3%, about 1.4%, about 1.5%, about 1.6%, about 1.7%, about 1.8%, about 1.9%, or about 2% by weight. The weight as described herein refers to the total weight of all components excluding the weight of the capsule itself. In various embodiments, the above method involves a formulation, optionally in the form of a pellet (or each individual pellet) comprising about 16% by weight of the beta-lactamase (e.g. P3A, or the other beta-lactamase agents described herein, and variants thereof); about 23% by weight sucrose sphere; about 35% by weight a binder excipient (e.g., hydroxypropylcellulose (HPC)); about 21% by weight an enteric polymer (e.g., EUDRAGIT L 30 D-55); about 2% by weight of plasticizer (e.g., triethyl citrate); about 1% by weight glidant (e.g., glyceryl monostearate); about 0.5% by weight emulsifier (e.g. polysorbate-80); and about 2% by weight buffer salts. The weight as described herein refers to the total weight of all components excluding the weight of the capsule itself. For example, the pellets (or each individual pellet) comprise about 15.8% by weight of the beta-lactamase (e.g. P3A, or the other beta-lactamase agents described herein, and variants thereof); about 23.3% by weight sucrose sphere; about 35% by weight a binder excipient (e.g., hydroxypropylcellulose (HPC)); about 20.8% by weight an enteric polymer (e.g., EUDRAGIT L 30 D-55); about 2.1% by weight of plasticizer (e.g., triethyl citrate); about 1.0% by weight glidant (e.g., glyceryl monostearate); about 0.4% by weight emulsifier (e.g. polysorbate-80); and about 1.6% by weight buffer salts. The weight as described herein refers to the total weight of all components excluding the weight of the capsule itself.

In various embodiments, the antibiotic-induced adverse effect and/or CDI or *C. difficile*-associated disease is one or more of: antibiotic-associated diarrhea, *C. difficile* diarrhea (CDD), *C. difficile* intestinal inflammatory disease, colitis, pseudomembranous colitis, fever, abdominal pain, dehydration and disturbances in electrolytes, megacolon, peritonitis, and perforation and/or rupture of the colon. Additional diseases, disorders and conditions which are suitable for treatment with the compositions and methods of the invention include those listed in Table 3 of WO2014/121298, the entire contents of which are incorporated herein by reference.

In various embodiments, the present uses and methods pertain to co-treatment (simultaneously or sequentially) with the pharmaceutical composition or formulation including beta-lactamase (and/or additional therapeutic agent) described herein and/or any initial and/or adjunctive therapy, or treatment with a co-formulation of the pharmaceutical composition or formulation including beta-lactamase (and/or any additional therapeutic agent) described herein and/or any initial and/or adjunctive therapy for treatment of the various diseases described herein.

In various embodiments, the microbiome-mediated disorder is treated or prevented in the context of initial onset or relapse/recurrence (e.g. due to continued or restarted antibiotic therapy). For example, in a subject that has previously suffered from a microbiome-mediated disorder (e.g., CDI), the present pharmaceutical composition or formulation including beta-lactamase (and/or additional therapeutic agent) may be administered upon the first symptoms of recurrence in the subject. By way of non-limiting example, symptoms of recurrence include, in a mild case, about 5 to about 10 watery bowel movements per day, no significant fever, and only mild abdominal cramps while blood tests may show a mild rise in the white blood cell count up to about 15,000 (normal levels are up to about 10,000), and, in a severe case, more than about 10 watery stools per day, nausea, vomiting, high fever (e.g. about 102-104° F.), rectal bleeding, severe abdominal pain (e.g. with tenderness), abdominal distention, and a high white blood count (e.g. of about 15,000 to about 40,000).

Regardless of initial onset or relapse/recurrence, the microbiome-mediated disorder may be diagnosed via any of the symptoms described herein (e.g. watery diarrhea about 3 or more times a day for about 2 days or more, mild to bad cramping and pain in the belly, fever, blood or pus in the stool, nausea, dehydration, loss of appetite, loss of weight, etc.). Regardless of initial onset or relapse/recurrence, the microbiome-mediated disorder may also be diagnosed via enzyme immunoassays (e.g. to detect the *C. difficile* toxin A or B antigen and/or glutamine dehydrogenase (GDH), which is produced by *C. difficile* organisms), polymerase chain reactions (e.g., to detect the *C. difficile* toxin A or B gene or a portion thereof (e.g. tcdA or tcdB), including the ILLUMIGENE LAMP assay), a cell cytotoxicity assay. For example, any of the following tests may be used: Meridian ImmunoCard Toxins NB; Wampole Toxin NB Quik Chek; Wampole C. diff Quik Chek Complete; Remel Xpect *Clostridium difficile* Toxin NB; Meridian Premier Toxins A/B; Wampole *C. difficile* Tox NB II; Remel Prospect Toxin A/B EIA; Biomerieux Vidas *C. difficile* Toxin A&B; BD Geneohm C. Prodesse Progastro CD; and Cepheid Xpert C. diff. In various embodiments, the clinical sample is a subject's stool sample.

Also a flexible sigmoidoscopy "scope" test and/or an abdominal X-ray and/or a computerized tomography (CT) scan, which provides images of your colon, may be used in assessing a subject (e.g. looking for characteristic creamy white or yellow plaques adherent to the wall of the colon). Further, biopsies (e.g. of any region of the GI tract) may be used to assess a potential microbiome-mediated disorder (e.g., CDI and/or *C. difficile* associated disease) in subject.

In various embodiments, the methods and uses of the present invention relate to pharmaceutical compositions and formulations including beta-lactamase (and/or additional therapeutic agent) which release the beta-lactamase (and/or additional therapeutic agent) in a location in the GI tract in which it deactivates excess oral antibiotic residue. In an embodiment, the methods and uses of the present invention relate to pharmaceutical compositions and formulations including beta-lactamase (and/or additional therapeutic agent) which deactivate excess oral antibiotic residue before it enters the GI tract, including the small and/or large intestine. In an embodiment, the methods and uses of the present invention relate to pharmaceutical compositions and formulations including beta-lactamase (and/or additional therapeutic agent) which deactivate excess oral antibiotic residue before it enters the large intestine. In an embodiment, the methods and uses of the present invention relate to pharmaceutical compositions and formulations including beta-lactamase (and/or additional therapeutic agent) which deactivate excess oral antibiotic residue in the GI tract. In various embodiments, the pharmaceutical compositions and formulations including beta-lactamase (and/or additional therapeutic agent) as described herein releases the beta-lactamase (and/or additional therapeutic agent) in a location in the GI tract that is distal to the release of the oral antibiotic. In various embodiments, the beta-lactamase (and/or additional therapeutic agent) is released in a location in the GI tract where it prevents a microbicidal activity of the residual or excess oral antibiotic (e.g. active antibiotic that is not absorbed from the GI tract after an oral dose or is returned in active form to the intestinal tract from the systemic circulation) on GI tract microbiota.

In some embodiments, methods and uses of the present invention relate to pharmaceutical compositions and formulation including beta-lactamase (and/or additional therapeutic agent) which maintain a normal intestinal microbiota and/or prevent the overgrowth of one or more pathogenic microorganisms in the GI tract of a subject. In various embodiments, the present invention provides for pharmaceutical compositions and methods that mitigate or prevent the overgrowth of various coliforms in a subject's gut (including coliforms that are virulent and/or antibiotic resistant). In various aspects, the methods, pharmaceutical compositions and formulations described herein prevent or diminish secondary infections with resistant organisms and may, in some embodiments, diminish beta-lactam resistance development. Further, the methods, pharmaceutical compositions and formulations described herein may allow for use of beta-lactam antibiotics which are currently avoided due to resistance concerns and/or reduce the need for co-administration or co-formulation with one or more beta-lactamase inhibitors (e.g. Augmentin, Sultamicillin).

In various embodiments, the beta-lactamases and/or pharmaceutical compositions (and/or additional therapeutic agents) do not substantially interfere with blood or plasma levels of an oral antibiotic. For example, the beta-lactamases and/or pharmaceutical compositions (and/or additional therapeutic agents) of the present invention allow for a subject to receive an oral antibiotic that might be required for an infection and do not interfere with the systemic activity of the oral antibiotic or the time above minimum inhibitory concentrations of the antibiotic in the plasma. In an embodiment, the beta-lactamases and/or pharmaceutical compositions (and/or additional therapeutic agents) does not substantially interfere with blood or plasma levels of the oral antibiotic. Rather, the beta-lactamases and/or pharmaceutical compositions (and/or additional therapeutic agents) inactivate residual or excess oral antibiotic (e.g. active antibiotic that is not absorbed from the GI tract after an oral dose or is returned in active form to the intestinal tract from the systemic circulation) that may populate parts of the GI tract and in doing so, prevent the disruption of the microbiota that is linked to the various disease states described herein.

In various embodiments, the pharmaceutical compositions and formulations including beta-lactamase and/or additional therapeutic agent are not systemically absorbed. In some embodiments, the compositions and formulations including beta-lactamase (and/or additional therapeutic agent) do not interfere with the antibiotic absorption from the gut and/or or antibiotic enterohepatic recirculation enough to be clinically important.

In various embodiments, the pharmaceutical compositions and formulations including beta-lactamase and/or additional therapeutic agent are used as an adjuvant for the treatment of *H. pylori* infection, e.g. in the gastric mucosa. For instance, the present pharmaceutical compositions and formulations may be used as adjuvant to amoxicillin treatments (e.g. as an adjuvant to "triple therapy" (e.g. proton pump inhibitors such as omeprazole, pantoprazole, or rabeprazole and the antibiotics clarithromycin and amoxicillin, or metronidazole)). By way of example, the amoxicillin would be administered such that it is delivered to the stomach where it has a therapeutic effect and then it is deactivated upon exiting the stomach by the pharmaceutical compositions and formulations (e.g. duodenally-released). Accordingly, provided herein are methods of treating or preventing *H. pylori* infection in a subject's stomach by administering a pharmaceutical compositions and formulations including beta-lactamase and/or additional therapeutic agent described herein. Further, the present methods are useful in treating or preventing an *H. pylori* infection-related disease (by way of non-limiting example: ulcers (e.g. duodenal ulcers, peptic ulcer disease), cancers (e.g. stomach cancer, gastric MALT lymphoma), and dyspepsia). In some of these embodiments, there is no requirement to preserve a systemic level of oral antibiotic.

In some embodiments, the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell.

In various embodiments, methods of the invention are useful in treatment a human subject. In some embodiments, the human is a pediatric human. In other embodiments, the human is an adult human. In other embodiments, the human is a geriatric human. In other embodiments, the human may be referred to as a subject. In some embodiments, the human is a female. In some embodiments, the human is a male.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old. In one embodiment, the human is a child. In one embodiment, the human is a female.

In other embodiments, the subject is a non-human animal, and therefore the invention pertains to veterinary use. In a specific embodiment, the non-human animal is a household pet. In another specific embodiment, the non-human animal is a livestock animal.

Kits

The invention provides kits that can simplify the administration of any agent described herein. An exemplary kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional therapeutic agents described herein. In one embodiment, the kit comprises a container containing an effective amount of a composition of the invention and an effective amount of another composition, such those described herein.

In some embodiments, the additional therapeutic agent is an adjunctive therapy that is used in, for example, the treatment of CDI as described herein. In some embodiments, the additional therapeutic agent is metronidazole (e.g. FLAGYL), fidaxomicin (e.g. DIFICID), or vancomycin (e.g. Vancocin), rifaximin, fecal bacteriotherapy, charcoal-based binders/adsorbents (e.g. DAV132), probiotic therapy (see, e.g., *Intnat'l J Inf Dis,* 16 (11): e786, the contents of which are hereby incorporated by reference, illustrative probiotics include *Saccharomyces boulardii; Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus* (Bio-K+CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve, Streptococcus salivarius* subsp. *thermophilus* (VSL #3)) and antibody or other biologic therapy (e.g. monoclonal antibodies against *C. difficile* toxins A and B as described in N Engl J Med. 2010; 362(3):197, the content of which are hereby incorporated by reference in their entirety; neutralizing binding proteins, for example, arranged as multimers, which are directed to one or more of SEQ ID NOs. recited in United States Patent Publication No. 2013/0058962 (e.g. one or more of SEQ ID Nos.: 59, 60, 95, 67, 68, and 87), the contents of which are hereby incorporated by reference); or any neutralizing binding protein directed against *C. difficile* binary toxin. In some embodiments, any of the penicillins and cephalosporins described herein may be the additional therapeutic agent.

EXAMPLES

Example 1. SYN-004 Microbiome Protection from Oral Amoxicillin Microbiome Damage SYN-004 was formulated as an enteric-coated pellet that releases at pHs of 5.5 and higher. Therefore, SYN-004 is protected from low pH, similar to what is found in the stomach, and released at pHs greater than 5.5, similar to the pH in the duodenum (pH 5.9-6.6). Release of SYN-004 is expected to continue throughout the small intestine, i.e., the jejunum (pH 6.6-7.4), the ileum (pH 7.3-7.8), and/or cecum (pH 5.6-5.9).

The formulation used for this study is as follows:

TABLE 1

Composition of P3A Delayed-Release Capsules, 75 mg and 25 mg, and Placebo Capsule

| Component | 75 mg Capsule | | 25 mg Capsule | | Placebo Capsule | |
|---|---|---|---|---|---|---|
| | mg | % Total | mg | % Total | mg | % Total |
| Sucrose sphere | 110.8 | 23.3 | 36.9 | 23.3 | 139.8 | 29.5 |
| Hydroxypropylcellulose | 166.3 | 35.0 | 55.4 | 35.0 | 209.6 | 44.2 |
| EUDRAGIT ® L 30 D-55 | 98.9 | 20.8 | 33.0 | 20.8 | 98.7 | 20.8 |
| P3A | 75.0 | 15.8 | 25.0 | 15.8 | — | — |
| Buffer salts | 7.5 | 1.6 | 2.5 | 1.6 | 9.4 | 2.0 |
| Glyceryl monostearate | 4.9 | 1.0 | 1.6 | 1.0 | 4.9 | 1.0 |
| Polysorbate-80 | 2.0 | 0.4 | 0.7 | 0.4 | 2.0 | 0.4 |
| Triethyl citrate | 9.9 | 2.1 | 3.3 | 2.1 | 9.9 | 2.1 |
| Subtotal | 475.3 | 100.0 | 158.4 | 100.0 | 474.3 | 100.0 |
| Hard gelatin capsule #0 or Hydroxypropyl methylcellulose (HPMC) capsule | 96.0 | | 96.0 | | 96.0 | |
| Total | 571.3 | | 254.4 | | 570.3 | | and as described in PCT/US15/54606, the entire contents of which are incorporated by reference.

In vitro dissolution studies revealed that the current formulation of SYN-004 is released in a pH-dependent manner and requires 1-3 hours for complete release, while transit time through the small intestine is approximately 3 hrs+1 hr SEM after entering the duodenum. See, e.g. U.S. patent application Ser. No. 14/878,155, the entire contents of which are hereby incorporated by reference. These data suggest that SYN-004 will be released in a sustained manner throughout the proximal and distal small intestine. Orally-delivered antibiotics such as amoxicillin are absorbed in the proximal small intestine such as the duodenum and the jejunum, but not in the ileum (Barr, et al., 1994).

A study was performed using normal piglets to determine if SYN-004, when delivered orally with oral amoxicillin, functions to protect the microbiome from amoxicillin-induced dysbiosis. The study also tested if SYN-004 affected the absorption of amoxicillin from the GI tract of animals (TABLE 2).

TABLE 2

Piglet study design

| Group (N = 5) | Antibiotic | Antibiotic Delivery | SYN-004 |
|---|---|---|---|
| 1<br>Pig 1,2,3,4,5 | Amoxicillin suspension (40 mg/kg/day) | Oral, BID, each 20 mg/kg<br>7 am, 5 pm | None |
| 2<br>Pig 6,7,8,9,10 | Amoxicillin suspension (40 mg/kg/day) | Oral, BID, each 20 mg/kg<br>7 am, 5 pm | 1 size 0 capsule (75 mg), QID<br>7 am, 12 pm,<br>5 pm, 10 pm |

Figure 1:
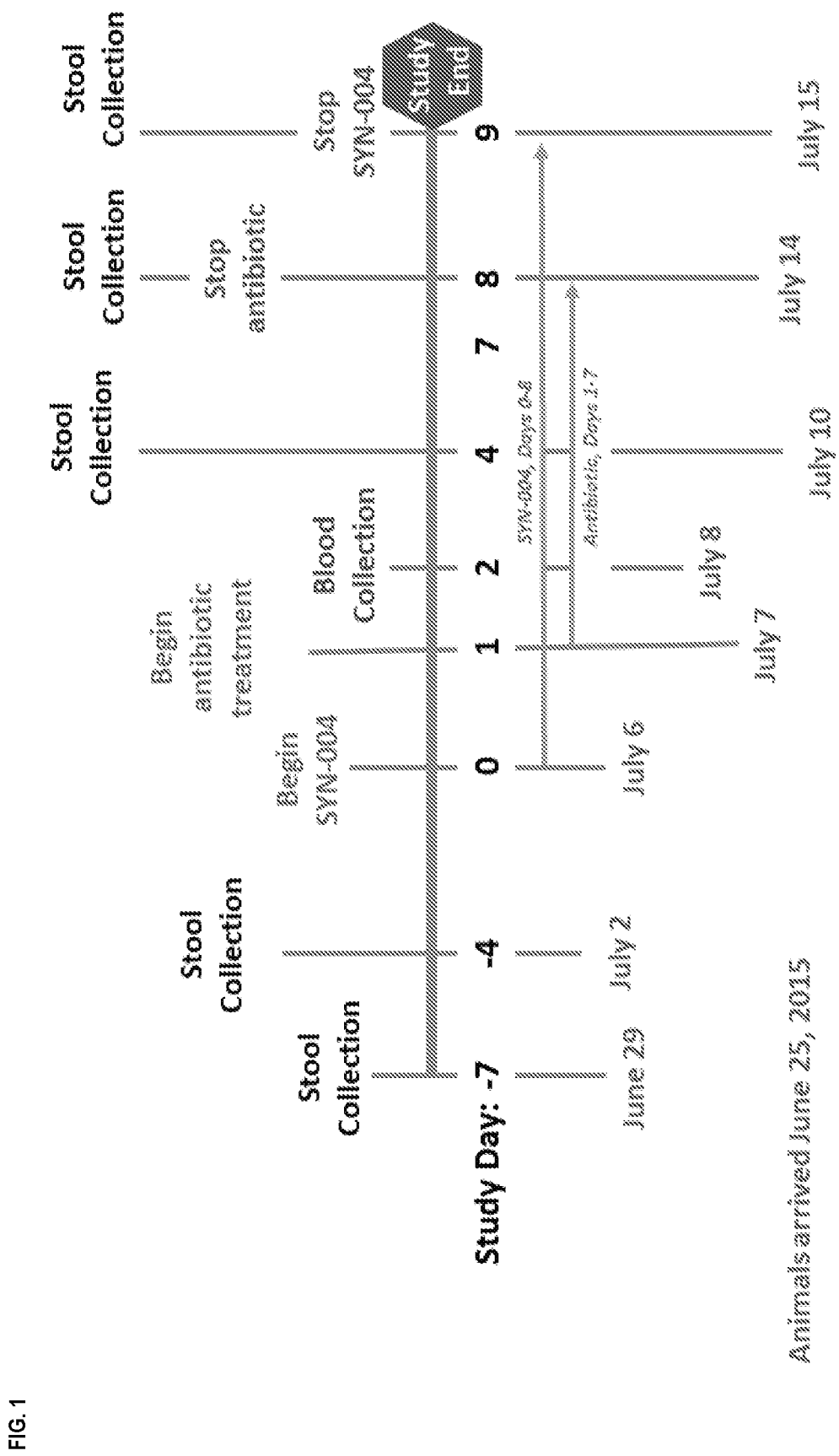
FIG. 1 shows a timeline of piglet dosing for the study of Example 1.

A total of ten, two-month old Yorkshire piglets, approximately 20 kg each, were used for this study. All 10 animals were treated with oral amoxicillin twice a day for a total of 7 days, and one cohort of 5 animals was also treated with oral SYN-004 four times a day for a total of 9 days. The SYN-004 treatment was started the day before amoxicillin treatment and continued for a day after amoxicillin was stopped (FIG. 1).

Two pre-treatment fecal samples were obtained, the first 4 days after the animals arrived at the animal treatment facility (Day −7), and the second 7 days after arrival (Day −4). An additional 3 fecal samples were collected at Day 4, Day 8, and Day 9. The fecal samples were collected using the OMNIgene GUT sample collection kits (OMR-200, DNA Genotek, Ontario, Canada) and stored at room temperature away from light until all samples were collected. DNA isolated from the fecal samples was subjected to deep sequencing of the intestinal microbiome and analyses.

On Study Day 0, Group 2 (Pigs 6-10) received one size 0 capsule of SYN-004, containing 75 mg of SYN-004, orally, four times a day at 7 am, 12 μm, 5 μm, and 10 μm for a total of 9 days. Pigs were fed 3 times a day, after SYN-004 dosing at 7 am, after SYN-004 dosing at 12 μm, and after SYN-004 dosing at 5 μm. Beginning on Study Day 1, Groups 1 and 2 (Pigs 1-10) received oral amoxicillin (fruit flavored oral suspension, Sandoz, NDC: 0781-6157-46, Lot #EY9130; 20 mg/kg) twice a day at 7 am and at 5 μm, for a total of 7 days. Animals received the amoxicillin first, followed by the SYN-004, then feeding.

On Day 2, after 4 amoxicillin doses, animals were bled and serum collected. Blood was collected aseptically from the vena cava from anesthetized animals. Three blood draws were performed, at 1 hr, 3 hrs, and 8 hrs after amoxicillin administration. A Telazol cocktail was administered intramuscularly at a minimal dose (1 mL or less per 50 lbs) to achieve light anesthesia/sedations. At each timepoint, approximately 9 mL of blood was collected into a serum separator vacutainer tube. After coagulation, samples were centrifuged and the serum was transferred to a cryovial and stored at −80° C. until shipment to the evaluation laboratory (Center for Anti-Infective Research and Development, Hartford Hospital, Hartford, Conn.).

FIG. 1 shows a timeline of piglet dosing. Animals received SYN-004 for 9 days starting on Day 0. Animals received oral amoxicillin for 7 days starting on Day 1. Stool was collected at 5 times, Day −7, Day −4, Day 4, Day 8, and Day 9. Blood was collected at 3 times during Day 2.

Figure 2:
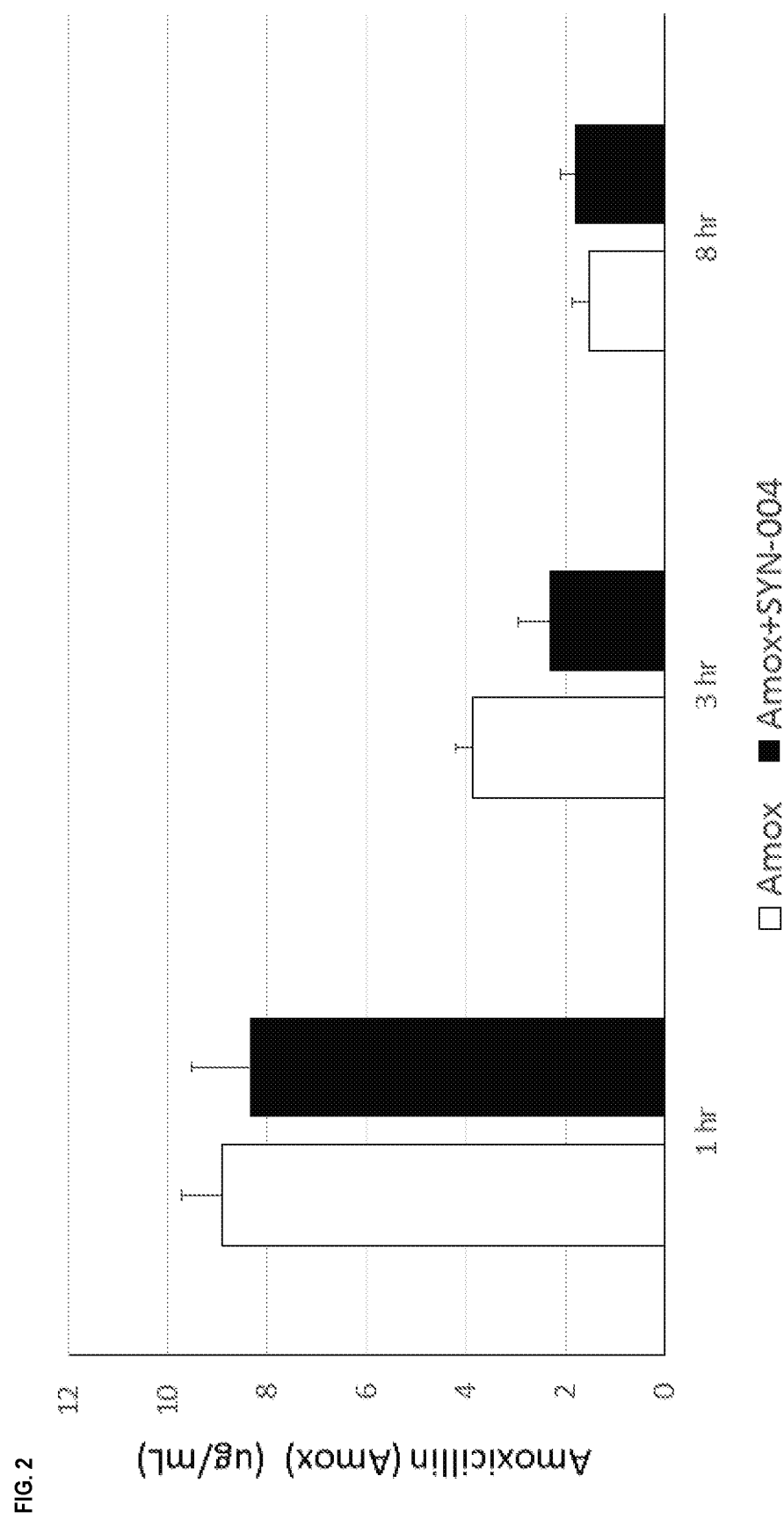
FIG. 2 shows amoxicillin levels in the pig serum from the study of Example 1.

Amoxicillin levels in the pig serum were quantified using a modification of a validated HPLC-based assay (Du et al., 2005). A standard curve was prepared in negative control pig serum and had 6 points ranging from 1 to 30 ug/mL of amoxicillin. The assay was linear over a range of 1 to 30 ug/mL ($R=0.999$). Interday coefficients of variation for the low (1.5 ug/mL) and high (20 ug/mL) quality control samples were 3.9% and 4.9% respectively. Interday coefficients of variation were 3.8% and 2.8%, respectively. Peak height was used to integrate all the peaks. Sigma Plot was used to calculate drug concentrations and a −1 weighting factor was used. An interfering peak was overcome by raising the standard curve from 0.25 to 1 ug/mL for the amoxicillin. The limit of detection of the assay was 1.5 ug/mL. The amoxicillin levels were reported as the mean and standard deviation (FIG. 2). The amoxicillin levels at one hour were 8.9±0.8 for amoxicillin alone and 8.4±1.2 for amoxicillin+SYN-004. At 3 hours, the amoxicillin levels were 3.9±0.3 for the amoxicillin alone and 2.3±0.6 for the amoxicillin+SYN-004. At 8 hours, the amoxicillin levels were 1.5±0.3 for the amoxicillin alone, and 1.8±0.3 for the amoxicillin+SYN-004. These data demonstrate that oral SYN-004 did not prevent the absorption of amoxicillin from the GI tract. Therefore, these data verify that SYN-004 did not degrade the amoxicillin in the GI tract prior to amoxicillin absorption, suggesting that the amoxicillin was absorbed before SYN-004 was released into the GI tract.

DNA was isolated from the fecal samples and subjected to whole genome shotgun sequencing using an Illumine HiSeq system with a target of 20 million 100 bp single reads per sample.

Sequenced datasets were taxonomically classified using the GENIUS® software package (Hasan et al., 2014, Lax et al., 2014).

Figure 3:
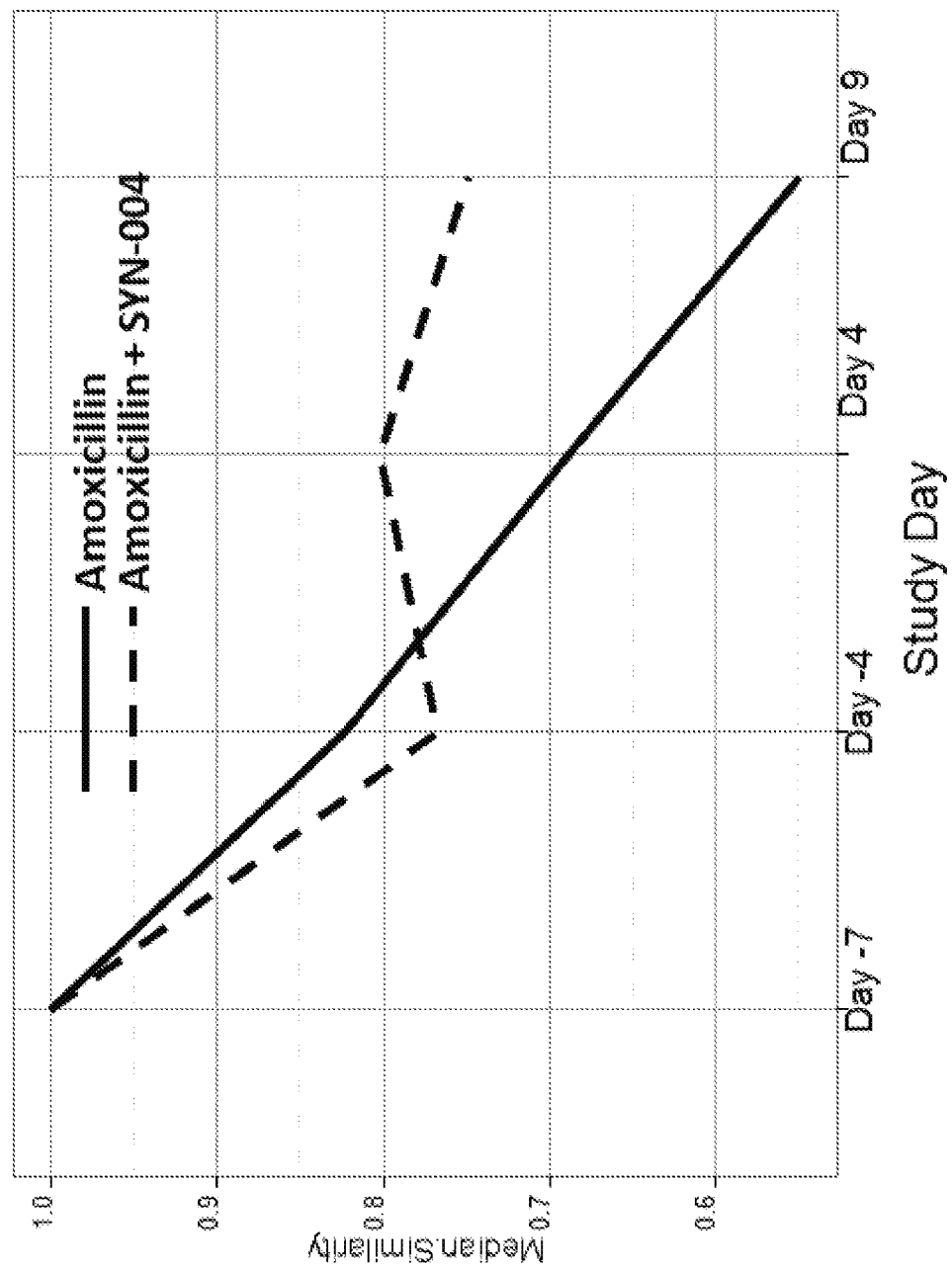
FIG. 3 shows strain relative abundance percent similarity from the sequencing analysis of Example 1. Amoxicillin alone is displayed as the solid line, and Amoxicillin+P3A or SYN-004 (synonyms for the same enzyme) is displayed as the dashed line.
Figure 4:
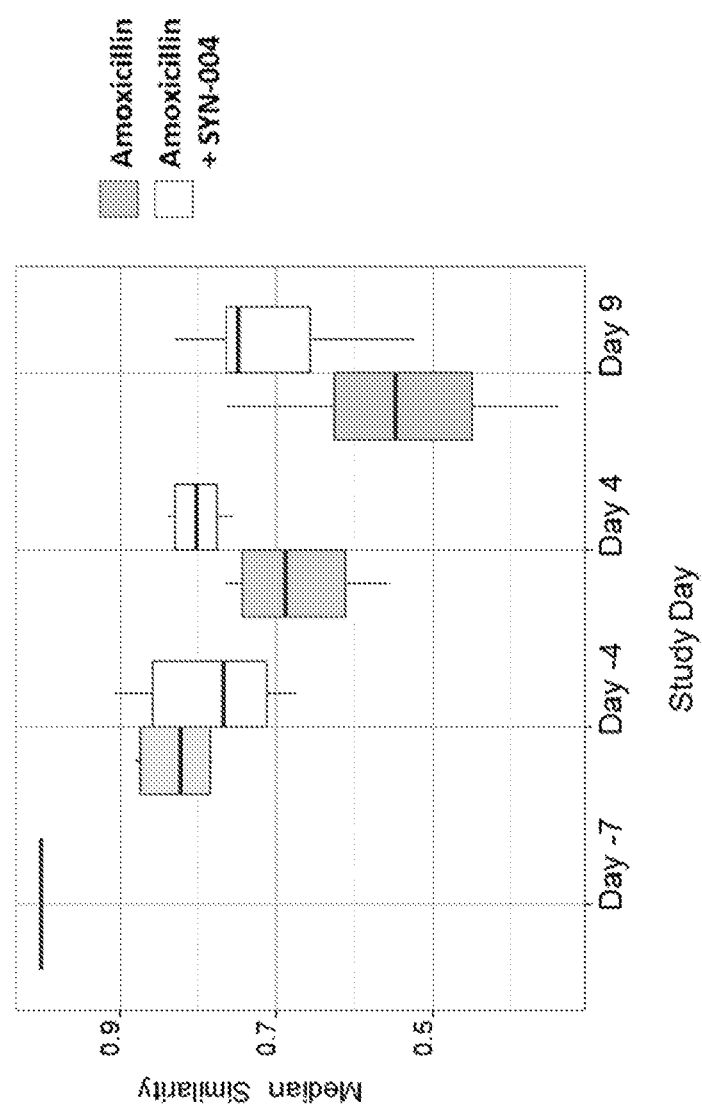
FIG. 4 shows strain relative abundance percent similarity boxplot from the sequencing analysis of Example 1. Amoxicillin alone is displayed as the gray box, and Amoxicillin+

The median similarity based on the relative bacterial strain abundance was calculated. The percent similarity from Day −7 to Day 9 of the amoxicillin and amoxicillin+SYN-004 groups was compared (FIGS. 3 and 4). The diversity of the microbiome decreased from Day −7 to Day −4 in both groups. As the animals were in the process of acclimating and were not yet treated at Day −4, these data suggest that the microbiome was changing based on the new environment. Animals began amoxicillin treatment on Day 1 and by Day 4, the microbiome in the Amoxicillin+SYN-004 group had stabilized to a median similarity comparable to that of Day −4. Notably, the microbiome of the Amoxicillin-alone treated pigs continued to lose diversity throughout the duration of the study. These data demonstrate that SYN-004 prevented the loss of diversity in the microbiome caused by amoxicillin treatment.

FIG. 3 shows strain relative abundance percent similarity. The median percent similarity based on the relative abundance of the bacterial strains identified from sequence analysis of the fecal DNA samples was compared for the amoxicillin alone group (n=5) and the amoxicillin+SYN-004 group (n=5) from Day −7 to Day 9. Amoxicillin alone is displayed as the solid line, and Amoxicillin+SYN-004 is displayed as the dashed line.

FIG. 4 shows strain relative abundance percent similarity boxplot. The median percent similarity based on the relative abundance of the bacterial strains identified from sequence analysis of the fecal DNA samples was compared for the amoxicillin alone group (n=5) and the amoxicillin+SYN-004 group (n=5) from Day −7 to Day 9. Amoxicillin alone is displayed as the gray box, and Amoxicillin+SYN-004 is displayed as the white box. The boxplot displays the median (line), the quartiles (box) and the range (vertical lines).

Heatmaps of the bacterial taxa were constructed based on the relative abundance of each bacterial strain and organized chronologically by study day and by treatment group (FIG. 5).

The abundance of some bacterial species decreased in the amoxicillin alone groups by Day 4 while these groups were maintained in the amoxicillin+SYN-004 group. Similarly, some bacterial species increased in abundance in the amoxicillin alone group while the same bacteria did not overgrow when SYN-004 was present with amoxicillin. These data demonstrate that SYN-004 protected the microbiome from the effects of amoxicillin.

FIG. 5 shows strain abundance heat map. Heatmaps of the bacterial taxa were constructed based on the relative abundance of each bacterial strain and organized chronologically by study day and by treatment group. The groups are labeled on the left side of the figure, Amoxicillin (Amox) and Amoxicillin+SYN-004 (Amox+SYN-004), and the timepoints are indicated by the different colored bars on the left side of the figure according to the Collection Day key. The individual bacterial strains are displayed on the bottom, and the bacterial growth class of each strain is indicated on the top according to the Growth Class key. The individual animals are indicted on the right side of the figure. The white boxes on the right side of the figure indicate bacterial strains that were decreased in the Amoxicillin alone group but retained in the Amoxicillin+SYN-004 group. The green boxes on the left side of the figure indicate bacterial strains that became more abundant in the Amoxicillin alone group but that did not overgrow in the Amoxicillin+SYN-004 group.

A statistical analysis was performed to determine the probability that the microbiomes before and after antibiotic treatment remained the same or were different. The microbiome sequence data were analyzed using a parameterization of the Dirichlet-Multinomial distribution (La Rosa et al., 2012) to perform a Likelihood Ratio Test. The pretreatment Day −4 and the post-treatment Day −9 microbiomes of the Amoxicillin alone and Amoxicillin+SYN-004 treatment groups were compared. The p value obtained comparing the Amoxicillin alone group before and after amoxicillin treatment was p=0.0000000010521, indicating that the two groups were significantly different. In contrast, the p value obtained comparing the Amoxicillin+SYN-004 group was 0.9970586680662, indicating that these two groups were not significantly different. These data demonstrate that SYN-004 protected the microbiome from amoxicillin-mediated damage.

Example 2. SYN-004 Multi-Particulates, Additional SYN-004 Formulations and their In Vitro Characterization Three additional modified-release formulations of SYN-004 were generated and tested. The starting material for the formulations was SYN-004-coated sucrose pellets that lacked the outer, enteric-coating. P3A layered pellets were produced by spray application of P3A drug substance using hydroxypropylcellulose (HPC) or hydroxypropylmethyl cellulose (HPMC) as a binder excipient, water as a solvent, and sucrose spheres as starting material. The spray application was performed using a fluid bed system over six work shifts, in order to achieve a final active pharmaceutical agent (API) percentage of at least 15%. After the sixth work shift of spray application of the P3A/HPC mixture, the P3A layered pellets were dried overnight at room temperature on trays, then sifted through a 1.4 mm sieve prior to bulk packaging in polyethylene (PE) bags and PE containers. The drug-layered pellets were stored at 5±3° C. for further processing. For example, in some embodiments, the P3A layered pellets were coated with different coatings to achieve specific enzyme release profiles.

The three new formulations utilized different coatings to obtain modified enzyme release profiles (FIG. 6). The different coatings included an enteric coating that released at pHs of >6.2 or an enteric coating that released at pHs of >6.7. The third type of coating was an osmotic-rupture coating that released the enzyme within a specified timeframe, between 2-4 hours after ingestion. The three formulations were characterized in vitro for physical appearance, composition, and enzyme dissolution profiles. The three formulations with the most promising profiles were selected for evaluation with oral amoxicillin in a pig model.

Enteric-Coating SYN-004 Formulation with Release at pHs>6.2

The SYN-004-coated sucrose pellet starting material was coated with a mixture of Eudragit L100, Eudragit S100, and triethyl citrate at a ratio of 72.7/18.2/9.1. The parameters of the spray coating (FIG. 6) was using a Niro-Aeromatic Lab Fluid Bed Dryer, Model MP-1 with a bowl size of 3.5 inches, air distribution with a Mod B Plate, a Schlick 970 (tall) nozzle with a 1.2 mm liquid tip size, and a column gap of 10 mm. The Eudragit L100, Eudragit S100, and triethyl citrate at a ratio of 72.7/18.2/9.1 was dissolved in isopropanol and water at a 95/5 ratio. First the isopropanol and water were mixed and then the Eudragits were added, after which the triethyl citrate was added. The mixture was stirred until dissolved for at least 30 minutes following the addition of the triethyl citrate. The operating parameters of the fluid bed dryer were a gas flow rate of 35 CFM, inlet temperature of 28° C., inlet dew point of 8.6° C., atomizer pressure of 2.7 bar, a spray rate of 2.3 g/min, and a bed temperature of 25° C. The fluid bed process performance was a total solution sprayed of 612 g, a run time of 4 hrs and 25 minutes, a bed dump of 105.1 g, a final coat weight estimate of 35% and a coating efficiency of 97.2%. Samples were dried at 40° C. for 2 hours. Samples were collected at intermediate coating weights of 25% and 30% for characterization along with the coat weight of 35%.

The coated particles were characterized based on coat thickness vs coat weight and mass fraction (weight %) vs particle size (FIG. 7, panels A and B). The collected particles were confirmed to have estimated coat weights of 25% with an average coat thickness of approximately 70 um, 30% with an average 80 um coat thickness, and 35% with an average 100 um coat thickness. The final product particles (35% coating efficiency) were characterized based on the mass fraction vs particle size and it was found that the midpoint of the particle sizes ($D_{50}$) was 1390 um. The coated particles were also characterized by scanning electron microscopy (FIGS. 8 and 9). The particles appeared smooth and uniformly coated with sized of approximately 1.4 mm. Cross sections of the particles (n=6 for each coating %) allowed calculation of the coating thicknesses. The calculated coating thicknesses were 69.7 um for the 25%, 77.9 um for the 30% and 99.7 um for the 35%, similar to what was observed in the coat thickness vs coat weight evaluation (FIG. 7). Additional scanning electron microscopy characterization of the 35% particles displayed a uniform surface and a 50× magnified view of a cross sectioned particle clearly displayed the sucrose core, the SYN-004 layer over the core, and the outer Eudragit coating (FIG. 9). Based on these data, the 35% pH>6.2 particles were chosen as the prototype for further testing.

Enteric-Coating SYN-004 Formulation with Release at pHs>6.7

The SYN-004-coated sucrose pellet starting material was coated with a mixture of Eudragit L100, Eudragit S100, and triethyl citrate at a ratio of 30/60.9/9.1. The parameters of the spray coating (FIG. 6) was using a Niro-Aeromatic Lab Fluid Bed Dryer, Model MP-1 with a bowl size of 3.5 inches, air distribution with a Mod B Plate, a Schlick 970 (tall) nozzle with a 1.2 mm liquid tip size, and a column gap of 10 mm. The Eudragit L100, Eudragit S100, and triethyl citrate at a ratio of 72.7/18.2/9.1 was dissolved in isopropanol and water at a 95/5 ratio. First the isopropanol and water were mixed and then the Eudragits were added, after which the triethyl citrate was added. The mixture was stirred until dissolved for at least 30 minutes following the addition of the triethyl citrate. The operating parameters of the fluid bed dryer were a gas flow rate of 35 CFM, inlet temperature of 29° C., inlet dew point of 7.5° C., atomizer pressure of 2.5 bar, a spray rate of 2.4 g/min, and a bed temperature of 25° C. The fluid bed process performance was a total solution sprayed of 628.7 g, a run time of 4 hrs and 24 minutes, a bed dump of 105.1 g, a final coat weight estimate of 35% and a coating efficiency of 99.6%. Samples were dried at 35° C. for 2 hours. Samples were collected at intermediate coating weights of 25% and 30% for characterization along with the 35%.

The coated particles were characterized based on coat thickness vs coat weight and mass fraction (weight %) vs particle size (FIG. 10, panels A and B). Coating was more efficient than expected and the estimated coat weights were 30% (referred to as the expected 25%), 35% (referred to as the expected 30%), and 40% (referred to as the expected 35%), with coat thicknesses of approximately 65 um, 85 um, and 110 um, respectively. The final product particles (40% coating efficiency) were characterized based on the mass fraction vs particle size and it was found that the midpoint of the particle sizes ($D_{50}$) was 1388 um. The coated particles were also characterized by scanning electron microscopy (FIGS. 11 and 12). The particles appeared smooth and uniformly coated with sizes of approximately 1.5 mm. Cross sections of the particles (n=6 or n=10 for each coating %) allowed calculation of the coating thicknesses. The calculated coating thicknesses were 68.5 um for the 25%, 85.2 um for the 30% and 113 um for the 35%, similar to what was observed in the coat thickness vs coat weight evaluation (FIG. 10). Additional scanning electron microscopy characterization of the 35% particles displayed a uniform surface and a 50× magnified view of a cross sectioned particle clearly displayed the sucrose core, the SYN-004 layer over the core, and the outer Eudragit coating (FIG. 12).

Based on these data, the 35% pH>6.7 particles were chosen as the prototype for further testing.

Osmotic-Rupture Coating SYN-004 Formulation with Timed Release

The SYN-004-coated sucrose pellet starting material was coated with a mixture of 71.4% pulverized croscarmellos sodium (AcDiSol, FMC Biopolymer), 28.6% hydroxyproplycellulose (HPC) in 100 proof ethyl alcohol. This layer was referred to as the sweller layer. The HPC was added to 2/3 of the ethyl alcohol and the AcDiSol was added to 1/3 of the ethyl alcohol. The solution was high shear mixed for 3 minutes at 4000 rpm. The parameters of the spray coating (FIG. 6) was using a Niro-Aeromatic Lab Fluid Bed Dryer, Model MP-1 with a bowl size of 3.5 inches, air distribution with a Mod B Plate, a Schlick 970 (tall) nozzle with a 1.2 mm liquid tip size, and a column gap of 10 mm. The operating parameters of the fluid bed dryer were a gas flow rate of 35 CFM, inlet temperature of 32° C., inlet dew point of 6.1° C., atomizer pressure of 2.5 bar, a spray rate of 3.4 g/min, and a bed temperature of 28° C. The fluid bed process performance was a total solution sprayed of 385 g, a run time of 1 hr and 53 minutes, a bed dump of 119.1 g, a final coat weight estimate of 37% and a coating efficiency of 82%. No intermediate samples were collected.

The next step was to add the osmotic rupture coating to the SYN-004 particles coated with the sweller layer. The osmotic rupture coating composition was 75% Aquacoat ECD (ethylcellulose dispersion, FMC Biopolymer), and 25% triethyl citrate (TEC) in water. The TEC was added to the Aquacoat ECD and the residual TEC was washed with water and added to solution. The suspension was stirred throughout the run. The parameters of the spray coating (FIG. 6) was using a Niro-Aeromatic Lab Fluid Bed Dryer, Model MP-1 with a bowl size of 3.5 inches, air distribution with a Mod B Plate, a Schlick 970 (tall) nozzle with a 1.2 mm liquid tip size, and a column gap of 10 mm. The operating parameters of the fluid bed dryer were a gas flow rate of 35 CFM, inlet temperature of 51° C., inlet dew point of 8.3° C., atomizer pressure of 2.5 bar, a spray rate of 2.0 g/min, and a bed temperature of 35° C. The fluid bed process performance was a total solution sprayed of 146 g, a run time of 1 hr and 11 minutes, a bed dump of 124, a final coat weight estimate of 13.5% and a coating efficiency of 66%. Intermediate samples were collected at 7.3%, 9.1%, 10%, and 11.5%.

Following coating, the particles were cured. Multiple curing temperatures and times were evaluated for osmotic rupture (burst time) and beta-lactamase enzyme activity. The initial analyses compared particles with 10% or 11.5% osmotic coat weights with cure temperatures of 50° C. or 60° C., and cure times of 2, 5, and 8 hours (FIG. 13). Pellets were added to a 50 mM $KH_2PO_4$ pH 6.2 buffer at room temperature without stirring, images of the pellets were taken every 5 minutes to evaluate particle disruption as visual disruption of the coating, significant deformation of the particles and the presence of external AcDiSol. The data demonstrated that the 10% and 11.5% coat weights were not of sufficient thickness to reach the desired 4 hours particle burst delay, as the particles started to appear broken between 2 and 3 hours. In addition, the cure time and temperature of 60° C. for 2 hours appeared optimal. Based on these data, the 10% SYN-004 pellets were recoated to 11.4% and 13.5% with a cure temperature of 60° C. for 2 hours and retested as described (FIG. 14). Pellets with the 13.5% coating remained intact for over 5 hours with 50% rupture occurring at 8 hours, while the 10% and 11.4% began to break at 2.5 or 3 hours with 50% rupture occurring at 4 hours. The appearance of the 10% and 13.5% particles after soaking for 0 to 8.5 hours is displayed in FIG. 15.

The coated particles were characterized based on coat thickness vs coat weight and mass fraction (weight %) vs particle size (FIG. 16). Coating was as expected with coat weights ranging from 7% to 13%, and thicknesses of 20 um to 50 um. The final product particles (13.5% coating weight) were characterized based on the mass fraction vs particle size and it was found that the midpoint of the particle sizes ($D_{50}$) was 1432 um. The coated particles were also characterized by scanning electron microscopy (FIGS. 17 and 18). The particles appeared smooth and uniformly coated with sizes of approximately 1.5 mm. Cross sections of the particles (n=10 for each coating %) allowed calculation of the coating thicknesses. The calculated coating thicknesses were 30.8 um for the 10% coat weight, 41.3 um for the 11.5% coat weight, and 48 um for the 13.5% coat weight. Additional scanning electron microscopy characterization of the 13.5% coat weight particles displayed a uniform surface and a 50× magnified view of a cross sectioned particle displayed the sucrose core, the SYN-004, and coating layers (FIG. 18).

To verify that the conditions chosen to cure the osmotic coating did not affect SYN-004 biological activity, an additional study was performed. Osmotic rupture, 13.5% coat weight SYN-004 pellets, under different curing conditions were evaluated for retention of biological activity (FIG. 19). Osmotic rupture pellets were added to a pH 6.8 potassium phosphate buffer and stirred overnight to ensure removal of the entire coating. Aliquots of the buffer were analyzed for SYN-004 biological activity using the CENTA chromogenic microtiter plate assay. The data demonstrate that cure times ranging from 8 hours at 50° C. or 2 hours at 60° C. did not affect SYN-004 biological activity. The SYN-004 starting material, the uncoated pellets, displayed 84.0%±15.2% activity, the uncured particles, 94.5+12.2% activity, 50° C.

for 2 hrs, 84.0+6.2% activity, 50° C. for 5 hr, 75.8+6.4%, 50° C. for 8 hr, 83.9+1.9% activity, and 60° C. for 2 hrs, 86.1+1.4% activity.

Based on these data, the 13.5%, cured at 60° C. for 2 hours, osmotic rupture particles were chosen as the prototype for further testing.

The criteria for identifying a promising modified-release formulation of SYN-004 for oral use with oral antibiotics was to identify SYN-004 formulation or formulations that have the desired enzyme release profile to maximize antibiotic bioavailability while minimizing the antibiotic's effect on the intestinal microflora (FIG. 20). The three SYN-004 formulations generated as described in Example 2 were further characterized. The three formulations chosen were: 1) enteric-coated pH 6.2 release, 2) enteric-coated pH 6.7 release, and 3) an osmotic rupture formulation. The characteristics of these formulations are displayed in TABLE 3.

TABLE 3

| Formulation Prototypes | Release pH | Coating %/thickness | Release characteristics | | | | | Biological activity Compared to SYN-004 |
|---|---|---|---|---|---|---|---|---|
| | | | 2 hr | 4 hr | Lag Time | Duration (hr) | Total (hr) | |
| SYN-004 (Control) | 5.5 | ~55 um | 0-1% | 20-50% | NA | 1.3 | 2.25 | 100% |
| Enteric 6.2 | 6.2 | 35%/100 um | 0-10% | 5-15% | NA | 2.0 | 4 + 2 | 135% |
| Enteric 6.7 | 6.7 | 35%/113 um | 0-1% | 0-5% | NA | 8-10 | 4 + 8-10 | 120% |
| Osmotic | NA | 13.5%/48 um | 0-5% | 5-50% | 3 hr | 3 | 6 | 105% |

The three formulations were evaluated in vitro to characterize their dissolution profiles and to verify that the SYN-004 enzyme retained biological activity in each formulation (FIGS. 21 and 22). For each formulation, a total of 7.5 mg of SYN-004 active agent was incubated in 25 ml of a pH 2.0 solution (0.01N HCl) for 2 hours to mimic the conditions of the stomach following ingestion. The pH was then increased to 5.5 (total volume 75 ml in potassium phosphate) for an additional 2 hours. The pH was then adjusted to 6.5 using 10N KOH. All incubations were performed at 37.5° C. with agitation of 250 rpm. For each sample, 20 ul was collected into a 2 ml volumetric post auto sampler at the indicated time points. Samples were evaluated for protein concentration using absorbance at 280 nm and for SYN-004 biological activity using the CENTA chromogenic assay. The Enteric pH 6.2 formulation showed minimal release in acidic environments with a duration of release of approximately 2 hours. The Enteric pH 6.7 formulation showed minimal release in acidic environments followed by a duration of release of approximately 8-10 hours. The Osmotic Rupture formulation providing pH-independent release, displayed a 3 hour lag followed by a duration of release of 3 hours. The original SYN-004 formulation (Enteric, pH 5.5) showed minimal release in acidic environments followed by a duration of release of 1.3 hours. The data demonstrate that all formulations maintain SYN-004 biological activity for the duration of the three-stage dissolution test for 24 hours. The formulations have the desired release characteristics for testing in an animal model with an oral antibiotics such as amoxicillin.

Example 3: Preparation of Capsules Filled with SYN-004 Formulations for In Vivo Evaluations The three SYN-004 formulation pellets, as described in Example 2, and the original SYN-004 formulation pellets (Enteric 5.5) as describedd in Example 1, were used to fill size 0 gelatin capsules to achieve a dose of 50 mg of SYN-004 active agent (TABLE 4). The list of components and the amounts in these capsules are provided in TABLE 5 below. A volumetric fill was used with a 100% weight sort and a +3% target rejection limit. There was less than a 3% RDS fill variation. The average mass of the empty gelatin capsules was 93 mg.

TABLE 4

| Formulation Prototypes | Capsule Color | Target Fill Weight (mg) | Average Fill Weight (mg) | % Target | % RSD | % Capsules Rejected (±3% Limits) |
|---|---|---|---|---|---|---|
| SYN-004 (Control) | Clear | 298 | 297 | 99.9% | 1.0% | 0.0% |
| Enteric 6.2 | Green | 360 | 359 | 99.9% | 1.4% | 0.9% |
| Enteric 6.7 | White | 401 | 402 | 100.2% | 1.2% | 2.3% |
| Osmotic | Orange | 447 | 447 | 100% | 1.1% | 3.2% |

TABLE 5

Composition of osmotic rupture, enteric pH 6.2, and enteric pH 6.7 SYN-004 50 mg active capsules

| Component | Osmotic Rupture mg | % Total | Enteric pH 6.2 mg | % Total | Enteric pH 6.7 mg | % Total |
|---|---|---|---|---|---|---|
| Sucrose sphere | 73.7 | 16.5 | 73.7 | 20.5 | 73.7 | 18.4 |
| Hydroxypropylcellulose | 140.0 | 31.3 | 110.5 | 30.7 | 110.5 | 27.5 |
| SYN-004 | 50.0 | 11.2 | 50.0 | 13.9 | 50.0 | 12.5 |
| EUDRAGIT ® L100 | — | — | 87.5 | 24.3 | 49.1 | 12.2 |
| EUDRAGIT ® S100 | — | — | 21.9 | 6.1 | 98.2 | 24.5 |
| AcDiSol | 110.0 | 24.8 | — | — | — | — |
| Aquacoat ECD | 29.3 | 6.6 | — | — | — | — |
| Buffer salts | 5.0 | 1.1 | 5.0 | 1.4 | 5.0 | 1.3 |
| Talc | 38.2 | 8.6 | — | — | — | — |
| Triethyl citrate | — | — | 10.9 | 3.0 | 14.7 | 3.7 |
| Subtotal | 446 | 100.0 | 360 | 100.0 | 401 | 100.0 |
| Hard gelatin capsule #0 | 93.0 | | 93.0 | | 93.0 | |
| Total | 539 | | 445 | | 494 | |

The dissolution of the SYN-004 pellets from the capsules was evaluated and compared to the data obtained from dissolution of the SYN-004 pellets prior to encapsulation (FIG. 23). The dissolution study was performed as described previously, however, instead of using 7.5 mg of pellets, one capsule containing 50 mg of active SYN-004 was used. Briefly, one capsule of each formulation, except SYN-004 original (Enteric pH 5.5) was incubated in a pH 2.0 solution (0.01N HCl) for 2 hours to mimic the conditions of the stomach following ingestion. The pH was then increased to 5.5 for an additional 2 hours. The pH was then adjusted to 6.5 using 10N KOH. All incubations were performed at 37.5° C. with agitation of 250 rpm. For each sample, 20 ul was collected into a 2 ml volumetric post auto sampler at the indicated time points. Samples were evaluated for protein concentration using absorbance at 280 nm. The data demonstrate that no damage to the pellets occurred during capsule filling. A slower than expected release rate was observed for the Enteric pH 6.2 and the Enteric pH 6.7 formulations.

Following encapsulation, the formulations retained the desired release characteristics for testing in an animal model with an oral antibiotics such as amoxicillin.

Example 4. Evaluation of the Modified-Release Formulations of SYN-004 in Normal Piglets A study was performed using normal piglets to compare the three, modified-release formulations of SYN-004 as described in Example 2, and the original SYN-004 formulation (Enteric pH 5.5) as described in Example 1, delivered orally with oral amoxicillin, to evaluate the effect on amoxicillin serum levels and protection of the microbiome from amoxicillin-induced dysbiosis (FIG. 24).

A total of 25, two month old Yorkshire piglets, approximately 20 kg each, were used for this study. All 25 animals were treated with oral amoxicillin twice a day for a total of 7 days, in addition, Groups 2-5 received SYN-004 four times a data starting the day before amoxicillin treatment for a total of 9 days (TABLE 6).

On Study Day 0, Groups 2-5 (Pigs 6-25) received one size 0 capsule of one of each of the four SYN-004 formulations, containing 50 mg of SYN-004, orally, four times a day at 7 am, 12 μm, 5 μm, and 10 μm for a total of 9 days. Pigs were fed 3 times a day, after SYN-004 dosing at 7 am, after SYN-004 dosing at 12 μm, and after SYN-004 dosing at 5 μm. Beginning on Study Day 1, all groups Groups 1-5 (Pigs 1-25) received oral amoxicillin (fruit flavored oral suspension, Sandoz, NDC: 0781-6157-46, Lot #FB0703; 20 mg/kg) twice a day at 7 am and at 5 μm, for a total of 7 days. Animals received the amoxicillin first, followed by the SYN-004, then feeding.

On Day 3, after 5 amoxicillin doses, animals were bled and serum collected. Blood was collected aseptically from the vena cava from anesthetized animals. Three blood draws were performed, at 1 hr, 3 hrs, and 6 hrs after amoxicillin administration. A Telazol cocktail was administered intramuscularly at a minimal dose (1 mL or less per 50 lbs) to achieve light anesthesia/sedations. At each timepoint, approximately 9 mL of blood was collected into a serum separator vacutainer tube. After coagulation, samples were centrifuged and the serum was transferred to a cryovial and stored at −80° C. until shipment to the evaluation laboratory (Center for Anti-Infective Research and Development, Hartford Hospital, Hartford, Conn.).

Amoxicillin levels in the pig serum are quantified using a modification of a validated HPLC-based assay (Du et al., 2005). A standard curve is prepared in negative control pig serum and had 6 points ranging from 1 to 30 ug/mL of amoxicillin. Sigma Plot is used to calculate drug concentrations and a −1 weighting factor is used. The limit of detection of the assay is 1.5 ug/mL.

DNA is isolated from the fecal samples and subjected to whole genome shotgun sequencing using an Illumine HiSeq

TABLE 6

Piglet Study Design

| Group (N = 5) | SYN-004 | SYN-004 Delivery | Antibiotic Delivery |
| --- | --- | --- | --- |
| 1 | None | None | Amoxicillin suspension |
| 2 | SYN-004 (original formulation) Clear capsules | 1 capsule (50 mg active) QID 7 am, 12 pm, 5 pm and 10 pm | (40 mg/kg/day) Oral, each dose 20 mg/kg BID 7 am, 5 pm |
| 3 | SYN-004 Formulation #2 Green capsules | | |
| 4 | SYN-004 Formulation #3 Orange capsules | | |
| 5 | SYN-004 Formulation #4 White capsules | | |

Three pre-treatment fecal samples were obtained, at Day −4, Day −2, and Day 0 (prior to SYN-004 treatment. The fecal samples were collected using the OMNIgene GUT sample collection kits (OMR-200, DNA Genotek, Ontario, Canada) and stored at room temperature away from light until all samples were collected. DNA isolated from the fecal samples was subjected to deep sequencing of the intestinal microbiome and analyses. Additional fecal samples were collected at Day −2, and Day 4. These samples were collected into 50 ml conical tubes and quickly frozen and stored at −80° C. These samples were submitted for amoxicillin quantification.

system with a target of 20 million 100 bp single reads per sample. DNA isolation and sequencing are performed by Hudson Alpha Genomic Services Laboratory (Huntsville, Ala.). Sequenced datasets are taxonomically classified using the GENIUS® software package (Hasan et al., 2014, Lax et al., 2014) by CosmosID, Inc. (Rockville, Md.).

The resulting data are expected to demonstrate that each formulation of SYN-004 does not prevent the absorption of amoxicillin from the GI tract, suggesting that the amoxicillin was absorbed before SYN-004 was released into the GI tract. In addition, the resulting data are expected to demonstrate that each formulation of SYN-004 protected the microbiome from the damage caused by amoxicillin treatment.

Example 5. Formulations

The beta-lactamase is formulated for release in a location in the GI tract in which it deactivates residual oral antibiotic residue, specifically for release in a location in the GI tract that is distal to the release of the orally administered antibiotic.

P3A is formulated by combining P3A with a latex, or other polymer, and a particulate, micro-encapsulated enzyme preparation is formed. The microspheres may then be covered with a pH-dependent enteric coating. No sucrose core is required and this allows for higher drug loading per pellet and therefore a smaller capsule size for therapy. Formulations are developed to produce particles that have enteric functionality (not released in the stomach, complete release in the distal small intestine) built into the matrix itself, to reduce excipient load. If the formulation shows good retention of activity and stability, but insufficient protection from acidic conditions, enteric coating is applied to the particulates.

A variety of approaches for generating particulates (such as microspheres, aggregates, other) that are amenable to the inclusion of proteins may be used. These approaches involve at least two phases, one containing the protein, and one containing a polymer that forms the backbone of the particulate. For example, coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form the microspheres may be used.

In another approach, the protein and stabilizing excipients (e.g., hydroxyproplyl methylcellulose acetate succinate (HPMCAS) type MF; Aquacoat (FMC), sodium stearyl fumarate; trehalose, mannitol, Tween 80, polyvinyl alcohol, and/or others) are combined and then the mixture from aqueous solution is sprayed, particles form and are collected. The particles are then suspended in a dry, water immiscible organic solvent containing polymer and release modifying compounds, and the suspension sonicated to disperse the particles. Using this method, two formulations of P3A were developed (TABLES 7 and 8). Notably, HPMCAS-MF was used as the pore forming reagent as it is water insoluble at low pH (i.e., forms a gel), and become water soluble at high pH. At least 80% P3A activity was recovered after dissolution of the P3A particles made using these formulations as measured by the CENTA chromogenic assay (TABLES 7 and 8) (Bebrone et al., 2001; Antimicrobial Agents and Chemotherapy; 45:1868).

TABLE 7

P3A formulation 1

| Component | Item | Amt (g) in 500 ml | % Total | % |
|---|---|---|---|---|
| API | P3A | 2.50 | 0.5 | 9.77 |
| Pore Former | HPMCAS-MF | 1.67 | 0.3 | 6.53 |
| Matrix | Aquacoat (FMC) | 50.00 | 10.1 | 58.62 |
| Lube | Sodium-Stearyl Fumarate | 0.83 | 0.2 | 3.24 |
| Buffer | Sodium Hydrogen Phosphate | 0.59 | 0.1 | 2.31 |
| Protectant | Trehalose | 5.00 | 1.0 | 19.54 |
| Water | | 440.00 | 88.8 | |
| Total Water | | 489.85 | | |
| Total Solids | | 25.59 | | 100.00 |
| Solids in Matrix | | | | 30.00 |
| Activity Recovered | | | | 82.00 |

TABLE 8

P3A formulation 2

| Component | Item | Amt (g) in 500 ml | % Total | % |
|---|---|---|---|---|
| API | P3A | 11.25 | 2.30 | 39.37 |
| Pore Former | HPMCAS-MF | 1.50 | 0.30 | 5.25 |
| Matrix | Aquacoat (FMC) | 50.00 | 10.00 | 52.49 |
| Lube | Sodium-Stearyl Fumarate | 0.33 | 0.10 | 1.14 |
| Buffer | Sodium Hydrogen Phosphate | 0.50 | 0.10 | 1.75 |
| Protectant | Trehalose | 0.00 | 0.00 | 0.00 |
| Water | | 437.50 | 87.50 | |
| Total Water | | 472.50 | | |
| Total Solids | | 28.58 | | 100.00 |
| Solids in Matrix | | | | 30.00 |
| Activity Recovered | | | | 80.00 |

Another approach uses aqueous phases but no organic solvent. Here, the enzyme, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. If the release modifiers are insoluble at acidic conditions but soluble at higher pHs (such as carboxylic acidic) then release from the matrix should be inhibited in the gastric environment.

Formulation approaches are shown in FIGS. 25-28.

Example 6. GI Tract Localization of Beta-Lactamase Release

These studies are designed to identify preferred sites of beta-lactamase delivery to the GI tract to achieve efficient antibiotic absorption and microbiome protection.

Beta-lactamase SYN-004 a/k/a P3A (resuspended in PBS or other buffer, or any of the formulations of SYN-004) is delivered directly to various regions of the intestinal tract of dogs via intubation or a fistula in the intestine. Animals receive oral antibiotic, such as amoxicillin, or amoxicillin/clavulanic acid (Augmentin), and P3A via direct delivery to the small intestine including the duodenum, jejunum, ileum, and/or cecum. Plasma levels of the antibiotic are measured and the diversity of the microbiome is assessed by 16S sequence analysis of microbes in the stool, as an assessment of antibiotic degradation, and microbiome protection. Cohorts include antibiotic alone, antibiotic/inhibitor alone, antibiotic/inhibitor+P3A, and antibiotic+P3A, delivered to the indicated areas of the small intestine.

To perform this study, fistulas are implanted in groups of dogs (n=3-5 per cohort) at the indicated locations in the small intestine including, the duodenum, jejunum, ileum, cecum, and ascending colon (Table 1). The dogs receive a dosage of oral antibiotic, such as amoxicillin or an antibiotic/inhibitor combination, such as amoxicillin/clavulanic acid (Augmentin) as a single dose. P3A is delivered as an oral pill (using the current SYN-004 formulation) or dissolved in PBS buffer via direct infusion into the fistula and delivered within 30 minutes after the oral antibiotic. Plasma samples are drawn from the dogs at various time points to measure antibiotic levels in the blood as a measure of antibiotic absorption. Fecal samples are collected from the animals to measure the level of excreted antibiotics and to assess the intestinal microbiome using 16S sequence analyses, as an additional assessment of antibiotic degradation.

The results allow the demonstration that delivery of P3A to the small intestine results in protection of the microbiome and does not affect antibiotic plasma levels. The study allows the identification of preferred sites of beta-lactamase delivery to the small intestine or colon to achieve microbiome protection. Related studies with different antibiotics and/or antibiotic/inhibitor combinations may be undertaken to specify key locations in the intestinal tract.

Example 7. Evaluation of SYN-004 Delivered with Augmentin or Sultamicilllin to Pigs This study evaluates use of an enteric-coated pellet formulation of SYN-004, e.g. those described elsewhere herein, delivered with oral amoxicillin/clavulanate (Augmentin; antibiotic/inhibitor combination) or amoxicillin alone for protection of the microbiome without affecting antibiotic absorption.

SYN-004 enteric-coated pellet formulation, and oral amoxicillin/clavulanate (Augmentin) or oral amoxicillin alone, cohorts (n=3-5) of normal young pigs (~50 lbs) are treated with clindamycin as a positive control for microbiome damage (one time), or oral Augmentin+/−SYN-004 for 5-7 consecutive days or oral amoxicillin+/−SYN-004 for 5-7 consecutive days (TABLE 10). SYN-004 treatment is started 1 day prior to oral antibiotic delivery. Plasma and stool is collected daily, beginning the day prior to treatment (Day −1). Plasma is monitored for amoxicillin levels and stool is subjected to 16S RNA sequencing to monitor the diversity of the microbiome and stool is analyzed for the presence of amoxicillin.

This study may display that at one or both of the Augmentin/SYN-004 doses or the amoxicillin/SYN-004 doses, the plasma levels of amoxicillin are not affected while the microbiome is protected, indicating that the SYN-004 degraded the amoxicillin excreted into the intestine following amoxicillin absorption without affecting the initial amoxicillin absorption. Other orally-delivered antibiotics and/or antibiotic-inhibitor combinations are evaluated in an analogous manner.

TABLE 9

Treatment of fistulated dogs with oral antibiotic/
inhibitor or oral antibiotic and SYN-004

| Cohort | Oral Antibiotic | P3A |
|---|---|---|
| 1 | None | None |
| 2 | Antibiotic | None |
| 3 | Antibiotic/inhibitor | None |
| 4 | None | P3A-current oral formulation |
| 5 | Antibiotic and/or antibiotic/inhibitor combo | P3A-current oral formulation |
| 6 | Antibiotic and/or antibiotic/inhibitor combo | P3A-via fistula to duodenum |
| 7 | Antibiotic and/or antibiotic/inhibitor combo | P3A-via fistula to jejunum |
| 8 | Antibiotic and/or antibiotic/inhibitor combo | P3A-via fistula to ileum |
| 9 | Antibiotic and/or antibiotic/inhibitor combo | P3A-via fistula to cecum |
| 10 | Antibiotic and/or antibiotic/inhibitor combo | P3A-via fistula to ascending colon |

TABLE 10

Treatment of normal pigs with oral antibiotic
(Augmentin or amoxicillin) and oral SYN-004

| Cohort (n = 3-5) | Antibiotic | Oral SYN-004 |
|---|---|---|
| 1 | none | none |
| 2 | Clindamycin (30 mg/kg) | none |
| 3 | Oral Augmentin or amoxicillin (875 mg/kg BID) | SYN-004 High dose (12.5 mg/kg QID) |
| 4 | Oral Augmentin or amoxicillin (875 mg/kg BID) | SYN-004 Low dose (0.5 mg/kg QID) |
| 5 | Oral Augmentin or amoxicillin (875 mg/kg BID) | none |
| 6 | Oral Augmentin or amoxicillin (500 mg/kg BID) | SYN-004 High dose (12.5 mg/kg QID) |

TABLE 10-continued

Treatment of normal pigs with oral antibiotic
(Augmentin or amoxicillin) and oral SYN-004

| Cohort (n = 3-5) | Antibiotic | Oral SYN-004 |
|---|---|---|
| 7 | Oral Augmentin or amoxicillin (500 mg/kg BID) | SYN-004 Low dose (0.5 mg/kg QID) |
| 8 | Oral Augmentin or amoxicillin (500 mg/kg BID) | none |

Evaluation of an enteric-coated pellet formulation of SYN-004's efficacy in the degradation of a covalently bound oral antibiotic/inhibitor combination (sultamicillin) without affecting antibiotic absorption is undertaken. It is not clear if the ampicillin and/or sulbactam components of sultamicillin are functional prior to metabolism (breaking of the ester bond linking the ampicillin and sulbactam). If the ampicillin is inactive in sultamicillin, this would function as an additional fail-safe where SYN-004 would not degrade sultamicillin prior to absorption, but is predicted to efficiently degrade ampicillin when excreted back into the intestine to protect the microbiome.

Using the SYN-004 enteric-coated pellet formulation described herein, oral sultamicillin (ampicillin/sulbactam 1:1 covalent linkage) or oral ampicillin, cohorts (n=3-5) of normal young pigs (~50 lbs) are treated with clindamycin as a positive control for microbiome damage (one time), or oral sultamicillin or oral ampicillin+/−SYN-004 for 5-7 consecutive days (TABLE 11). SYN-004 treatment is started 1 day prior to oral antibiotic delivery. Plasma and stool is collected daily, beginning the day prior to treatment (Day −1). Plasma is monitored for ampicillin levels and stool is subjected to 16S RNA sequencing to monitor the diversity of the microbiome, and stool is analyzed to measure ampicillin levels. This study may display that at one or both of the oral sultamicillin/SYN-004 doses, and/or the oral ampicillin/SYN-004 dose, the plasma levels of ampicillin are not affected while the microbiome is protected, indicating that the SYN-004 degraded the ampicillin excreted into the intestine following ampicillin absorption without affecting the initial ampicillin absorption.

TABLE 11

Treatment of normal pigs with oral
sultamicillin or ampicillin and SYN-004

| Cohort (n = 3-5) | Antibiotic | Oral SYN-004 |
|---|---|---|
| 1 | none | none |
| 2 | Clindamycin (30 mg/kg) | none |
| 3 | Oral Sultamicillin or ampicillin (750 mg/kg BID) | SYN-004 High dose (12.5 mg/kg QID) |
| 4 | Oral Sultamicillin or ampicillin (750 mg/kg BID) | SYN-004 Low dose (0.5 mg/kg QID) |
| 5 | Oral Sultamicillin or ampicillin (750 mg/kg BID) | none |
| 6 | Oral Sultamicillin or ampicillin (375 mg/kg BID) | SYN-004 High dose (12.5 mg/kg QID) |
| 7 | Oral Sultamicillin or ampicillin (375 mg/kg BID) | SYN-004 Low dose (0.5 mg/kg QID) |
| 8 | Oral Sultamicillin or ampicillin (375 mg/kg BID) | none |

Example 8. In Vivo Evaluation of Modified-Release Formulations of P3A

The modified-release formulations of P3A, inclusive of those described elsehwhere herein, designed to release at preferred sites in the small intestine as determined by the study outlined in Example 6, is tested in rodents, dogs, and/or pigs to determine if P3A is efficacious in the degradation of an oral antibiotic/inhibitor combination or oral antibiotic alone, without affecting antibiotic absorption.

Results from Example 6 are expected to identify the preferred sites of P3A delivery to the small intestine to achieve efficient oral antibiotic absorption with protection of the microbiome. Using the data from Example 6, formulations of P3A with the chosen release profile are evaluated in rodents, pigs, and/or dogs as described in Examples 5 and 7. Antibiotics chosen for initial evaluation include the antibiotic/inhibitor combinations of Augmentin, sultamicillin, and the antibiotics amoxicillin and/or ampicillin. For pig or dog studies, cohorts (n=3-5) of normal young pigs or beagle dogs are treated with clindamycin (once time) as a positive control for microbiome damage, or oral antibiotic/inhibitor (Augmentin, sultamicillin) or oral antibiotic (amoxicillin or ampicillin) +/−P3A for 5-7 consecutive days (TABLE 12). P3A treatment is started 1 day prior to oral antibiotic delivery. Plasma and stool is collected daily, beginning the day prior to treatment (Day −1). Plasma is monitored for antibiotic levels and stool is subjected to 16S RNA sequencing to monitor the diversity of the microbiome and stool is analyzed for antibiotic levels. This study may display that at one or both of the oral antibiotic/inhibitor/P3A doses, and/or at one or both of the oral antibiotic/P3A doses, the plasma levels of antibiotic are not affected while the microbiome is protected, indicating that the P3A degraded the antibiotic excreted into the intestine following antibiotic absorption without affecting the initial antibiotic absorption.

TABLE 12

Treatment of normal pigs and/or dogs with
modified-release formulations of
P3A and oral antibiotic/inhibitor combinations
(Augmentin, and/or sultamicillin) or oral antibiotic
(amoxicillin and/or ampicillin)

| Cohort (n = 3-5) | Antibiotic | Oral P3A (modified-release formulation) |
|---|---|---|
| 1 | none | none |
| 2 | Clindamycin (30 mg/kg) | none |
| 3 | Oral Antibiotic High Dose (TBD mg/kg BID) | P3A High dose (12.5 mg/kg QID) |
| 4 | Oral Antibiotic High Dose (TBD mg/kg BID) | P3A Low dose (0.5 mg/kg QID) |
| 5 | Oral Antibiotic High Dose (TBD mg/kg BID) | none |
| 6 | Oral Antibiotic Low Dose (TBD mg/kg BID) | P3A High dose (12.5 mg/kg QID) |
| 7 | Oral Antibiotic Low Dose (TBD mg/kg BID) | P3A Low dose (0.5 mg/kg QID) |
| 8 | Oral Antibiotic Low Dose (TBD mg/kg BID) | none |

Example 9. Evaluation of P3A as a Prophylactic to Prevent C. difficile Disease (CDI) Following Oral Antibiotic Treatment in Hamsters These studies evaluate the efficacy of SYN-004 (current enteric formulation or modified-release formulations of P3A, e.g. as described herein) in the prevention of CDI in the hamster disease model.

SYN-004 or modified-release formulations of P3A are tested in rodent models of CDI. Rodent models include the Syrian Golden hamster (*Mesocricetus auratus*) *C. difficile* model (Sambol and Tang, 2001; J. Infect. Disease 183: 1760). The hamster model has been referred to as "the gold standard" small animal model for the evaluation of the efficacy of a variety of prophylactic and therapeutic interventions against CDI. CDI is induced in the hamsters using the following protocol. Male Golden Syrian hamsters, purchased from Harlan (Indianapolis, Ind.) are pretreated 5 days or 24 hours prior to infection with a single subcutaneous injection of clindamycin at 10 or 30 mg/kg to deplete the animal's microbiome and predispose them to *C. difficile* infection. As ampicillin is also a risk for *C. difficile* infection (Freeman and Wilcox, 1999; Microbes Infect. 1:377), oral Augmentin, sultamicillin, ampicillin and/or amoxicillin is used in place of clindamycin to predispose the animals to *C. difficile* infection. Plasma is collected at various times prior to and after antibiotic delivery to measure antibiotic blood levels. On the day of infection, animals are inoculated by oral gavage with $10^6$ *C. difficile* (ATCC 43255) vegetative cells per hamster. The *C. difficile* inoculum is prepared by growing the bacteria in Difco reinforced clostridial medium with 1% Oxyrase for 24 hrs under anaerobic conditions. The optical density at 600 nm is adjusted to 1.5 and then diluted 1:10. The hamsters are given 0.75 ml of this suspension orally via gavage. An aliquot of the inoculum is then serially diluted, plated on *brucella* agar supplemented with hemin and vitamin $K_1$ (Remel, Lenexa, Kans.), and incubated anaerobically for 48 hrs in an airtight container (Pack-Anaero MGC) to determine the infection titer. Animals are observed twice daily during the first 24 hrs post-infection and then every 2 hrs for the following 24 hrs during the acute phase of the disease, followed by twice daily for the remainder of the study. Signs of CDI include signs of mortality and morbidity, presence of diarrhea as indicated by a wet tail, and overall appearance including activity, general response to handling, touch, or ruffled fur. Body weights are monitored every 2 to 3 days.

To evaluate the prophylactic potential of SYN-004 or modified-release formulations of P3A, it is administered orally beginning at the time of oral antibiotic administration, 1 day prior to *C. difficile* infection, and continued for the duration of the studies, up to 28 days. Disease is compared in animals that receive clindamycin (as the positive control) or oral antibiotic/inhibitor combinations or oral antibiotics (Oral Antibiotic). The efficacy of the P3A treatment groups are compared to control animals that receive no treatment, animals that receive the standard of care, vancomycin (20 mg/kg orally daily beginning 24 hrs after infection and continued for 5 days), or animals that receive both vancomycin and P3A. Plasma is monitored for antibiotic levels and stool is subjected to 16S RNA sequencing to monitor the diversity of the microbiome. Efficacy evaluations include mortality and evaluation of *C. difficile* bacteria titers and/or *C. difficile* toxins A and B in cecal contents, at the time of death or at the end of the study following euthanasia. The results may show that treatment with the oral antibiotics and the P3A yeast at one or both doses, did not affect blood levels of the antibiotic and protected the animals from CDI, indicating that the P3A expressed by the yeast degraded the antibiotic excreted into the intestine following antibiotic absorption without affecting the initial antibiotic absorption. See TABLE 13 for the experimental design.

TABLE 13

*C. difficile* efficacy hamster study treatment groups

| Cohort (n = 6-10) | Antibiotic | C. diff inoculation | Treatment |
|---|---|---|---|
| 1 | none | None | none |
| 2 | Clindamycin (30 mg/kg) | + | none |
| 3 | Oral Antibiotic Dose TBD | + | none |
| 4 | Oral Antibiotic Dose TBD | + | vancomycin |
| 5 | Oral Antibiotic Dose TBD | + | SYN-004 or P3A High dose (12.5 mg/kg QID) |
| 6 | Oral Antibiotic Dose TBD | + | SYN-004 or P3A Low dose (0.5 mg/kg QID) |
| 7 | Oral Antibiotic Dose TBD | + | Vancomycin + SYN-004 (or P3A) Low dose (0.5 mg/kg QID) |

Example 10. Evaluation of P3A as a Prophylactic to Prevent C. difficile Disease (CDI) Following Oral Antibiotic Treatment in Pigs These studies evaluate the efficacy of SYN-004 (enteric formulation or modified-release formulations of P3A, e.g. as described herein) in the prevention of CDI in humanized pigs.

SYN-004 or modified-release formulations of P3A are tested in a humanized pig model of CDI. The humanized pig model is a model of the human gastrointestinal tract where the gnotobiotic pigs are reconstituted with human fecal homogenates (Zhang et al., Gut Microbes 4:193). The humanized pigs are treated with antibiotics (clindamycin, Augmentin, sultamicillin, ampicillin or amoxicillin) to disrupt their intestinal microbiome and then exposed to *C. difficile* after which they develop CDI including *C. difficile* associated diarrhea (CDAD).

To test the prophylactic potential of SYN-004 or modified-release formulations of P3A, P3A is administered one day prior to antibiotic treatment (Day −1), and maintained for the duration of the antibiotic treatment. Clindamycin is delivered 1 to 5 days prior to *C. difficile* inoculation. Oral antibiotics such as Augmentin, sultamicillin, ampicillin or amoxicillin, are delivered beginning 1 to 5 days prior to *C. difficile* inoculation, and maintained for 5-7 days. The antibiotics are used to disrupt the intestinal microbiome to predispose the animals to *C. difficile* infection. Plasma levels of antibiotics are monitored prior to antibiotic treatment, and during treatment to assess antibiotic absorption. *C. difficile* vegetative cells or spores are administered, at doses ranging from $10^6$ to $10^8$, and animals are monitored for CDI symptoms including CDAD. Animals exposed to *C. difficile* are expected to develop disease symptoms within 48 hrs of bacterial inoculation (Steele et al., 2010; J. Infect. Dis 201:428). CDI is compared in animals that receive clindamycin or oral antibiotics, such as Augmentin, sultamicillin, ampicillin or amoxicillin (Oral Antibiotic). The efficacy of the P3A treatment groups are compared to control animals that receive no treatment, animals that receive the standard of care, vancomycin (20 mg/kg orally daily beginning 24 hrs after infection and continued for 5 days), or animals that receive both vancomycin and P3A. The results may show that treatment with the oral antibiotics and the oral P3A at one or both doses, did not affect blood levels of the antibiotic and protected the animals from CDI, indicating that the P3A degraded the antibiotic excreted into the intestine following antibiotic absorption without affecting the initial antibiotic absorption. See TABLE 14 for the experimental design.

TABLE 14

SYN-004 or modified-release formulations of P3A C. difficile efficacy humanized pig study treatment groups

| Cohort (n = 2-3) | Antibiotic | C. diff inoculation | Treatment |
| --- | --- | --- | --- |
| 1 | none | None | none |
| 2 | Clindamycin (30 mg/kg) | + | none |
| 3 | Oral Antibiotic Dose TBD | + | none |
| 4 | Oral Antibiotic Dose TBD | + | vancomycin |
| 5 | Oral Antibiotic Dose TBD | + | SYN-004 or P3A High dose (12.5 mg/kg QID) |
| 6 | Oral Antibiotic Dose TBD | + | SYN-004 or P3A Low dose (0.5 mg/kg QID) |
| 7 | Oral Antibiotic Dose TBD | + | Vancomycin + SYN-004 (or P3A) Low dose (0.5 mg/kg QID) |

Example 11. Evaluation of SYN-004 and Oral Antibiotics in an Artificial Small and Large Intestine System The artificial small and large intestine system, TIM and/or TIM2 (see, e.g. Yoo, J. Y., & Chen, X. D. (2006). GIT physicochemical modeling—A Critical Review, *International Journal of Food Engineering*, 2(4), the contents of which are hereby incorporated by reference), is used to evaluate the current, enteric-coated SYN-004 formulation and/or modified-release formulations of SYN-004, e.g. as described herein, to more specifically localize the site(s) of SYN-004 release and antibiotic release within the intestinal track.

Example 12. Genetically-Modified Yeast for Delivery of P3A to the Intestinal Tract Genetically-modified microorganisms are tested as delivery vehicles to administer P3A to the intestinal track to protect the microbiome while not affecting antibiotic absorption and therefore, antibiotic efficacy.

Yeast genetically-modified to produce the antibiotic-degrading enzyme, P3A, are produced similarly to that described for the *C. difficile* toxin-binding proteins in "Methods and Compositions for Inhibiting *Clostridium difficile*" filed Nov. 4, 2014, Ser. No. 62/074,993, the contents of which are hereby incorporated by reference in their entirety. Briefly, the P3A coding region is codon optimized for expression in the yeast, *S. cerevasiae*, modified to reduced DNA homologies, and evaluated for the presence of N-linked glycosylation sites, synthesized and cloned into the yeast expression plasmid, pD1214 (DNA 2.0) that contains the strong, constitutive TEF promoter, and a selectable URA3+ marker. Different *S. cerevasiae* leader sequences that facilitate secretion are known and are utilized to mediate P3A secretion. A series of *S. cerevasiae* secretion vectors are available which contain a panel of different leader sequences to facilitate secretion. An exemplary secretion signal is the yeast mating factor alpha (MAT alpha) signal, which is a 89 amino acid sequence composed of the signal and the prosequence which is cleaved in the Golgi by Kex2, an endogenous yeast protease, to yield the mature, secreted protein. The invertase and other signal sequences are naturally cleaved during translocation and secretion of the protein by signal peptidase and do not require additional protease cleavage steps.

At least two strategies may be used to generate *S. cerevasiae*, substrain *boulardii*, transformants that secrete P3A. One strategy is the production of a *S. boulardii* URA3 knockout strain to allow the use of the P3A expression plasmids that contain the URA3 selectable marker to generate transformants (non-integrated, containing the plasmids) to use in efficacy evaluation in rodents and/or pigs. The *S. boulardii* URA3 knockout is generated using the CRISPR recombination system (DiCarlo et al, 2013, Nucleic Acids Res. 41:4436). The *S. boulardii* strain, designation Sb48 (ATCC Product #MYA-796) submitted to ATCC by D. A. Stevens (McCullough et al., 1998; J. Clinical Microbiology, 36:2613) is used for these studies. Three potential wild-type Cas9 cleavage sites in the upstream region of the URA3 gene are identified and approximately 500 pb of the regions surrounding these target sites are sequenced to ensure the presence of the sites in this yeast strain. A homology construct is designed that contains an approximate 10 bp region in the middle replaced by an insert that contains multiple stop codons in all frames ensuring that the first stop codon is in the URA3 reading frame. The CRISPR system is used to create the recombination/insertion and the URA3-clones are selected on FOA (5-fluoroorotic acid) media. 5-FOA allows the selection for URA3-mutants, as an active URA3 gene (encodes orotidine 5'-phosphate decarboxylase) converts FOA into a toxic compound causing cell death. The selected clones are then tested to ensure that they will not grow on media without uracil. Selected clones are sequenced to verify the expected integration. Once the *S. boulardii* strain is confirmed to be URA3-, the yeast are transformed with the P3A encoding plasmids. Clones are identified by plating on media without uracil. The resulting transformants are screened for secretion of P3A using SDS/PAGE. Filtered yeast supernatants are evaluated for activity using the CENTA beta-lactamase biological activity assay (Bebrone et al., 2001; Antimicrobial Agents and Chemotherapy, 45:1868).

A second strategy generates stable integrants in the wild-type *S. boulardii* strain using a neomycin resistance gene (neo) as the selectable marker. Without neo expression, *S. boulardii* is sensitive to G418. The *S. boulardii* strain, designation Sb48 (ATCC Product #MYA-796) submitted to ATCC by D. A. Stevens (McCullough et al., 1998; J. Clinical Microbiology, 36:2613) is used for these studies. Integration regions are chosen based on Flagfeldt et al (2009, Yeast 26:545), where chromosomal integration sites were screened for high level heterologous gene expression. The integration sites that show the highest expression levels, Regions 20, 21, and 19 are sequenced in the wild-type *S. boulardii* strain to verify their presence. Once verified, a region is chosen and plasmids containing integration cassettes are designed. The integration cassettes containing the P3A expression cassette, a neo expression cassette, at least 500 bp of homology sequence from the upstream part of the integration region and at least 500 bp of homology sequence from the downstream part of the integration region so that the integration region is deleted via the homologous recombination event. The wild-type S. boulardii is transformed with the integration cassettes and clones are selected for G418 resistance. Clones are picked, cultures grown, and supernatants screened for the presence of the P3A protein via SDS/PAGE. Filtered yeast supernatants are evaluated for biological activity using the CENTA beta-lactamase biological activity assay (Bebrone et al., 2001; Antimicrobial Agents and Chemo., 45:1868). Clones are chosen, based on protein expression levels and biological activity, and the insert is sequenced to verify the integrity of the integrated sequence.

The P3A-expressing yeast are tested in a rodent, pig, and/or dog model(s) to determine if the P3A-expressing yeast are efficacious in the degradation of an oral antibiotic/inhibitor combination or oral antibiotic alone, without affecting antibiotic absorption. For pig or dog studies, cohorts (n=3-5) of normal young pigs or beagle dogs are treated with clindamycin (once time) as a positive control for microbiome damage, or oral antibiotic/inhibitor (Augmentin or sultamicillin) or oral antibiotic (amoxicillin and/or ampicillin), for 5-7 consecutive days (TABLE 15). P3A-expressing yeast are delivered BID starting 3 days prior to antibiotic treatment and maintained throughout the antibiotic treatment period. Plasma and stool is collected daily, beginning the day prior to yeast treatment (Day −4) and prior to oral antibiotic treatment (Day −1). Plasma is monitored for antibiotic levels and stool is subjected to 16S RNA sequencing to monitor the diversity of the microbiome. The results may show that one or both of the antibiotic/P3A yeast doses, the plasma levels of antibiotic are not affected while the microbiome is protected, indicating that the P3A expressed by the yeast degraded the antibiotic excreted into the intestine following antibiotic absorption without affecting the initial antibiotic absorption.

The S. boulardii transformants expressing the P3A are evaluated in rodent models of C. difficile disease (CDI), including the Syrian Golden hamster (Mesocricetus auratus) C. difficile model (Sambol and Tang, 2001; J. Infect. Disease 183:1760) as described in Example 9.

To evaluate the prophylactic potential of the S. boulardii transformants expressing P3A, the yeast are administered, via oral gavage, at doses ranging from 100 to 500 mg, approximately $2\times10^8$ to $2\times10^{10}$ cfu/animal daily beginning at the time of antibiotic administration, 5 or 1 day prior to C. difficile infection, and continued for the duration of the studies, up to 28 days. As yeast are not sensitive to antibiotics, the yeast will remain viable even in the presence of antibiotics. Disease is compared in animals that receive clindamycin or oral Augmentin, sultamicillin, ampicillin, or amoxicillin (Oral Antibiotic). Plasma is monitored for antibiotic levels and stool is subjected to 16S RNA sequencing to monitor the diversity of the microbiome. The efficacy of the P3A-expressing yeast are compared to control animals that receive no treatment, animals that receive the standard of care, vancomycin (20 mg/kg orally daily beginning 24 hrs after infection and continued for 5 days), or animals that receive both vancomycin and the yeast. Efficacy evaluations include mortality and evaluation of C. difficile bacteria titers and/or C. difficile toxins A and B in cecal contents, at the time of death or at the end of the study following euthanasia. The results may show that treatment with the oral antibiotics and the P3A yeast at one or both doses, did not affect blood levels of the antibiotic and protected the animals from CDI, indicating that the P3A expressed by the yeast degraded the antibiotic excreted into the intestine following antibiotic absorption without affecting the initial antibiotic absorption. See TABLE 16 for the experimental design.

TABLE 15

Treatment of normal pigs and/or dogs with S. boulardii expressing P3A and an oral antibiotic/inhibitor (Augmentin or sultamicillin) or an oral antibiotic (amoxicillin and/or ampicillin)

| Cohort (n = 3-5) | Antibiotic | Oral S. boulardii |
|---|---|---|
| 1 | none | none |
| 2 | Clindamycin (30 mg/kg) | none |
| 3 | Oral Antibiotic High dose (TBD mg/kg BID) | S. boulardii wt $3 \times 10^{10}$ cfu BID |
| 4 | Oral Antibiotic High dose (TBD mg/kg BID) | S. boulardii P3A expressing $3 \times 10^{10}$ cfu BID |
| 5 | Oral Antibiotic High dose (TBD mg/kg BID) | none |
| 6 | Oral Antibiotic Low Dose (TBD mg/kg BID) | S. boulardii wt $3 \times 10^{10}$ cfu BID |
| 7 | Oral Antibiotic Low Dose (TBD mg/kg BID) | S. boulardii P3A expressing $3 \times 10^{10}$ cfu BID |
| 8 | Oral Antibiotic Low Dose (TBD mg/kg BID) | none |

TABLE 16

P3A-expressing yeast C. difficile efficacy hamster study treatment groups

| Cohort (n = 6-10) | Antibiotic | C. diff inoculation | Treatment |
|---|---|---|---|
| 1 | none | None | none |
| 2 | Clindamycin (30 mg/kg) | + | none |
| 3 | Oral Antibiotic Dose TBD | + | none |
| 4 | Oral Antibiotic Dose TBD | + | vancomycin |
| 5 | Oral Antibiotic Dose TBC | + | wt yeast High dose ($10^{10}$ cfu BID) |
| 6 | Oral Antibiotic Dose TBD | + | P3A yeast High dose ($10^{10}$ cfu BID) |
| 7 | Oral Antibiotic Dose TBD | + | P3A yeast Low dose ($10^8$ BID) |
| 8 | Oral Antibiotic Dose TBD | + | Vancomycin + P3A yeast High dose ($10^{10}$ cfu BID) |

Example 13. In Vivo Analysis of Yeast-Expressed P3A in Hamster CDI Model

P3A-expressing yeast are evaluated for the prevention of C. difficile infection and disease in a hamster model of C. difficile disease.

Example 14. In Vivo Analysis of Yeast-Expressed P3A in Porcine Model of CDI

Studies of the use of P3A-expressing yeast in the prevention of C. difficile infection and disease in a humanized pig model of C. difficile disease are undertaken.

The S. boulardii transformants expressing the P3A are tested in a humanized pig model of CDI. The humanized pig model is described in Example 10. The humanized pigs are treated with antibiotics (clindamycin or Augmentin, sultamicillin, ampicillin, or amoxicillin) to disrupt their intestinal microbiome and then exposed to *C. difficile* after which they develop CDI including *C. difficile* associated diarrhea (CDAD).

To test the prophylactic potential of P3A-expressing yeast, the yeast are administered one day prior to antibiotic treatment (Day −1), and delivered BID for the duration of the antibiotic treatment. Yeast are given at doses ranging from 250 mg to 3000 mg/animal, approximately $5 \times 10^9$ to $6 \times 10^{10}$ cfu/animal. Clindamycin is delivered 1 to 5 days prior to *C. difficile* inoculation. Oral Augmentin, sultamicillin, ampicillin, or amoxicillin (Oral Antibiotic) is delivered beginning 1 to 5 days prior to *C. difficile* inoculation, and maintained for 5-7 days. The antibiotics are used to disrupt the intestinal microbiome to predispose the animals to *C. difficile* infection. *C. difficile* vegetative cells or spores are administered, at doses ranging from $10^6$ to $10^8$, and animals are monitored for CDI symptoms including CDAD. CDI is compared in animals that receive clindamycin or Augmentin, sultamicillin, ampicillin, or amoxicillin (Oral Antibiotic). Plasma is monitored for antibiotic levels and stool is subjected to 16S RNA sequencing to monitor the diversity of the microbiome. The efficacy of the P3A-expressing yeast treatment groups are compared to control animals that receive no treatment, animals that receive the standard of care, vancomycin (20 mg/kg orally daily beginning 24 hrs after infection and continued for 5 days), or animals that receive both vancomycin and P3A-expressing yeast. The results may show that treatment with the oral antibiotics and the P3A yeast at one or both doses, did not affect blood levels of the antibiotic and protected the animals from CDI, indicating that the P3A expressed by the yeast degraded the antibiotic excreted into the intestine following antibiotic absorption without affecting the initial antibiotic absorption. See TABLE 17 for the experimental design

TABLE 17

P3A-expressing yeast *C. difficile* efficacy pig study treatment groups

| Cohort (n = 2-3) | Antibiotic | C. diff inoculation | Treatment |
|---|---|---|---|
| 1 | none | None | none |
| 2 | Clindamycin (30 mg/kg) | + | none |
| 3 | Oral Antibiotic Dose TBD | + | none |
| 4 | Oral Antibiotic Dose TBD | + | vancomycin |
| 5 | Oral Antibiotic Dose TBD | + | Wt yeast High dose ($3 \times 10^{10}$ cfu BID) |
| 6 | Oral Antibiotic Dose TBD | + | P3A yeast High dose ($3 \times 10^{10}$ cfu BID) |
| 7 | Oral Antibiotic Dose TBD | + | P3A yeast Low dose ($2.5 \; 10^9$ BID) |
| 8 | Oral Antibiotic Dose TBD | + | Vancomycin + P3A yeast High dose ($3 \times 10^{10}$ cfu BID) |

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

REFERENCES

The following are hereby incorporated by reference in their entireties:

Bevan, A, Brenner, C, Fuller, R S. (1998). Quantitative assessment of enzyme specificity in vivo: $P_2$ recognition by KEx2 protease defined in a genetic system. PNAS 95:10384-10389.

Davis, S S, Hardy, J G, Fara, J W. (2014). Transit of pharmaceutical dosage forms through the small intestine. Gut 27:886-892.

DiCarlo, J E, Norville, J E, Mali, P, Rios, X, Aach, J, Church, G M. (2013). Genome engineering in *Saccharomyces cerevisiae* using CRISPR-Cas systems. Nucl. Acids Res. 41: 4333.

Edwards-Ingram, L, Gitsham, P, Burton, N, Warhurst, G, Clarke, I, Hoyle, D, Oliver, S G, Stateva, L. (2007). Genotypic and physiological characterization of *Saccharomyces boulardii*, the probiotic strain of *Saccharomyces cerevisiae*. Appl. Environ. Microbiol. 73:2458.

Flagfeldt, D B, Siewers, V, Huang, L, Nielsen, J. (2009). Characterization of chromosomal integration sites for heterologous gene expression in *Saccharomyces cerevisiae*. Yeast 26:545.

Freeman, J, Wilcox, M H. (1999). Antibiotics and *Clostridium difficile*. Microbes Infect. 1:377-384.

Garrait, G, Jarrige, J F, Blanquet-Diot, S, Alric, M. (2009). Genetically engineered yeasts as a new delivery vehicle of active compounds to the digestive tract: In vivo validation of the concept in the rat. Metabolic Engineering 11:148-154.

Graff, S, Chaumeil, J-C, Boy, P, Lai-Kuen, R, Charrueau, C. (2008). Influence of pH conditions on the viability of *Saccharomyces boulardii* yeast. J. Gen. Appl. Microbiol. 54:221-227.

Hatoum R, Labrie, St, Fliss, I. (2012). Antimicrobial and probiotic properties of yeasts: from fundamental to novel applications. Frontiers in Microbiology 3: 421-421.

Hou, J, Tyo, K E J, Liu, Z, Petranovic, D, Nielsen, J. (2012). Metabolic engineering of recombinant protein secretion by *Saccharomyces cerevisiae*. FEMS Yeast Res. 12:491-510.

Kelesidis, T, Pothoulakis, C. (2012). Efficacy and safety of the probiotic *Saccharomyces boulardii* for the prevention and therapy of gastrointestinal disorders. Therapeutic Advances in Gastroenterology 5:111.

Klein, S M, Elmer, G W, McFarland, L V, Surawicz, C M, Levy, R H. (1993). Recovery and elimination of the biotherapeutic agent, *Saccharomyces boulardii*, in healthy human volunteers. Pharm Res. 10:1615-1619.

Liu, F, Moreno, P, Basit, A W. (2010). A novel double-coating approach for improved pH-triggered delivery to the ileo-colonic region of the gastrointestinal tract. European J. Pharm. Biopharma. 74:311-315.

McCoullough, M J, Clemons, K V, McCusker, J H, Stevens, D A. (1998). Species identification and virulence attributes of *Saccharomyces boulardii*. J. Clin. Microbiol. 36:2613.

Sambol, S P, Tang, J K. (2001). Infection of hamsters with epidemiologically important strains of Clostribium *difficile*. J. Infect. Diseases 183:1760.

Steele, J, Feng, H, Parry, N, Txipori, S. (2010). Piglet models for acute or chronic *Clostridium difficile* illness (CDI). J. Infect. Dis. 201:428.

Varum, F J O, Hatton, G B, Freire, A C, Basit, A W. (2013). A novel coating for ileo-colonic drug targeting: Proof of concept in humans using scintigraphy. European J. Pharm. Biopharma. 84:573-577.

Yigit, H, Queenan, A M, Anderson, G J, Domenech-Sanchez, A, Biddle, J W, Steward, C D, Alberti, S, Bush, K, Tenover, F C. (2001). Novel carbapenem-hydrolyzing beta-lactamase, KPC-1, from a carbapenem-resistant strain of *Klebsiella pneumoniae*. Antimicrobial Agents and Chemotherapy 45:1151-1161.

Zhang, Q, Widmer, G, Tzipori, S. (2013). A pig model of the human gastrointestinal tract. Gut Microbes 4:193.

Barr, W H, Zola, E M, Candler, E L, Hwang, S-M, Tendolkar, A V, Shamburek, R, Parker, B, Hilty, M D. (1994). Differential absorptions of amoxicillin from the human small and large intestine. Clin. Pharm. & Ther. 56:279-285.

Davis, S S, Hardy, J G, Fara, J W. (2014). Transit of pharmaceutical dosage forms through the small intestine. Gut 27:886-892.

Du, X., Li, C., Sun, H. K., Nightingale, C. H., Niclau, D. P. (2005). A sensitive assay of amoxicillin in mouse serum and broncho-alveolar lagage fluid by liquid-liquid extraction and reversed-phase HPLC. J. Pharm Biomed Anal 39:648-652.

Hasan, N. A., Young, B. A., Minard-Smith, A. T., Saeed, K., et al. (2014). Microbial community profiling of human saliva using shotgun metagenomic sequencing. PLoS One 2014, 9, e97699. 10.1371/journal.pone.0097699

Lax, S., Smith, D. P., Hampton-Marcell, J., Owens, S. M., et al (2014). Longitudinal analysis of microbial interaction between humans and the indoor environment. Science 2014, 345, 1048-1052. 10.1126/science.1254529

What is claimed is:

1. A beta-lactamase formulation comprising at least one particle with each particle comprising:
   about 0.1-1% beta-lactamase;
   about 0.1-1% hydroxypropylmethylcellulose acetate succinate (HPMCAS);
   about 5-15% ethylcellulose dispersion;
   about 0.1-1% sodium stearyl fumarate;
   about 0.1-1% buffer;
   about 0.5-5% trehalose; and
   about 80-90% water.

2. The formulation of claim 1, wherein the beta-lactamase comprises an amino acid sequence having at least 95% sequence identity with the amino acid sequence selected from SEQ ID NO: 1 and SEQ ID NO: 5.

3. The formulation of claim 1, wherein the beta-lactamase comprises an amino acid sequence having at least 98% sequence identity with the amino acid sequence selected from SEQ ID NO: 1 and SEQ ID NO: 5.

4. The formulation of claim 1, wherein the beta-lactamase comprises an amino acid sequence of SEQ ID NO: 1, having asparagine (N) replacing aspartic acid (D) at position 276, according to Ambler classification.

5. The formulation of claim 1, wherein the beta-lactamase comprises an amino acid sequence of SEQ ID NO: 1, having asparagine (N) replacing aspartic acid (D) at position 276 and having glycine (G) replace alanine (A) at position 232 and having serine (S) replacing alanine (A) at position 237 and having glycine (G) replacing alanine (A) at position 238 and having aspartic acid (D) replacing serine (S) at position 240, according to Ambler classification.

6. The formulation of claim 1, wherein the buffer is sodium hydrogen phosphate.

7. A beta-lactamase formulation comprising at least one pellet with each pellet comprising:
   about 0.5% by weight beta-lactamase, the beta-lactamase comprises an amino acid sequence having at least 95% identity with the amino acid sequence selected from SEQ ID NO: 1 and SEQ ID NO: 5;
   about 0.3% hydroxypropylmethylcellulose acetate succinate (HPMCAS);
   about 10.1% ethylcellulose dispersion;
   about 0.2% sodium stearyl sodium stearyl fumarate;
   about 0.1% buffer;
   about 1.0% trehalose; and
   about 88.8% water.

8. The formulation of claim 7, wherein the beta-lactamase comprises an amino acid sequence of SEQ ID NO: 1, having asparagine (N) replacing aspartic acid (D) at position 276, according to Ambler classification.

9. The formulation of claim 7, wherein the beta-lactamase comprises an amino acid sequence of SEQ ID NO: 1, having asparagine (N) replacing aspartic acid (D) at position 276 and having glycine (G) replace alanine (A) at position 232 and having serine (S) replacing alanine (A) at position 237 and having glycine (G) replacing alanine (A) at position 238 and having aspartic acid (D) replacing serine (S) at position 240, according to Ambler classification.

10. The formulation of claim 7, wherein the buffer is sodium hydrogen phosphate.

11. A method of preventing an antibiotic-associated adverse effect in a subject in need thereof, comprising administering the formulation of claim 1,
   wherein the antibiotic is an oral antibiotic, the oral antibiotic being a substrate for the beta-lactamase; and
   wherein the subject is undergoing treatment with the oral antibiotic.

12. The method of claim 11, wherein the antibiotic-associated adverse effect is *Clostridium difficile* infection.

13. The method of claim 11, wherein the antibiotic-associated adverse effect is antibiotic associated diarrhea.

14. The method of claim 11, wherein the beta-lactamase comprises an amino acid sequence of SEQ ID NO: 1, having asparagine (N) replacing aspartic acid (D) at position 276, according to Ambler classification.

15. The method of claim 11, wherein the beta-lactamase comprises an amino acid sequence of SEQ ID NO: 1, having asparagine (N) replacing aspartic acid (D) at position 276 and having glycine (G) replace alanine (A) at position 232 and having serine (S) replacing alanine (A) at position 237 and having glycine (G) replacing alanine (A) at position 238 and having aspartic acid (D) replacing serine (S) at position 240, according to Ambler classification.

16. The formulation of claim 11, wherein the buffer is sodium hydrogen phosphate.

17. A method of preventing an antibiotic-associated adverse effect in a subject in need thereof, comprising administering the formulation of claim 7,
   wherein the antibiotic is an oral antibiotic, the oral antibiotic being a substrate for the beta-lactamase; and
   wherein the subject is undergoing treatment with the oral antibiotic.

18. The method of claim 17, wherein the antibiotic-associated adverse effect is *Clostridium difficile* infection.

19. The method of claim 17, wherein the antibiotic-associated adverse effect is antibiotic associated diarrhea.

\* \* \* \* \*

SEQUENCE LISTING

```
<160> NUMBER OF SEQ ID NOS: 7

<210> SEQ ID NO 1
<211> LENGTH: 263
<212> TYPE: PRT
<213> ORGANISM: Bacillus licheniformis

<400> SEQUENCE: 1

Glu Met Lys Asp Asp Phe Ala Lys Leu Glu Glu Gln Phe Asp Ala Lys
1               5                   10                  15

Leu Gly Ile Phe Ala Leu Asp Thr Gly Thr Asn Arg Thr Val Ala Tyr
            20                  25                  30

Arg Pro Asp Glu Arg Phe Ala Phe Ala Ser Thr Ile Lys Ala Leu Thr
        35                  40                  45

Val Gly Val Leu Leu Gln Gln Lys Ser Ile Glu Asp Leu Asn Gln Arg
    50                  55                  60

Ile Thr Tyr Thr Arg Asp Asp Leu Val Asn Tyr Asn Pro Ile Thr Glu
65                  70                  75                  80

Lys His Val Asp Thr Gly Met Thr Leu Lys Glu Leu Ala Asp Ala Ser
                85                  90                  95

Leu Arg Tyr Ser Asp Asn Ala Ala Gln Asn Leu Ile Leu Lys Gln Ile
            100                 105                 110

Gly Gly Pro Glu Ser Leu Lys Lys Glu Leu Arg Lys Ile Gly Asp Glu
        115                 120                 125

Val Thr Asn Pro Glu Arg Phe Glu Pro Glu Leu Asn Glu Val Asn Pro
    130                 135                 140

Gly Glu Thr Gln Asp Thr Ser Thr Ala Arg Ala Leu Val Thr Ser Leu
145                 150                 155                 160
```

```
Arg Ala Phe Ala Leu Glu Asp Lys Leu Pro Ser Glu Lys Arg Glu Leu
                165                 170                 175

Leu Ile Asp Trp Met Lys Arg Asn Thr Thr Gly Asp Ala Leu Ile Arg
            180                 185                 190

Ala Gly Val Pro Asp Gly Trp Glu Val Ala Asp Lys Thr Gly Ala Ala
        195                 200                 205

Ser Tyr Gly Thr Arg Asn Asp Ile Ala Ile Ile Trp Pro Pro Lys Gly
    210                 215                 220

Asp Pro Val Val Leu Ala Val Leu Ser Ser Arg Asp Lys Lys Asp Ala
225                 230                 235                 240

Lys Tyr Asp Asp Lys Leu Ile Ala Glu Ala Thr Lys Val Val Met Lys
                245                 250                 255

Ala Leu Asn Met Asn Gly Lys
            260

<210> SEQ ID NO 2
<211> LENGTH: 792
<212> TYPE: DNA
<213> ORGANISM: Bacillus licheniformis

<400> SEQUENCE: 2
gagatgaaag atgattttgc aaaacttgag gaacaatttg atgcaaaact cgggatcttt      60
gcattggata caggtacaaa ccggacggta gcgtatcggc cggatgagcg ttttgctttt     120
gcttcgacga ttaaggcttt aactgtaggc gtgcttttgc aacagaaatc aatagaagat     180
ctgaaccaga gaataacata tacacgtgat gatcttgtaa actacaaccc gattacggaa     240
aagcacgttg atacgggaat gacgctcaaa gagcttgcgg atgcttcgct tcgatatagt     300
gacaatgcgg cacagaatct cattcttaaa caaattggcg gacctgaaag tttgaaaaag     360
gaactgagga agattggtga tgaggttaca aatcccgaac gattcgaacc agagttaaat     420
gaagtgaatc cggtgaaaac tcaggatacc agtacagcaa gagcacttgt cacaagcctt     480
cgagcctttg ctcttgaaga taaacttcca agtgaaaaac gcgagctttt aatcgattgg     540
atgaaacgaa ataccactgg agacgcctta atccgtgccg gtgtgccgga cggttgggaa     600
gtggctgata aaactggagc ggcatcatat ggaacccgga atgacattgc catcatttgg     660
ccgccaaaag gagatcctgt cgttcttgca gtattatcca gcagggataa aaaggacgcc     720
aagtatgatg ataaacttat tgcagaggca acaaaggtgg taatgaaagc cttaaacatg     780
aacggcaaat aa                                                        792

<210> SEQ ID NO 3
<211> LENGTH: 299
<212> TYPE: PRT
<213> ORGANISM: Bacillus licheniformis

<400> SEQUENCE: 3

Met Ile Gln Lys Arg Lys Arg Thr Val Ser Phe Arg Leu Val Leu Met
1               5                   10                  15

Cys Thr Leu Leu Phe Val Ser Leu Pro Ile Thr Lys Thr Ser Ala Gln
            20                  25                  30

Ala Ser Lys Thr Glu Met Lys Asp Asp Phe Ala Lys Leu Glu Glu Gln
        35                  40                  45

Phe Asp Ala Lys Leu Gly Ile Phe Ala Leu Asp Thr Gly Thr Asn Arg
    50                  55                  60

Thr Val Ala Tyr Arg Pro Asp Glu Arg Phe Ala Phe Ala Ser Thr Ile
65                  70                  75                  80
```

Lys Ala Leu Thr Val Gly Val Leu Leu Gln Gln Lys Ser Ile Glu Asp
             85                  90                  95

Leu Asn Gln Arg Ile Thr Tyr Thr Arg Asp Asp Leu Val Asn Tyr Asn
            100                 105                 110

Pro Ile Thr Glu Lys His Val Asp Thr Gly Met Thr Leu Lys Glu Leu
            115                 120                 125

Ala Asp Ala Ser Leu Arg Tyr Ser Asp Asn Ala Ala Gln Asn Leu Ile
            130                 135                 140

Leu Lys Gln Ile Gly Gly Pro Glu Ser Leu Lys Lys Glu Leu Arg Lys
145                 150                 155                 160

Ile Gly Asp Glu Val Thr Asn Pro Glu Arg Phe Glu Pro Glu Leu Asn
            165                 170                 175

Glu Val Asn Pro Gly Glu Thr Gln Asp Thr Ser Thr Ala Arg Ala Leu
            180                 185                 190

Val Thr Ser Leu Arg Ala Phe Ala Leu Glu Asp Lys Leu Pro Ser Glu
            195                 200                 205

Lys Arg Glu Leu Leu Ile Asp Trp Met Lys Arg Asn Thr Thr Gly Asp
210                 215                 220

Ala Leu Ile Arg Ala Gly Val Pro Asp Gly Trp Glu Val Ala Asp Lys
225                 230                 235                 240

Thr Gly Ala Ala Ser Tyr Gly Thr Arg Asn Asp Ile Ala Ile Ile Trp
            245                 250                 255

Pro Pro Lys Gly Asp Pro Val Val Leu Ala Val Leu Ser Ser Arg Asp
            260                 265                 270

Lys Lys Asp Ala Lys Tyr Asp Asp Lys Leu Ile Ala Glu Ala Thr Lys
            275                 280                 285

Val Val Met Lys Ala Leu Asn Met Asn Gly Lys
            290                 295

<210> SEQ ID NO 4
<211> LENGTH: 900
<212> TYPE: DNA
<213> ORGANISM: Bacillus licheniformis

<400> SEQUENCE: 4
atgattcaaa aacgaaagcg acagtttcg ttcagacttg tgcttatgtg cacgctgtta      60
tttgtcagtt tgccgattac aaaaacatca gcgcaagctt ccaagacgga gatgaaagat    120
gattttgcaa aacttgagga acaatttgat gcaaaactcg ggatctttgc attggataca    180
ggtacaaacc ggacggtagc gtatcggccg gatgagcgtt ttgcttttgc ttcgacgatt    240
aaggctttaa ctgtaggcgt gcttttgcaa cagaaatcaa tagaagatct gaaccagaga    300
ataacatata cacgtgatga tcttgtaaac tacaacccga ttacggaaaa gcacgttgat    360
acgggaatga cgctcaaaga gcttgcggat gcttcgcttc gatatagtga caatgcggca    420
cagaatctca ttcttaaaca aattggcgga cctgaaagtt tgaaaaagga actgaggaag    480
attggtgatg aggttacaaa tcccgaacga ttcgaaccag agttaaatga agtgaatccg    540
ggtgaaactc aggataccag tacagcaaga gcacttgtca caagccttcg agcctttgct    600
cttgaagata aacttccaag tgaaaaacgc gagcttttaa tcgattggat gaaacgaaat    660
accactggag acgccttaat ccgtgccggt gtgccggacg gttgggaagt ggctgataaa    720
actggagcgg catcatatgg aacccggaat gacattgcca tcatttggcc gccaaaagga    780
gatcctgtcg ttcttgcagt attatccagc agggataaaa aggacgccaa gtatgatgat    840
aaacttattg cagaggcaac aaaggtggta atgaaagcct taaacatgaa cggcaaataa    900

-continued

```
<210> SEQ ID NO 5
<211> LENGTH: 262
<212> TYPE: PRT
<213> ORGANISM: Artificial Sequence
<220> FEATURE:
<223> OTHER INFORMATION: Synthetic sequence

<400> SEQUENCE: 5

Glu Met Lys Asp Asp Phe Ala Lys Leu Glu Glu Gln Phe Asp Ala Lys
1               5                   10                  15

Leu Gly Ile Phe Ala Leu Asp Thr Gly Thr Asn Arg Thr Val Ala Tyr
            20                  25                  30

Arg Pro Asp Glu Arg Phe Ala Phe Ala Ser Thr Ile Lys Ala Leu Thr
        35                  40                  45

Val Gly Val Leu Leu Gln Gln Lys Ser Ile Glu Asp Leu Asn Gln Arg
    50                  55                  60

Ile Thr Thr Arg Asp Asp Leu Val Asn Tyr Asn Pro Ile Thr Glu Lys
65                  70                  75                  80

His Val Asp Thr Gly Met Thr Leu Lys Glu Leu Ala Asp Ala Ser Leu
                85                  90                  95

Arg Tyr Ser Asp Asn Ala Ala Gln Asn Leu Ile Leu Lys Gln Ile Gly
            100                 105                 110

Gly Pro Glu Ser Leu Lys Lys Glu Leu Arg Lys Ile Gly Asp Glu Val
        115                 120                 125

Thr Asn Pro Glu Arg Phe Glu Pro Glu Leu Asn Glu Val Asn Pro Gly
    130                 135                 140

Glu Thr Gln Asp Thr Ser Thr Ala Arg Ala Leu Val Thr Ser Leu Arg
145                 150                 155                 160

Ala Phe Ala Leu Glu Asp Lys Leu Pro Ser Glu Lys Arg Glu Leu Leu
                165                 170                 175

Ile Asp Trp Met Lys Arg Asn Thr Thr Gly Asp Ala Leu Ile Arg Ala
            180                 185                 190

Gly Val Pro Asp Gly Trp Glu Val Gly Asp Lys Thr Gly Ser Gly Asp
        195                 200                 205

Tyr Gly Thr Arg Asn Asp Ile Ala Ile Ile Trp Pro Pro Lys Gly Asp
    210                 215                 220

Pro Val Val Leu Ala Val Leu Ser Ser Arg Asp Lys Lys Asp Ala Lys
225                 230                 235                 240

Tyr Asp Asn Lys Leu Ile Ala Glu Ala Thr Lys Val Val Met Lys Ala
                245                 250                 255

Leu Asn Met Asn Gly Lys
            260

<210> SEQ ID NO 6
<211> LENGTH: 299
<212> TYPE: PRT
<213> ORGANISM: Artificial Sequence
<220> FEATURE:
<223> OTHER INFORMATION: Synthetic sequence

<400> SEQUENCE: 6

Met Ile Gln Lys Arg Lys Arg Thr Val Ser Phe Arg Leu Val Leu Met
1               5                   10                  15

Cys Thr Leu Leu Phe Val Ser Leu Pro Ile Thr Lys Thr Ser Ala Gln
            20                  25                  30

Ala Ser Lys Thr Glu Met Lys Asp Asp Phe Ala Lys Leu Glu Glu Gln
        35                  40                  45
```

Phe Asp Ala Lys Leu Gly Ile Phe Ala Leu Asp Thr Gly Thr Asn Arg
 50                  55                  60

Thr Val Ala Tyr Arg Pro Asp Glu Arg Phe Ala Phe Ser Thr Ile
 65                  70                  75                  80

Lys Ala Leu Thr Val Gly Val Leu Leu Gln Gln Lys Ser Ile Glu Asp
                 85                  90                  95

Leu Asn Gln Arg Ile Thr Tyr Thr Arg Asp Asp Leu Val Asn Tyr Asn
                100                 105                 110

Pro Ile Thr Glu Lys His Val Asp Thr Gly Met Thr Leu Lys Glu Leu
                115                 120                 125

Ala Asp Ala Ser Leu Arg Tyr Ser Asp Asn Ala Ala Gln Asn Leu Ile
130                 135                 140

Leu Lys Gln Ile Gly Gly Pro Glu Ser Leu Lys Lys Glu Leu Arg Lys
145                 150                 155                 160

Ile Gly Asp Glu Val Thr Asn Pro Glu Arg Phe Glu Pro Glu Leu Asn
                165                 170                 175

Glu Val Asn Pro Gly Thr Gln Asp Thr Ser Thr Ala Arg Ala Leu
                180                 185                 190

Val Thr Ser Leu Arg Ala Phe Ala Leu Glu Asp Lys Leu Pro Ser Glu
                195                 200                 205

Lys Arg Glu Leu Leu Ile Asp Trp Met Lys Arg Asn Thr Thr Gly Asp
210                 215                 220

Ala Leu Ile Arg Ala Gly Val Pro Asp Gly Trp Glu Val Gly Asp Lys
225                 230                 235                 240

Thr Gly Ser Gly Asp Tyr Gly Thr Arg Asn Asp Ile Ala Ile Ile Trp
                245                 250                 255

Pro Pro Lys Gly Asp Pro Val Val Leu Ala Val Leu Ser Ser Arg Asp
                260                 265                 270

Lys Lys Asp Ala Lys Tyr Asp Asn Lys Leu Ile Ala Glu Ala Thr Lys
                275                 280                 285

Val Val Met Lys Ala Leu Asn Met Asn Gly Lys
                290                 295

<210> SEQ ID NO 7
<211> LENGTH: 900
<212> TYPE: DNA
<213> ORGANISM: Artificial Sequence
<220> FEATURE:
<223> OTHER INFORMATION: Synthetic sequence

<400> SEQUENCE: 7
atgattcaaa aacgaaagcg acagtttcg ttcagacttg tgcttatgtg cacgctgtta      60
tttgtcagtt tgccgattac aaaaacatca gcgcaagctt ccaagacgga gatgaaagat     120
gattttgcaa aacttgagga acaatttgat gcaaaactcg ggatctttgc attggataca     180
ggtacaaacc ggacggtagc gtatcggccg gatgagcgtt ttgcttttgc ttcgacgatt     240
aaggctttaa ctgtaggcgt gcttttgcaa cagaaatcaa tagaagatct gaaccagaga     300
ataacatata cacgtgatga tcttgtaaac tacaacccga ttacggaaaa gcacgttgat     360
acgggaatga cgctcaaaga gcttgcggat gcttcgcttc gatatagtga caatgcggca     420
cagaatctca ttcttaaaca aattggcgga cctgaaagtt tgaaaaagga actgaggaag     480
attggtgatg aggttacaaa tcccgaacga ttcgaaccag agttaaatga agtgaatccg     540
ggtgaaactc aggataccag tacagcaaga gcacttgtca caagccttcg agcctttgct     600
cttgaagata aacttccaag tgaaaaacgc gagcttttaa tcgattggat gaaacgaaat     660

| | | | | | |
|---|---|---|---|---|---|
| accactggag | acgccttaat | ccgtgccggt | gtgccggacg | gttgggaagt gggtgataaa | 720 |
| actggaagcg | gagattatgg | aacccggaat | gacattgcca | tcatttggcc gccaaaagga | 780 |
| gatcctgtcg | ttcttgcagt | attatccagc | agggataaaa | aggacgccaa gtatgataat | 840 |
| aaacttattg | cagaggcaac | aaaggtggta | atgaaagcct | taaacatgaa cggcaaataa | 900 |